(12) United States Patent
Norton et al.

(10) Patent No.: US 8,933,132 B2
(45) Date of Patent: Jan. 13, 2015

(54) TRICYCLIC SUBSTITUTED BENZENESULFONAMIDE PIPERAZINE DERIVATIVES AS CAV2.2 CALCIUM CHANNEL BLOCKERS

(75) Inventors: David Norton, Cambridge (GB); Daniele Andreotti, Cambridge (GB); Simon E. Ward, Cambridge (GB); Roberto Profeta, Cambridge (GB); Simone Spada, Cambridge (GB); Helen Susanne Price, Cambridge (GB)

(73) Assignee: Convergence Pharmaceuticals Limited, London (GB)

( * ) Notice: Subject to any disclaimer, the term of this patent is extended or adjusted under 35 U.S.C. 154(b) by 0 days.

(21) Appl. No.: 13/979,830

(22) PCT Filed: Jan. 19, 2012

(86) PCT No.: PCT/GB2012/050111
§ 371 (c)(1),
(2), (4) Date: Oct. 22, 2013

(87) PCT Pub. No.: WO2012/098400
PCT Pub. Date: Jul. 26, 2012

(65) Prior Publication Data
US 2014/0038976 A1      Feb. 6, 2014

Related U.S. Application Data

(60) Provisional application No. 61/434,000, filed on Jan. 19, 2011.

(51) Int. Cl.
*A61K 31/10* (2006.01)
*C07C 317/32* (2006.01)
*C07D 471/14* (2006.01)
*C07D 487/14* (2006.01)

(52) U.S. Cl.
CPC ............ *C07D 471/14* (2013.01); *C07D 487/14* (2013.01)
USPC ............................... 514/764; 544/346; 568/34

(58) Field of Classification Search
CPC ............................... A61K 31/10; C07C 317/32
USPC ............................... 514/764; 544/346; 568/34
See application file for complete search history.

(56) References Cited

FOREIGN PATENT DOCUMENTS

WO    WO 2007/028638 A1    3/2007

OTHER PUBLICATIONS

Ahn et al. A Concise and Flexible Diastereoseletive Approach to Heteroring-Fused Isoindolinones. Synthesis (2011) 1:147-153.
Martini et al. Design, synthesis and preliminary pharmacological evaluation of new analogues of DM232 (unifiram) and DM235 (sunifiram) as cognition modulators. Bioorganic & Medicinal Chemistry (2008) 16(23):10034-10042.
Yoon et al. The Photochemistry of Polydonor-Substituted Phthalimides: Curtin-Hammett-Type Control of Competing Reactions of Potentially Interconverting Zwitterionic Biradical Intermediates. Journal of the American Chemical Society (2004) 126(4):1110-1124.

*Primary Examiner* — Douglas M Willis
(74) *Attorney, Agent, or Firm* — Foley & Lardner LLP

(57) ABSTRACT

The invention relates to novel piperazine compounds of formula (I):

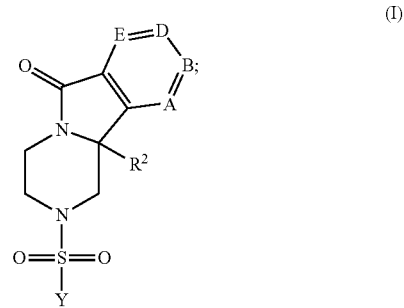

to processes for their preparation; to pharmaceutical compositions containing the compounds; and to the use of the compounds in therapy to treat diseases for which blocking the Cav2.2 calcium channels is beneficial, i.e. in particular to treat pain.

13 Claims, No Drawings

TRICYCLIC SUBSTITUTED BENZENESULFONAMIDE PIPERAZINE DERIVATIVES AS CAV2.2 CALCIUM CHANNEL BLOCKERS

CROSS-REFERENCE TO RELATED APPLICATIONS

This application is the U.S. national stage application of International Patent Application No. PCT/GB2012/050111, filed on Jan. 19, 2012, which claims priority to U.S. Provisional Application No. 61/434,000, filed on Jan. 19, 2011, each of which is incorporated herein by reference in its entirety.

TECHNICAL FIELD OF THE INVENTION

The present invention relates to novel piperazine derivatives; to processes for their preparation; to pharmaceutical compositions containing the compounds; and to the use of the compounds in therapy to treat diseases for which blocking the $Ca_v2.2$ calcium channels is beneficial, e.g. to treat pain.

BACKGROUND OF THE INVENTION

Pre-synaptic $Ca_v2.2$ (N-type) voltage-gated calcium channels in the dorsal horn of the spinal cord modulate the release of key pro-nociceptive neurotransmitters such as glutamate, substance P(SP) and calcitonin-gene-related peptide (CGRP), indicating the potential therapeutic use of $Ca_v2.2$ calcium channel blockers as analgesics.

Peptidic ω-conotoxins, isolated from the venom of cone snails, have been shown to be selective for $Ca_v2.2$ calcium channels and can block SP release in the spinal cord (Smith et al. (2002) Pain, 96: 119-127). Moreover, they have been shown to be antinociceptive in animal models of chronic pain following intrathecal administration (Bowersox et al. (1996) Journal of Pharmacology and Experimental Therapeutics, 279: 1243-1249; Smith et al. (2002) supra), and have been shown to be effective analgesics in clinical use, particularly in the treatment of neuropathic pain (Brose et al. (1997) Clinical Journal of Pain, 13: 256-259).

Winquist et al. has shown that $Ca_v2.2$ channels may offer the potential to reduce neuronal signalling, thereby treating disorders such as pain. However, side effect issues may impact the success of such an approach (Winquist et al. (2005) Biochemical Pharmacology, 70: 489-499). A number of journal articles have been published on the effect of natural inhibitors of $Ca_v2.2$ channels (see Bowersox et al. (1996) Journal of Pharmacology and Experimental Therapeutics 279 (3):1243-1249; Scott et al. (2002) European Journal of Pharmacology 451(3):279-286). In addition, several journal articles have been published on the phenotypic characterisation of transgenic mice lacking the $Ca_v2.2$ gene (see Saegusa et al. (2001) EMBO J. 20(10):2349-2356; Kim et al. (2001) Mol. Cell. Neurosci. 18(2):235-245). These articles support the stance that tonic inhibition of $Ca_v2.2$ may result in cardiovascular (hypotension) and CNS (sedation) side effects at therapeutic concentrations.

Due to these drawbacks of tonic $Ca_v2.2$ inhibitors, it is the object of the invention to provide an alternative class of $Ca_v2.2$ antagonist: a state- or use-dependent Cav2.2 blocker, which has the potential to selectively inhibit highly active channels contributing to the pathophysiology of chronic pain whilst sparing the contributions of Cav2.2 to wider physiological levels of activity within the peripheral and central nervous system. Therefore, the object of the invention is to identify novel compounds for use in therapy that preferentially block $Ca_v2.2$ calcium channels under conditions of increased neuronal excitability, so-called use-dependent blockers, as is the case in chronic pain syndromes.

SUMMARY OF THE INVENTION

According to a first aspect of the invention, there is provided a compound of formula (I):

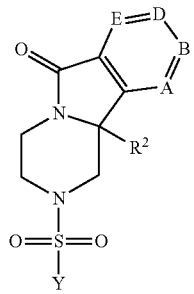

(I)

wherein
(a) A is N, B is $CR^{1b}$, D is $CR^{1d}$ and E is $CR^{1e}$; or
(b) B is N, A is $CR^{1a}$, D is $CR^{1d}$ and E is $CR^{1e}$; or
(c) D is N, A is $CR^{1a}$, B is $CR^{1b}$ and E is $CR^{1e}$; or
(d) E is N, A is $CR^{1a}$, B is $CR^{1b}$ and D is $CR^{1d}$;
$R^{1a}$, $R^{1b}$, $R^{1d}$ and $R^{1e}$ are independently selected from H and $C_{1-4}$ alkyl;
$R^2$ is H or $C_{1-4}$ alkyl;
Y is selected from

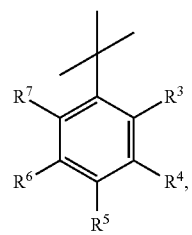

(i)

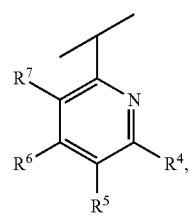

(ii)

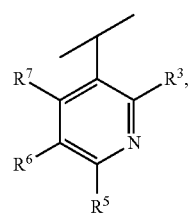

(iii)

(iv)

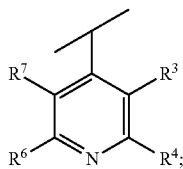

R³, R⁴, R⁵, R⁶ and R⁷ independently represent H, halogen, $C_{1-4}$ alkyl, $C_{1-4}$ alkoxy, cyano, $C_{1-4}$ haloalkyl or $C_{1-4}$ haloalkoxy, such that at least 1 of R³, R⁴, R⁵, R⁶ and R⁷ is a group other than H;

or a pharmaceutically acceptable salt thereof.

According to a further aspect, there is provided a compound as defined in the first aspect, or a pharmaceutically acceptable salt thereof, for use in therapy.

According to a further aspect, there is provided the use of a compound as defined in the first aspect, or a pharmaceutically acceptable salt thereof, in the manufacture of a medicament for the treatment or prophylaxis of pain.

According to a further aspect, there is provided a method for the treatment or prophylaxis of pain in a human or animal in need thereof comprising administering to said human or animal a therapeutically effective amount of a compound as defined in the first aspect, or a pharmaceutically acceptable salt thereof.

According to a further aspect, there is provided a pharmaceutical composition comprising (a) a compound as defined in the first aspect, or a pharmaceutically acceptable salt thereof, and (b) a pharmaceutically acceptable excipient.

DETAILED DESCRIPTION OF THE INVENTION

According to a first aspect of the invention, there is provided a compound of formula (I):

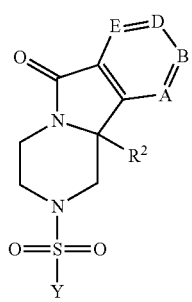

(I)

wherein
(a) A is N, B is $CR^{1b}$, D is $CR^{1d}$ and E is $CR^{1e}$; or
(b) B is N, A is $CR^{1a}$, D is $CR^{1d}$ and E is $CR^{1e}$; or
(c) D is N, A is $CR^{1a}$, B is $CR^{1b}$ and E is $CR^{1e}$; or
(d) E is N, A is $CR^{1a}$, B is $CR^{1b}$ and D is $CR^{1d}$;
$R^{1a}$, $R^{1b}$, $R^{1d}$ and $R^{1e}$ are independently selected from H and $C_{1-4}$ alkyl;
R² is H or $C_{1-4}$ alkyl;

Y is selected from

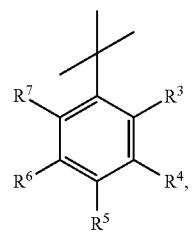

(i)

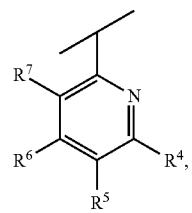

(ii)

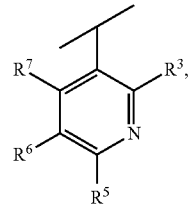

(iii)

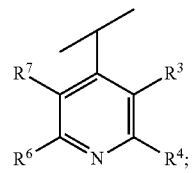

(iv)

R³, R⁴, R⁵, R⁶ and R⁷ independently represent H, halogen, $C_{1-4}$ alkyl, $C_{1-4}$alkoxy, cyano, $C_{1-4}$ haloalkyl or $C_{1-4}$ haloalkoxy, such that at least 1 of R³, R⁴, R⁵, R⁶ and R⁷ is a group other than H;

or a pharmaceutically acceptable salt thereof.

The term '$C_{1-4}$ alkyl' as used herein as a group or a part of a group refers to a linear or branched saturated hydrocarbon group containing from 1 to 4 carbon atoms, respectively. Examples of $C_{1-4}$ alkyl include methyl, ethyl, n-propyl and isopropyl. Unless a particular structure is specified, the term propyl includes all straight and branched chain forms e.g. propyl includes n-propyl and isopropyl.

The term 'halogen' as used herein refers to a fluoro, chloro, bromo or iodo.

The term '$C_{1-4}$ haloalkyl' as used herein refers to a $C_{1-4}$ alkyl group as defined herein substituted with one or more halogen groups, e.g. $CF_3$, $CF_2H$ or $CF_3CH_2$.

As used herein, the term '$C_{1-4}$ alkoxy' (when used as a group or as part of a group) refers to an —O—$C_{1-4}$alkyl group wherein $C_{1-4}$ alkyl is as defined herein.

The term $C_{1-4}$ haloalkoxy as used herein refers to an $C_{1-4}$ alkoxy group as defined herein substituted with one or more halogen groups, e.g. —O—$CF_3$.

According to a second aspect of the invention, there is provided a compound of formula (Ia), or a pharmaceutically acceptable salt thereof,

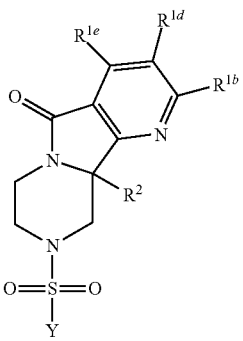

(Ia)

wherein $R^2$ and Y are defined as in the first aspect, and $R^{1b}$, $R^{1d}$ and $R^{1e}$ are independently selected from H and $C_{1-4}$ alkyl. In one embodiment, $R^{1d}$ and $R^{1e}$ are H. In another embodiment, $R^{1d}$ and $R^{1e}$ are H, $R^{1b}$ is $C_{1-4}$ alkyl, in particular methyl, and $R^2$ is H. In another embodiment, $R^{1b}$, $R^{1d}$ and $R^{1e}$ are H. In another embodiment, $R^{1b}$, $R^{1d}$, $R^{1e}$ and $R^2$ are H. In another embodiment, $R^{1b}$, $R^{1d}$, $R^{1e}$ are H and $R^2$ is methyl. In another embodiment, $R^{1d}$ and $R^{1e}$ are H, $R^{1b}$ is $C_{1-4}$ alkyl, in particular methyl, and $R^2$ is methyl.

According to a third aspect of the invention, there is provided a compound of formula (Ib), or a pharmaceutically acceptable salt thereof,

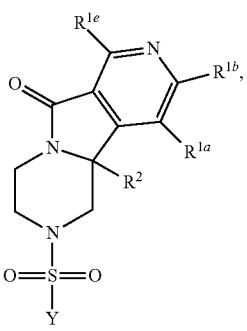

(Ib)

wherein $R^2$ and Y are defined as in the first aspect, and $R^{1a}$, $R^{1b}$ and $R^{1e}$ are independently selected from H and $C_{1-4}$ alkyl. In one embodiment, $R^{1a}$ and $R^{1e}$ are H, $R^{1b}$ is $C_{1-4}$ alkyl, in particular methyl, and $R^2$ is H. In another embodiment, $R^{1a}$ and $R^{1b}$ are H, $R^{1e}$ is $C_{1-4}$ alkyl, in particular methyl, and $R^2$ is H. In another embodiment, $R^{1a}$ and $R^{1b}$ are H, $R^{1e}$ is $C_{1-4}$ alkyl, in particular methyl, and $R^2$ is methyl.

In one embodiment of the first, second and third aspect, $R^{1a}$, $R^{1b}$, $R^{1d}$ and $R^{1e}$ are independently selected from H and methyl.

In one embodiment of the first, second and third aspect, $R^2$ is H or methyl. In a further embodiment, $R^2$ is H.

In one embodiment of the first, second and third aspect, Y is

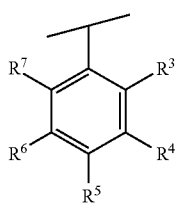

(i)

(herein referred to as (i)).

In one embodiment of the first, second and third aspect, $R^3$ is selected from H, halogen, $C_{1-4}$ alkyl, cyano and $C_{1-4}$ haloalkyl. In a further embodiment, $R^3$ is selected from H, methyl, cyano, trifluoromethyl and chloro. In a yet further embodiment, $R^3$ is selected from H or methyl.

In one embodiment of the first, second and third aspect, $R^4$ is selected from H, cyano, $C_{1-4}$ alkyl, $C_{1-4}$ haloalkyl and $C_{1-4}$ haloalkoxy. In a further embodiment, $R^4$ is selected from H, cyano, methyl, trifluoromethyl and trifluoromethoxy. In a yet further embodiment, $R^4$ is H.

In one embodiment of the first, second and third aspect, $R^5$ is selected from H, halogen, $C_{1-4}$ alkyl, $C_{1-4}$ alkoxy, cyano, $C_{1-4}$ haloalkyl and $C_{1-4}$ haloalkoxy. In a further embodiment, $R^5$ is selected from H, methoxy, ethoxy, isopropyloxy, trifluoromethyl, cyano, fluoro, trifluoromethoxy, difluoromethoxy, monofluoromethoxy and methyl. In a yet further embodiment, $R^5$ is selected from methoxy, isopropyloxy, trifluoromethyl, cyano and difluoromethoxy.

In one embodiment of the first, second and third aspect, $R^6$ is selected from H, halogen and $C_{1-4}$ alkyl. In a further embodiment, $R^6$ is selected from H, chloro and methyl. In a yet further embodiment, $R^6$ is H.

In one embodiment of the first, second and third aspect, $R^7$ is selected from H, $C_{1-4}$ alkyl and $C_{1-4}$ alkoxy. In a further embodiment, $R^7$ is selected from H, methyl and methoxy. In a yet further embodiment, $R^7$ is selected from H or methyl.

In one embodiment of the first, second and third aspect, Y is (i); $R^3$ is selected from H, halogen, $C_{1-4}$ alkyl, cyano and $C_{1-4}$ haloalkyl; $R^4$ is selected from H, cyano, $C_{1-4}$ alkyl, $C_{1-4}$ haloalkyl and $C_{1-4}$ haloalkoxy; $R^5$ is selected from H, halogen, $C_{1-4}$ alkyl, $C_{1-4}$ alkoxy, cyano, $C_{1-4}$ haloalkyl and $C_{1-4}$ haloalkoxy; $R^6$ is selected from H, halogen and $C_{1-4}$ alkyl and $R^7$ is selected from H, $C_{1-4}$ alkyl and $C_{1-4}$ alkoxy.

In one embodiment of the first, second and third aspect, Y is (i); $R^3$ is selected from H, methyl, cyano, trifluoromethyl and chloro; $R^4$ is selected from H, cyano, methyl, trifluoromethyl and trifluoromethoxy; $R^5$ is selected from H, methoxy, ethoxy, isopropyloxy, trifluoromethyl, cyano, fluoro, trifluoromethoxy, difluoromethoxy, monofluoromethoxy and methyl; $R^6$ is selected from H, chloro and methyl and $R^7$ is selected from H, methyl and methoxy.

In one embodiment of the first, second and third aspect, Y is (i); $R^3$ and $R^7$ are selected from H or $C_{1-4}$ alkyl (such as methyl); $R^4$ and $R^6$ are H; and $R^5$ is selected from $C_{1-4}$ alkoxy (such as methoxy or isopropyloxy), $C_{1-4}$ haloalkyl (such as trifluoromethyl), cyano and $C_{1-4}$ haloalkoxy (such as difluoromethoxy).

In one embodiment of the first, second and third aspect, $R^3$ is $C_{1-4}$ alkyl, $R^4$ is H, $R^5$ is $C_{1-4}$ haloalkyl, $R^6$ is H and $R^7$ is H. In a further embodiment of the first, second and third aspect, $R^3$ is methyl, $R^4$ is H, $R^5$ is trifluoromethyl, $R^5$ is H and $R^6$ is H.

In one embodiment of the first, second and third aspect, $R^3$ is $C_{1-4}$ alkyl, $R^4$ is H, $R^5$ is cyano, $R^6$ is H and $R^7$ is $C_{1-4}$ alkyl. In a further embodiment of the first, second and third aspect, $R^3$ is methyl, $R^4$ is H, $R^5$ is cyano, $R^6$ is H and $R^7$ is methyl.

In one embodiment of the first, second and third aspect, $R^3$ is $C_{1-4}$ alkyl, $R^4$ is H, $R^5$ is cyano, $R^6$ is H and $R^7$ is H. In a further embodiment of the first, second and third aspect, $R^3$ is methyl, $R^4$ is H, $R^5$ is cyano, $R^6$ is H and $R^7$ is H.

In one embodiment of the first, second and third aspect, $R^3$ is H, $R^4$ is H, $R^5$ is $C_{1-4}$ alkoxy, $R^6$ is H and $R^7$ is H. In a further embodiment of the first, second and third aspect, $R^3$ is H, $R^4$ is H, $R^5$ is isopropyloxy, $R^6$ is H and $R^7$ is H.

In one embodiment of the first, second and third aspect, $R^3$ is $C_{1-4}$ alkyl, $R^4$ is H, $R^5$ is $C_{1-4}$ alkoxy, $R^6$ is H and $R^7$ is $C_{1-4}$ alkyl. In a further embodiment of the first, second and third aspect, $R^3$ is methyl, $R^4$ is H, $R^5$ is methoxy, $R^6$ is H and $R^7$ is methyl.

In one embodiment of the first, second and third aspect, $R^3$ is H, $R^4$ is H, $R^5$ is $C_{1-4}$ haloalkoxy, $R^6$ is H and $R^7$ is H. In a further embodiment of the first, second and third aspect, $R^3$ is H, $R^4$ is H, $R^5$ is difluoromethoxy, $R^6$ is H and $R^7$ is H.

In one embodiment of the first, second and third aspect, $R^3$ is $C_{1-4}$ alkyl (such as methyl), $R^4$ is H, $R^5$ is $C_{1-4}$ haloalkyl (such as trifluoromethyl) or cyano, $R^5$ is H and $R^6$ is H.

In one embodiment of the first, second and third aspect, $R^3$ is $C_{1-4}$ alkyl (such as methyl), $R^4$ is H, $R^5$ is cyano or $C_{1-4}$ alkoxy (such as methoxy), $R^6$ is H and $R^7$ is $C_{1-4}$ alkyl (such as methyl).

In one embodiment of the first, second and third aspect, $R^3$ is H, $R^4$ is H, $R^5$ is $C_{1-4}$ alkoxy (such as isopropyloxy) or $C_{1-4}$ haloalkoxy (such as difluoromethoxy), $R^6$ is H and $R^7$ is H.

In one embodiment of the first, second and third aspect, a compound or salt is selected from Compounds 1 to 203 disclosed herein, or a pharmaceutically acceptable salt thereof.

Certain compounds as defined in the first to third aspect may in some circumstances form acid addition salts thereof. It will be appreciated that for use in medicine compounds of formula (I) may be used as salts, in which case the salts should be pharmaceutically acceptable. Pharmaceutically acceptable salts include those described by Berge, Bighley and Monkhouse, J. Pharm. Sci., 1977, 66, 1-19. The term "pharmaceutically acceptable salts" includes salts prepared from pharmaceutically acceptable acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Examples of pharmaceutically acceptable salts include those formed from maleic, fumaric, benzoic, ascorbic, pamoic, succinic, hydrochloric, sulfuric, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

It will be appreciated by those skilled in the art that certain protected derivatives of the compounds as defined in the first to third aspect, which may be made prior to a final deprotection stage, may not possess pharmacological activity as such, but may, in certain instances, be administered orally or parenterally and thereafter metabolised in the body to form compounds as defined in the first to third aspect which are pharmacologically active. Such derivatives may therefore be described as "prodrugs". All protected derivatives and prodrugs of compounds defined in the first to third aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compounds as defined in the first to third aspects. Therefore, in a further aspect, the invention provides a prodrug of a compound as defined in the first to third aspects.

It will be appreciated that certain compounds as defined in the first to third aspects, or their salts, may exist as solvates, such as hydrates. Where solvates exist, this invention includes within its scope stoichiometric and non-stoichiometric solvates.

It will be appreciated that certain compounds as defined in the first to third aspects, or their salts, may exist in more than one polymorphic form. The invention extends to all such forms whether in a pure polymorphic form or when admixed with any other material, such as another polymorphic form.

Certain compounds as defined in the first to third aspects are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The subject invention also includes isotopically-labelled compounds, which are identical to the compounds as defined in the first to third aspects, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^3H$, $^{11}C$, $^{14}C$ and $^{18}F$.

Compounds as defined in the first to third aspects and salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography). PET is useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula (I) and following of this invention can generally be prepared by carrying out the procedures disclosed in the Schemes and/or in the Examples below, by substituting a readily available isotopically labelled reagent for a non-isotopically labelled reagent. In one embodiment, compounds as defined in the first to third aspects or salts thereof are not isotopically labelled.

Throughout the specification, general formulae are designated by Roman numerals (I), (II), (III), (IV), etc. Subsets of these general formulae are defined as (Ia), (Ib), (Ic), etc. . . . (IVa), (IVb), (IVc), etc.

Compounds as defined in the first to third aspects may be prepared as set forth in the following Schemes and in the examples. The following processes form another aspect of the present invention.

Compounds of formula (I) may be prepared according to the following Scheme 1:

Scheme 1

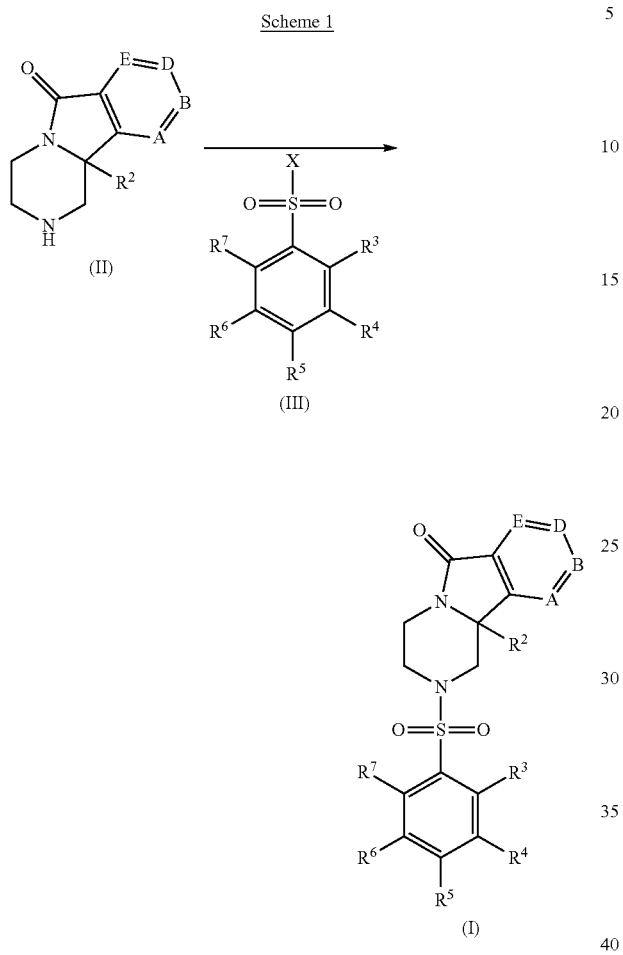

(I)

wherein A, B, D, E, $R^2$, $R^3$, $R^4$, $R^5$, $R^6$ and $R^7$ are as defined in the first aspect and X is a suitable leaving group such as a halogen, e.g. chloro.

A compound of formula (II) is reacted with a compound of formula (III) in the presence of a suitable base, e.g. DIPEA, in a suitable solvent, such as DCM, at a suitable temperature, e.g. room temperature.

Compounds of formula (III) are either commercially available, or may be prepared as disclosed herein or according to known methods.

Compounds of formula (IIa)

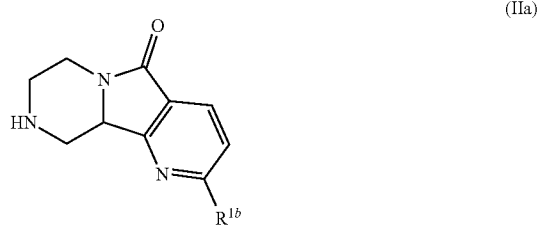

(IIa)

wherein $R^{1b}$ is as defined in the first aspect, may be prepared according to Scheme 2:

Scheme 2

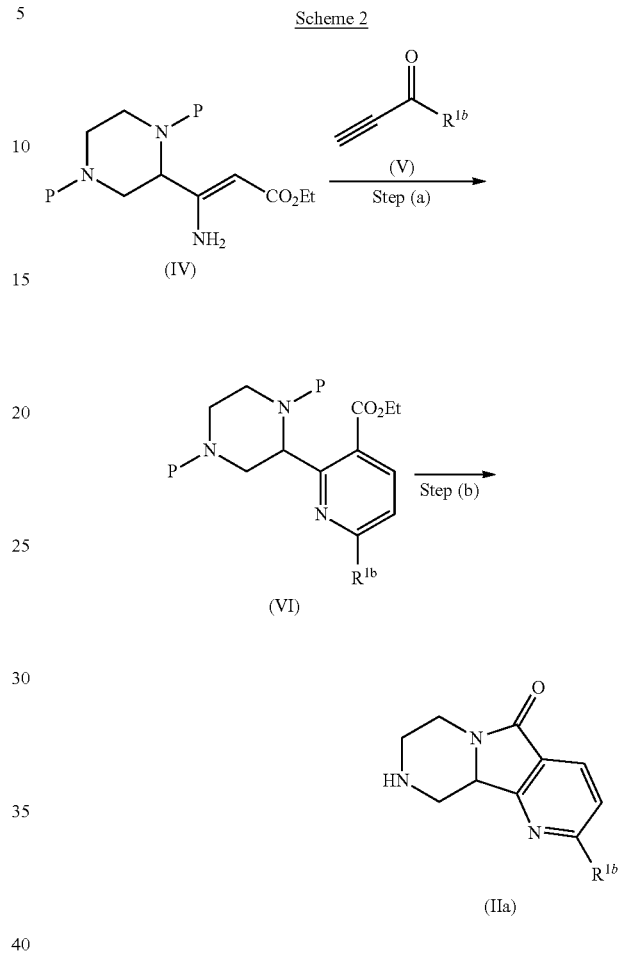

(IIa)

wherein $R^{1b}$ is as defined in the first aspect and P is a suitable protecting group such as t-butoxycarbonyl (BOC).

Step (a): Compound (IV) is reacted with a compound (V) in a suitable solvent, e.g. toluene or ethanol, at a suitable temperature such as at reflux temperature.

Step (b): Removal of the protecting group P. In case that the protecting group is t-butoxycarbonyl (BOC), compound (VI) is reacted with a strong acid, e.g. TFA, in a suitable solvent, e.g. DCM, at a suitable temperature such room temperature.

Compounds of formula (IV) and (V) may be prepared as exemplified in the experimental section or according to known methods.

Compounds of formula (IIb)

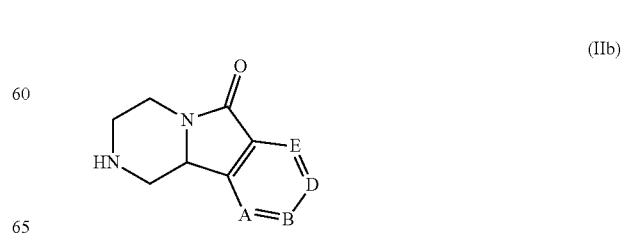

(IIb)

wherein A, B, D and E are as defined in the first aspect may also be prepared according to the following Scheme 3:

Scheme 3

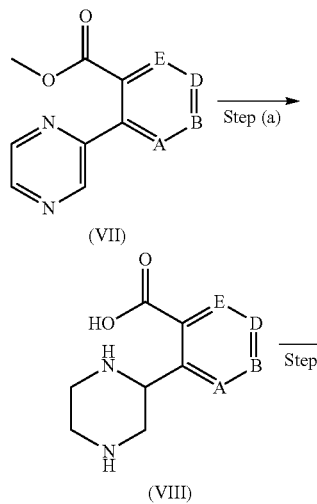

(VII)

(VIII)

(IIb)

wherein A, B, D and E are as defined in the first aspect.

Step (a) comprises two steps:

Step (a1): Hydrolysis of the ester group using a suitable reagent such as lithium hydroxide in a suitable solvent mixture such as methanol and water at a suitable temperature such as 80° C.

Step (a2): Reduction of the pyrazine ring by reaction under a positive pressure of hydrogen, such as 3 bar, with a suitable catalyst such as palladium on carbon, in a suitable solvent such as methanol.

Step (b): A compound of formula (VIII) is stirred under acidic conditions in a suitable solvent, e.g. ethanol, at a suitable temperature such as room temperature in the presence of a suitable methylating agent such TMS-diazomethane.

Compounds of formula (VII) may be prepared according to the following Scheme 4:

Scheme 4

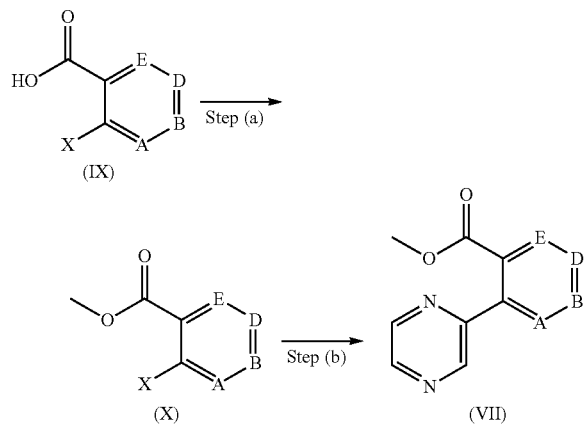

(IX)

(X)

(VII)

wherein A, B, D and E are as defined in the first aspect, and X is a suitable leaving group such as a halogen, e.g. chloro or bromo.

Step (a): A compound of formula (IX) is reacted with a suitable methylating agent such as TMS-diazomethane in a suitable solvent, e.g. DCM, and at a suitable temperature, e.g. room temperature.

Step (b): A compound of formula (X) is reacted with 2-(tributylstannanyl)pyrazine in a suitable solvent, e.g. toluene, at a suitable temperature such as 100° C., in the presence of a suitable catalyst, e.g. tetrakis(triphenylphosphine)palladium(0).

Compounds of formula (IX) are either commercially available or may be prepared according to known methods.

Compounds of formula (Id) may be prepared according to the following Scheme 5:

Scheme 5

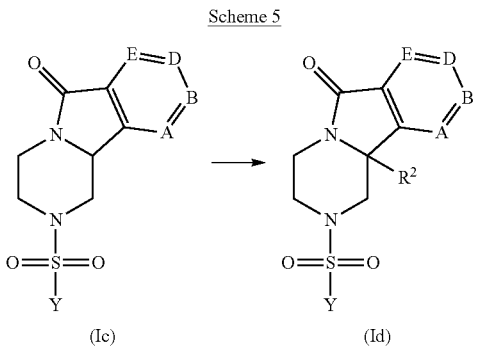

(Ic)

(Id)

wherein A, B, D, E, $R^2$ and Y are as defined in the first aspect.

A compound of formula (Ic) is treated with a suitable base, such LiHMDS, at a suitable temperature, for example −78° C., in a suitable solvent such as THF, and then reacted with methyl iodide, and the reaction mixture allowed to warm to room temperature.

Compounds of formula (III) may for example be prepared according to the following Scheme 6.

Scheme 6

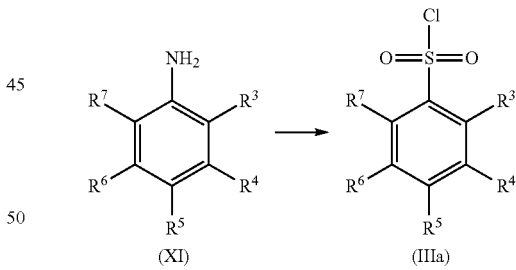

(XI)

(IIIa)

wherein $R^3$, $R^4$, $R^5$, $R^6$ and $R^7$ are as defined in the first aspect.

In the above reaction, compound (XI) is dissolved in acetic acid and concentrated sulphuric acid and the solution cooled to around 0° C. Sodium nitrite is then added and the reaction mixture kept cool before adding a saturated solution of sulphur dioxide in acetic acid to the reaction mixture while maintaining the temperature below 10° C.

Compounds of formula (XI) are either commercially available, or may be prepared by known methods.

The compounds as defined in the first to third aspects, or salts thereof, may be used to treat diseases for which blocking the $Ca_v2.2$ calcium channels is beneficial. Therefore, according to one aspect, the compounds as defined in the first to third aspects may be useful in the treatment or prophylaxis of pain, including acute pain, chronic pain, chronic articular pain, musculoskeletal pain, neuropathic pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, cancer chemotherapy, headache, toothache and dysmenorrhea.

'Chronic articular pain' conditions include rheumatoid arthritis, osteoarthritis, rheumatoid spondylitis, gouty arthritis and juvenile arthritis.

'Pain associated with functional bowel disorders' includes non-ulcer dyspepsia, non-cardiac chest pain and irritable bowel syndrome.

'Neuropathic pain' syndromes include: diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

'Inflammatory pain' conditions include skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, chronic obstructive pulmonary disease, (COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastro esophageal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, tendinitis, bursitis, and Sjogren's syndrome.

Compounds as defined in the first to third aspects may also be useful in the treatment or prophylaxis of disorders treatable and/or preventable with anti-convulsive agents, such as epilepsy including post-traumatic epilepsy, obsessive compulsive disorders (OCD), bipolar disorders, sleep disorders (including circadian rhythm disorders, insomnia & narcolepsy), tics (e.g. Giles de la Tourette's syndrome), ataxias, muscular rigidity (spasticity), and temporomandibular joint dysfunction. "Epilepsy" is intended to include the following seizures: simple partial seizures, complex partial seizures, secondary generalised seizures, generalised seizures including absence seizures, myoclonic seizures, clonic seizures, tonic seizures, tonic clonic seizures and atonic seizures.

Another condition which could potentially be treated by compounds as defined in the first to third aspects is spasticity or muscular hypertonicity.

It is believed that compounds as defined in the first to third aspects are particularly useful in the treatment or prophylaxis of pain, more particularly neuropathic pain, inflammatory pain and migraine, and epilepsy.

Thus, in one embodiment, the therapy is to the treatment or prophylaxis of any of the disorders described herein, in particular pain. In one particular embodiment, the therapy is to the treatment of any of the disorders described herein, in particular pain.

According to a further aspect, there is provided a use of a compound as defined in the first to third aspect, or a pharmaceutically acceptable salt thereof, in the manufacture of a medicament for the treatment or prophylaxis of any of the disorders herein, in particular pain. More particularly, there is provided a use of a compound as defined in the first to third aspects, or a pharmaceutically acceptable salt thereof, in the manufacture of a medicament for the treatment of any of the disorders herein.

According to another aspect, there is provided a method of treatment or prophylaxis of any of the disorders herein, in particular pain in humans, which method comprises the administration to the human in need of such treatment or prophylaxis, an effective amount of a compound as defined in the first to third aspects, or a pharmaceutically acceptable salt thereof.

In the context of the present invention, the term "treatment" refers to symptomatic treatment and the term "prophylaxis" is used to mean preventing symptoms in an already afflicted subject or preventing recurrence of symptoms in an afflicted subject and is not limited to complete prevention of an affliction.

In order to use a compound as defined in the first to third aspects or a pharmaceutically acceptable salt thereof for the treatment or prophylaxis of humans and other mammals it is normally formulated in accordance with standard pharmaceutical practice as a pharmaceutical composition. Therefore in another aspect of the invention there is provided a pharmaceutical composition comprising a compound as defined in the first to third aspects, or a pharmaceutically acceptable salt thereof, adapted for use in human or veterinary medicine.

In order to use compounds as defined in the first to third aspects in therapy, they will normally be formulated into a pharmaceutical composition in accordance with standard pharmaceutical practice. The present invention also provides a pharmaceutical composition, which comprises a compound as defined in the first to third aspects, or a pharmaceutically acceptable salt thereof, and optionally a pharmaceutically acceptable excipient.

When used in the treatment or prophylaxis of pain, the compound as defined in the first to third aspects or a pharmaceutically acceptable salt thereof may be used in combination with other medicaments indicated to be useful in the treatment or prophylaxis of pain of neuropathic origin including neuralgias, neuritis and back pain, and inflammatory pain including osteoarthritis, rheumatoid arthritis, acute inflammatory pain, back pain and migraine. Such therapeutic agents include for example COX-2 (cyclooxygenase-2) inhibitors, such as celecoxib, deracoxib, rofecoxib, valdecoxib, parecoxib, COX-189 or 2-(4-ethoxy-phenyl)-3-(4-methanesulfonyl-phenyl)-pyrazolo[1,5-b]pyridazine (WO99/012930); 5-lipoxygenase inhibitors; NSAIDs (non-steroidal anti-inflammatory drugs) such as diclofenac, indomethacin, nabumetone or ibuprofen; bisphosphonates, leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists or memantine; ligands for the $\alpha_2\delta$-subunit of voltage gated calcium channels, such as gabapentin, pregabalin and solzira; tricyclic antidepressants such as amitriptyline; neurone stabilising antiepileptic drugs; cholinesterase inhibitors such as galantamine; mono-aminergic uptake inhibitors such as venlafaxine; opioid analgesics; local anaesthetics; $5HT_1$ agonists, such as triptans, for Example sumatriptan, naratriptan, zolmitriptan, eletriptan, frovatriptan, almotriptan or rizatriptan; nicotinic acetyl choline (nACh) receptor modulators; glutamate receptor modulators, for Example modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabinoid receptor ligands; bradykinin receptor ligands; vanilloid receptor or Transient Receptor Potential (TRP) ligands; and purinergic receptor ligands, including antagonists at $P2X_3$, $P2X_{2/3}$, $P2X_4$, $P2X_7$ or $P2X_{4/7}$; KCNQ/Kv7 channel openers, such as retigabine; additional COX-2 inhibitors are disclosed in U.S. Pat. Nos. 5,474,995, 5,633,272; 5,466,823, 6,310,099 and 6,291,523; and in WO 96/25405, WO 97/38986, WO 98/03484, WO 97/14691, WO99/12930, WO00/26216, WO00/52008, WO00/38311, WO01/58881 and WO02/18374.

The invention thus provides, in a further aspect, a combination comprising a compound as defined in the first to third aspects or a pharmaceutically acceptable salt thereof together with a further therapeutic agent or agents.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10% to 60% by weight, of the active material, depending on the method of administration. The dose of the compound as defined in the first to third aspects or a pharmaceutically acceptable salt thereof used in the treatment or prophylaxis of the aforementioned disorders will vary in the usual way with the seriousness of the disorders, the weight of the sufferer, and other similar factors. However, as a general guide suitable unit doses may be 0.05 to 1000 mg, more suitably 20 to 600 mg, and such unit doses may be administered more than once a day, for example two or three a day. Such therapy may extend for a number of weeks, months, years or even life.

A further aspect to the invention is a pharmaceutical composition comprising 0.05 to 1000 mg of a compound as defined in the first to third aspects or a pharmaceutically acceptable salt thereof, and 0 to 3 g more suitably 0 to 2 g of at least one pharmaceutically acceptable carrier.

Abbreviations:
Ar: argon
aq.: aqueous
dba: dibenzylideneacetone
DCM: dichloromethane
DIPEA: N,N-diisopropylethylamine
DMF: N,N-dimethylformamide
DMSO: dimethylsulfoxide
DPPF: 1,1'-bis(diphenylphosphino)ferrocene
EDC: 1-ethyl-3-(3-dimethyllaminopropyl)carbodiimide hydrochloride
EtOAc: ethyl acetate
HATU: O-(7-azabenzotriazol-1-yl)-N,N,N',N'-tetramethyluronium hexafluorophosphate
HBTU: O-benzotriazole-N,N,N',N'-tetramethyl-uronium-hexafluoro-phosphate
HOBT: hydroxybenzotriazole
iHex: isohexane
LCMS: liquid Chromatography Mass Spectrometry
MS: mass spectrometry
MeCN: acetonitrile
MDAP: mass directed automated preparative liquid chromatography.
MeOH: methanol
rt: room temperature
sat.: saturated
SCX: strong cation exchange chromatography
SPE: solid phase extraction
SP4: Biotage-S P4® automated purification system
THF: tetrahydrofuran
TFA: trifluoroacetic acid
TMS-diazomethane: (trimethylsilyl)diazomethane
$Pd_2(dba)_3$: tris(dibenzylideneacetone)dipalladium(0)
$Pd(PPh_3)_4$: tetrakis(triphenylphosphine)palladium
h: hour(s)
min: minute(s)
Boc: t-butoxycarbonyl
$PdCl_2(dppf)_3$: (1,1'-bis(diphenylphosphino)ferrocene) dichloropalladium(II)
API-ES: atmospheric pressure ionization electro-spray
eq: equivalent
TLC: thin layer chromatography
RT: retention time
DMAP: 4-dimethylaminopyridine
DCC: dicyclohexylcarbodiimide CV: column volume
NMM: N-methylmorpholine
LiHMDS: lithium bis(trimethylsilyl)amide

EXAMPLES

The preparation of a number of supporting compounds as defined in the first to third aspects are described below.

In the procedures that follow, after each starting material, reference to an intermediate is typically provided. This is provided merely for assistance to the skilled chemist. The starting material may not necessarily have been prepared from the batch referred to.

Intermediate 1: 1,4-Bis{[(1,1-Dimethylethyl)oxy]carbonyl}-2-piperazinecarboxylic acid

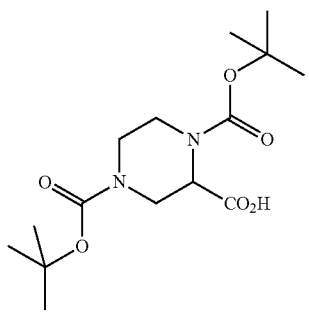 [SMILES: CC(C)(C)OC(=O)N1CCN(C(=O)OC(C)(C)C)C(C(=O)O)C1]

To a solution of 2-piperazinecarboxylic acid (10 g) dihydrochloride in methanol (500 mL) at 0° C. was added triethylamine (28.8 mL) dropwise via a dropping funnel. After addition, the solution was stirred for 30 minutes and then cooled to 0° C. before addition of di-tert-butyl dicarbonate (27.4 mL). The reaction was stirred for 18 h at room temperature. The reaction mixture was concentrated under vacuum and then partitioned between ethyl acetate (500 ml) and water (500 mL). The organic phase was washed with further water (500 mL) and then brine (300 mL) before it was dried ($Na_2SO_4$), filtered and the solvent removed under vacuum to give an oil of 3 g, which was discarded. The aqueous layer was acidified to pH 2 with 5M HCl and then extracted with ethyl acetate (2×700 mL). The organic phase was dried ($Na_2SC_4$), filtered and the solvent removed under vacuum to give the title compound as a white solid (14.58 g).

LCMS (low pH) RT 0.98 min:m/z (ES) 331 [M+H]$^+$

Intermediate 2: Bis(1,1-Dimethylethyl) 2-[(2,2-dimethyl-4,6-dioxo-1,3-dioxan-5-ylidene)(hydroxy)methyl]-1,4-piperazinedicarboxylate

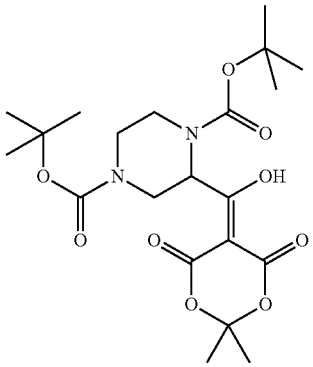 [SMILES: CC(C)(C)OC(=O)N1CCN(C(=O)OC(C)(C)C)C(C(O)=C2C(=O)OC(C)(C)OC2=O)C1]

To a solution of 1,4-bis{[(1,1-dimethylethyl)oxy]carbonyl}-2-piperazinecarboxylic acid (may be prepared as described in Intermediate 1; 14.58 g) in dichloromethane (500 mL) was added DMAP (8.09 g) and then DCC (13.66 g). The reaction was stirred for 15 minutes and then 2,2-dimethyl-1,3-dioxane-4,6-dione (9.54 g) (Meldrum's acid) was added. The reaction was stirred at room temperature for 20 h. A solid was present, which was filtered off and the product was found to be in the filtrate. The filtrate was washed with water (2×200 mL) and brine (200 mL) before it was dried ($Na_2SC_4$), filtered and the solvent removed under vacuum. The crude material was then redissolved in DCM (500 mL) and 50 mL removed and this was washed with 1M HCl (2×20 mL) before the organic phase was dried ($Na_2SC_4$), filtered and the solvent removed under vacuum to give the title compound (1.16 g). This process removed the DMAP impurity. The process was repeated with the remaining DCM solution, washing with 1M HCl (2×300 mL) before the solution was dried ($Na_2SC_4$), filtered and the solvent removed under vacuum to give the title compound as yellow viscous oil (16.65 g).

LCMS (low pH) RT 1.10 min:m/z (ES) 455 [M−H]$^-$

Intermediate 3: Bis(1,1-Dimethylethyl) 2-[3-(ethyloxy)-3-oxopropanoyl]-1,4-piperazinedicarboxylate

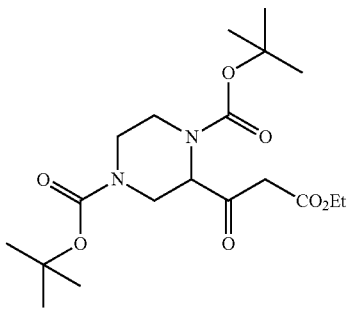 [SMILES: CCOC(=O)CC(=O)C1CN(C(=O)OC(C)(C)C)CCN1C(=O)OC(C)(C)C]

To a solution of bis(1,1-dimethylethyl) 2-[(2,2-dimethyl-4,6-dioxo-1,3-dioxan-5-ylidene)(hydroxy)methyl]-1,4-piperazinedicarboxylate (may be prepared as described in Intermediate 2; 8.32 g) in ethanol (250 mL) under argon, cooled to 0° C., was added dropwise a 21% weight solution of sodium ethoxide (118 mL). After completion of addition, the reaction was heated to reflux for 18 hours. The reaction mixture was evaporated and the residue partitioned between 2× ethyl acetate and water. The combined organic phases were washed with brine, dried through a hydrophobic frit, then evaporated to an orange oil. An attempt was made to dissolve in DCM for purification but a solid formed. This was evaporated and then triturated in ether. The resulting cream solid was collected by filtration, but was an impurity. The liquors were evaporated and then purified by silica column (SP4-40M) eluting with 0-40% ethyl acetate in iso-hexane over 12 CV. The clean fractions were combined and evaporated to give the title compound as a yellow oil (3.40 g).

LCMS (high pH) RT 1.21 min:m/z (ES) 399 [M−H]⁻

Intermediate 4: Bis(1,1-Dimethylethyl) 2-[(1Z)-1-amino-3-(ethyloxy)-3-oxo-1-propen-1-yl]-1,4-piperazinedicarboxylate

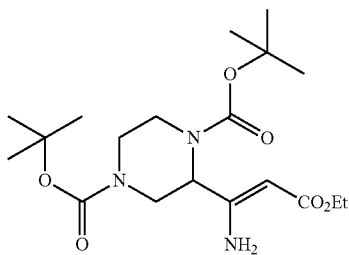 [SMILES: CCOC(=O)/C=C(\N)C1CN(C(=O)OC(C)(C)C)CCN1C(=O)OC(C)(C)C]

To a solution of bis(1,1-dimethylethyl) 2-[3-(ethyloxy)-3-oxopropanoyl]-1,4-piperazinedicarboxylate (may be prepared as described in Intermediate 3; 7.2 g) in ethanol (250 mL) was added ammonium acetate (6.93 g). The reaction mixture was heated to reflux for 7 hours and then left to stand at room temperature overnight. The reaction mixture was evaporated and then partitioned between 2× EtOAc and water. The combined organic phases were washed with water, dried through a hydrophobic frit and evaporated to give the title compound as a yellow oil (7.40 g).

LCMS (high pH) RT 1.25 min:m/z (ES) no mass ion [MH]+

Intermediate 5: Bis(1,1-Dimethylethyl) 2-{3-[(ethyloxy)carbonyl]-6-methyl-2-pyridinyl}-1,4-piperazinedicarboxylate

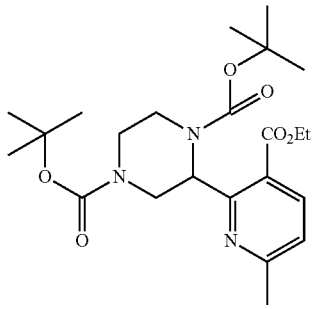 [SMILES: CCOC(=O)c1ccc(C)nc1C1CN(C(=O)OC(C)(C)C)CCN1C(=O)OC(C)(C)C]

To a solution of bis(1,1-dimethylethyl) 2-[(1Z)-1-amino-3-(ethyloxy)-3-oxo-1-propen-1-yl]-1,4-piperazinedicarboxylate (may be prepared as described in Intermediate 4; 7.4 g) in ethanol (300 mL), was added 3-butyn-2-one (3.15 g) and the reaction was heated to reflux for 20 hours. The reaction mixture was evaporated and then partitioned between 2× EtOAc and water. The combined organic phases were washed with brine, dried through a hydrophobic frit, and then evaporated to a brown oil (8.54 g), which was purified by silica column (SP4-40M) eluting with 0-40% ethyl acetate in iso-hexane over 12CV. The clean fractions were combined and evaporated to give the title compound as a yellow oil (4.96 g).

LCMS (high pH) RT 1.41 min:m/z (ES) 450[MH]+

Intermediate 6: 2-(3-Ethoxycarbonyl-pyridin-2-yl)-piperazine-1,4-dicarboxylic acid di-tert-butyl ester

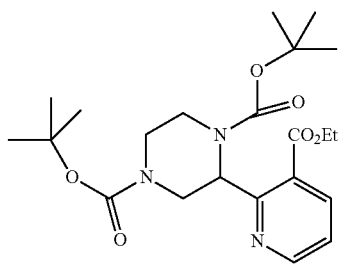 [SMILES: CCOC(=O)c1cccnc1C1CN(C(=O)OC(C)(C)C)CCN1C(=O)OC(C)(C)C]

To a solution of bis(1,1-Dimethylethyl) 2-[(1Z)-1-amino-3-(ethyloxy)-3-oxo-1-propen-1-yl]-1,4-piperazinedicarboxylate (may be prepared as described in Intermediate 4; 500 mg) in toluene (100 mL), propiolaldehyde (1.0 eq) was added at room temperature. After completion of addition, the reaction mixture was stirred for 2 h at room temperature and then heated to 90° C. Completion of reaction was followed by TLC. TLC showed disappearance of starting material in 5 h. Toluene was removed by vacuo then the residue was diluted with ethyl acetate (100 mL) and washed with water (2×50 mL) followed by brine solution (50 mL) and dried over anhydrous sodium sulphate, concentrated under vacuum to get 600 mg of crude product. The crude product was purified by column chromatography over 100-200 mesh silica gel by using 10%-30% ethyl acetate in pet ether as solvent, which yielded the title compound (200 mg).

m/z (ES) 436 (M+H)+

Intermediate 7: 8,9,10,10a-Tetrahydropyrido[2',3':3,4]pyrrolo[1,2-a]pyrazin-5(7H)-one

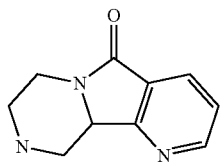 [SMILES: O=C1c2cccnc2C2CNCCN12]

To a solution of 2-(3-ethoxycarbonyl-pyridin-2-yl)-piperazine-1,4-dicarboxylic acid di-tert-butyl ester (may be prepared as described in Intermediate 6; 1.55 g) in DCM (100 mL), TFA (5.0 mL) was added at 0° C. and then reaction mixture was allowed to warm to room temperature. TLC showed disappearance of starting material in 4 h. Reaction mixture was fully evaporated under vacuum to give 1.70 g of crude intermediate. Crude intermediate was dissolved in methanol (100 mL), and then potassium carbonate (4.0 eq) was added. Reaction mixture was stirred at room temperature. TLC showed disappearance of intermediate in 5 h. The reaction mixture was filtered through celite, and the filtrate was concentrated under vacuum to get 800 mg of the crude product. The crude product was purified by column chromatography over 100-200 mesh silica gel by using 0%-10% methanol in chloroform as solvent, which gave the title compound (280 mg).

$^1$H NMR (DMSO, 400 MHz) δ: 8.77 (d, 1H), 8.17 (d, 1H), 7.58 (m, 1H), 4.48 (m, 1H), 4.17 (m, 1H), 3.58 (m, 1H), 3.05-2.95 (m, 2H), 2.39 (m, 1H) and 2.15 (t, 1H). m/z (ES) 190 (M+H)$^+$ Intermediate 8: 2-Methyl-8,9,10,10a-tetrahydropyrido[2',3':3,4]pyrrolo[1,2-a]pyrazin-5(7H)-one

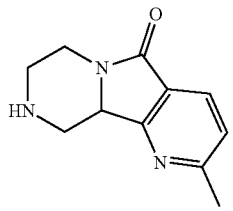

A solution of bis(1,1-dimethylethyl) 2-{3-[(ethyloxy)carbonyl]-6-methyl-2-pyridinyl}-1,4-piperazinedicarboxylate (may be prepared as described in Intermediate 5; 4.96 g) in dichloromethane (200 mL) was cooled to 0° C. and then TFA (20 mL, 260 mmol) was added. This was allowed to warm to room temperature then stirred for 4 hours. The reaction mixture was redissolved in DCM (100 ml), then TFA (10 ml) added and the whole stirred at room temperature for 1.5 hours. The reaction mixture was fully evaporated and azeotroped with toluene. This was dissolved in methanol (200 mL) and then potassium carbonate (3.05 g) was added and the mixture heated to reflux for 8 hours. The methanol was evaporated and the residue was partitioned between EtOAc and water. The organic layer was then washed with water and then brine, dried through a hydrophobic frit and then evaporated to an orange oil (87 mg), which was found to be impurities.

The aqueous phase was evaporated under vacuum to give a brown residue. A small portion of the brown residue was dissolved in MeOH and loaded onto a 50 g SCX cartridge, flushed with MeOH and then the compound eluted with 2M NH$_3$ in MeOH. This was evaporated to a brown oil, which was identified as the desired product. The remainder of the residue was also passed through 2×50 g SCX cartridges and all the desired fractions combined and evaporated to give the title compound as a brown oil (1.84 g)

LCMS (low pH) RT 0.32 min:m/z (ES) 204 [M+H]$^+$

Intermediate 9: Methyl 4-chloro-3-pyridinecarboxylate

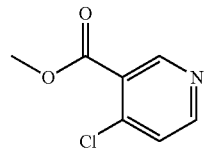

To a suspension of 4-chloro-3-pyridinecarboxylic acid (3.630 g) in dichloromethane (20 mL) and methanol (8 mL) stirred under argon at 0° C. was added TMS-diazomethane 2M in Et$_2$O (17.28 mL) dropwise. The reaction mixture was stirred at room temperature for 1 h. The solvents were evaporated in vacuo and the crude product was added to a silica gel column and was eluted with cyclohexane/EtOAc=7/3. The evaporation of the collected fractions gave 2.7 g of the title compound as a colourless solid.

LCMS (low pH) RT 0.65 min:m/z (ES) 172+174 [M+H]$^+$

Intermediate 10: Methyl 4-(2-pyrazinyl)-3-pyridinecarboxylate

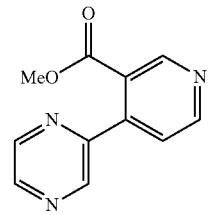 [SMILES: COC(=O)c1cnccc1-c1cnccn1]

To a solution of methyl 4-chloro-3-pyridinecarboxylate (1200 mg; may be prepared as described in Intermediate 18) and 2-(tributylstannanyl)pyrazine (3000 mg) in toluene (20 mL), tetrakis(triphenylphosphine)palladium(0) (808 mg) in toluene (20 mL) was added and the reaction mixture was stirred at 100° C. for 3 h. Then the solvent was evaporated in vacuo and the crude product was added to a silica gel column and eluted with cyclohexane/EtOAc/MeOH=7/2.5/0.5. The evaporation of the collected fractions gave 1 g of the title compound as a white solid.

LCMS (low pH) RT 0.51 min:m/z (ES) 216 [M+H]$^+$

Intermediate 11: 4-(2-piperazinyl)-3-pyridinecarboxylic acid

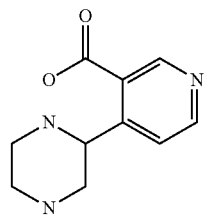 [SMILES: O=C(O)c1cnccc1C1CNCCN1]

To a solution of methyl 4-(2-pyrazinyl)-3-pyridinecarboxylate (400 mg; may be prepared as described in Intermediate 19) in methanol (20 mL) and water (3 mL) LiOH was added (44.5 mg). The reaction mixture was stirred at 80° C. for 2 h. The reaction mixture was filtered to remove the inorganic salts and evaporated in vacuo. The residue was dissolved in MeOH (20 ml), Pd/C (300 mg) was added and the reaction mixture was placed under hydrogen at 3 bar for 2 days. The reaction was monitored by LCMS which showed complete conversion of starting material. Then the catalyst was filtered by means of a celite plug and the filter was washed with MeOH. Then the solvent was evaporated in vacuo and the residue dissolved in 25 ml of MeOH to give a solution of the title compound, used directly in subsequent reactions.

Intermediate 12: 1,1-Dimethylethyl 6-oxo-3,4,6,10b-tetrahydropyrido[4',3':3,4]pyrrolo[1,2-a]pyrazine-2(1H)-carboxylate

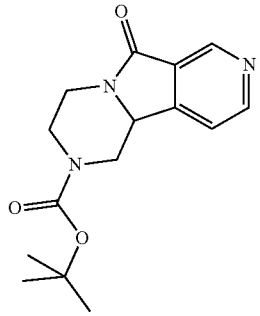 [SMILES: CC(C)(C)OC(=O)N1CCN2C(=O)c3cnccc3C2C1]

To 20 ml of the solution of Intermediate 20 in methanol was added HCl (1M in diethyl ether) until pH~5; after that was added TMS-diazomethane 2M in Et₂O (2 ml) and the reaction mixture was stirred at room temperature for 2 h. Then the solvent was evaporated in vacuo and the residue dissolved in THF and aqueous sodium bicarbonate. Boc₂O (0.426 mL) was added and the reaction mixture was stirred at room temperature for 2 h. Then the reaction mixture was partitioned between EtOAc and water. The organic phase was isolated, dried over sodium sulphate and evaporated in vacuo. The crude product was added to a silica gel column and was eluted with CH₂Cl₂/MeOH=95/5. The evaporation of the collected fractions gave a residue which was triturated with diethyl ether to give the title compound (43 mg).
LCMS (low pH) RT 0.70 min:m/z (ES) 290 [M+H]⁺

Intermediate 13: 1,3,4,10b-Tetrahydropyrido[4',3':3,4]pyrrolo[1,2-a]pyrazin-6(2H)-one

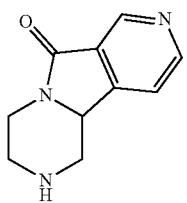 [SMILES: O=C1c2cnccc2C2CNCCN12]

To a solution of 1,1-dimethylethyl 6-oxo-3,4,6,10b-tetrahydropyrido[4',3':3,4]pyrrolo[1,2-a]pyrazine-2(1H)-carboxylate (may be prepared as in Intermediate 21; 90 mg) in 1,4-dioxane (2 mL) was added 4M hydrochloric acid in dioxane (1.166 mL). This was stirred at room temperature for 6 hours. The reaction mixture was evaporated to give the title compound as the HCl salt in the form of a white solid (91 mg).
LCMS (high pH) RT 0.37 min:m/z (ES) 190 [MH]⁺

Intermediate 14: 2-{[2-Bromo-4-(trifluoromethyl)phenyl]sulfonyl}-1,3,4,10b-tetrahydropyrido[4',3':3,4]pyrrolo[1,2-a]pyrazin-6(2H)-one (racemic)

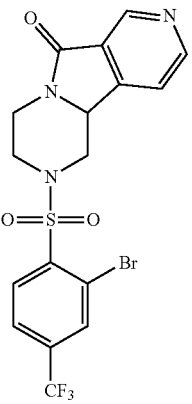 [SMILES: O=C1c2cnccc2C2CN(S(=O)(=O)c3ccc(C(F)(F)F)cc3Br)CCN12]

To a suspension of 1,3,4,10b-tetrahydropyrido[4',3':3,4]pyrrolo[1,2-a]pyrazin-6(2H)-one (may be prepared as in Intermediate 22, 90 mg) in dichloromethane (15 mL) was added DIPEA (0.415 mL). This was cooled in an ice bath and to this was added 2-bromo-4-(trifluoromethyl)benzenesulfonyl chloride (162 mg). The mixture was stirred at room temperature overnight. The reaction mixture was washed with aqueous saturated sodium bicarbonate solution in a hydrophobic frit and then re-extracted with DCM. The combined organic phases were evaporated to give the title compound as a yellow oil which was used in the next reaction (263 mg).
LCMS (low pH) RT 1.00 min:m/z (ES) 476+478 [MH]⁺

Intermediate 15: 9-{[2-Bromo-4-(trifluoromethyl)phenyl]sulfonyl}-8,9,10,10a-tetrahydropyrido[2',3':3,4]pyrrolo[1,2-a]pyrazin-5(7H)-one

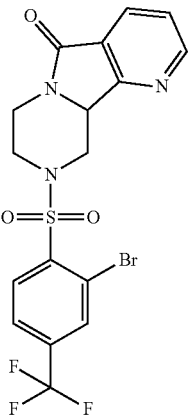 [SMILES: O=C1c2cccnc2C2CN(S(=O)(=O)c3ccc(C(F)(F)F)cc3Br)CCN12]

To a solution of 8,9,10,10a-tetrahydropyrido[2',3':3,4]pyrrolo[1,2-a]pyrazin-5(7H)-one (may be prepared as in Intermediate 7, 130 mg) in DCM (5 mL) was added DIPEA (0.360 mL, 2.061 mmol). The mixture was cooled to 0° C. and 2-bromo-4-(trifluoromethyl)benzenesulfonyl chloride (233 mg) was added.

This was stirred at room temperature for 2 hours. The reaction mixture was partitioned between DCM and saturated sodium bicarbonate solution, and then the aqueous was re-extracted with DCM. The combined organic phases were washed with water, dried through a hydrophobic frit then evaporated to give the title compound as an orange foam (266 mg).

LCMS (low pH) RT 1.05 min:m/z (ES) 476+478 [MH]+

Intermediate 16: 9-{[2-Bromo-4-(trifluoromethyl)phenyl]sulfonyl}-2-methyl-8,9,10,10a-tetrahydropyrido[2',3':3,4]pyrrolo[1,2-a]pyrazin-5(7H)-one

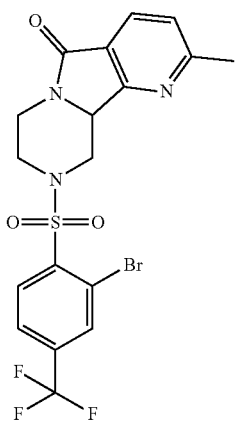 [SMILES: Cc1ccc2c(n1)C1CN(S(=O)(=O)c3ccc(C(F)(F)F)cc3Br)CCN1C2=O]

To the solution of 2-methyl-8,9,10,10a-tetrahydropyrido[2',3':3,4]pyrrolo[1,2-a]pyrazin-5(7H)-one (may be prepared as described in Intermediate 8; 100 mg) in dichloromethane (3.5 ml), DIPEA (0.129 ml) was added under argon atmosphere at room temperature then 2-bromo-4-(trifluoromethyl)benzenesulfonyl chloride (159 mg) was added at 0° C., and then the ice water bath was removed and the reaction mixture allowed to stir at room temperature for 3 h. The reaction mixture was partitioned between DCM (40 ml) and (20 ml) sodium bicarbonate. The organic phase was washed with sodium bicarbonate (20 ml), HCl (2×20 ml) and water (2×20 ml) and then it was dried using phase separator before the DCM was removed under vacuum to give the title compound (170 mg), which was used in next step without purification.

LCMS (low pH) RT 1.11 min:m/z (ES) 490+492 [MH]+

Intermediate 17: 4-Amino-3-methylbenzonitrile

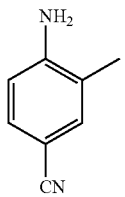

To an N-methylpyrrolidone (0.5 L) solution of 4-bromo-2-methylaniline (40 g) was added copper cyanide (38.5 g). The stirred mixture was heated at 200° C. for 2.5 hrs. The mixture was cooled to room temperature then water (1.9 L) and ammonia (0.5 L, 32%) were added. The mixture was extracted with ethyl acetate (2×1.2 L) and the combined organic phases then washed with a mixture of water/ammonia (0.5 L+0.2 L, 32%) and dried over $Na_2SO_4$. The solvent was evaporated under vacuum to give the title compound as a brown solid (27.5 g). This material was used in the next step without further purification.

Intermediate 18: 4-Cyano-2-methylbenzenesulfonyl chloride

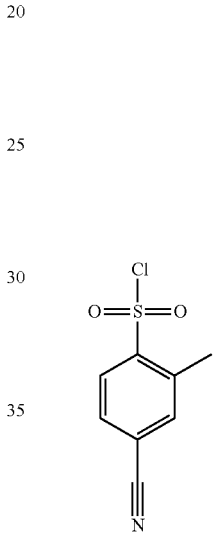

To an acetic acid (1.5 L) solution of 4-amino-3-methylbenzonitrile (may be prepared as described in Intermediate 17; 26 g) concentrated HCl (0.38 L) was added. The stirred reaction mixture was cooled at 0° C. and an aqueous solution of $NaNO_2$ (0.15 L, 13.6 g) was added maintaining the temperature below 5° C. for 45 min. Then the reaction mixture was slowly added (30 min) to a previously prepared saturated solution of $SC_2$ in acetic acid (2.7 L) containing copper chloride (105 g; 0.775 mol) maintaining the temperature at 10° C. The reaction temperature was raised to room temperature and stirred overnight. To the reaction mixture was added ice (1 Kg) and water (3.5 L), stirring the suspension for 30 min. The organic layer was extracted with ethyl acetate (2×3 L). The combined organic phases was washed with a saturated solution of $NaHCO_3$ to neutral pH, then with water (1 L) and brine (0.8 L). The organic phase was dried over $Na_2SC_4$ and the solvent was evaporated and the resulting crude material was purified by flash chromatography (cyclohexane/ethyl acetate 85/15) to give the title compound (4 g).

¹H NMR (400 MHz, DMSO-d₆) δ 7.89 (1H, d, J=8.0 Hz), 7.63 (1H, s), 7.61 (1H, d, J=8.0 Hz), 2.58 (3H, s) ppm.

Compound 1: 9-{[4-(Ethyloxy)phenyl]sulfonyl}-2-methyl-8,9,10,10a-tetrahydropyrido[2',3':3,4]pyrrolo[1,2-a]pyrazin-5(7H)-one (Racemic)

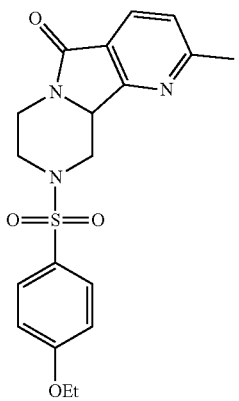 [SMILES: CCOc1ccc(S(=O)(=O)N2CCN3C(=O)c4ccc(C)nc4C3C2)cc1]

To a suspension of 2-methyl-8,9,10,10a-tetrahydropyrido[2',3':3,4]pyrrolo[1,2-a]pyrazin-5(7H)-one (may be prepared as described in Intermediate 8; 70 mg) in DCM (5 mL) was added DIPEA (0.241 mL, 1.378 mmol). To this was added 4-(ethyloxy)benzenesulfonyl chloride (80 mg) and this was allowed to stir at room temperature for 30 minutes. The reaction mixture was partitioned between DCM and saturated sodium bicarbonate solution in a hydrophobic frit. The aqueous layer was re-extracted with DCM. The combined organic phases were evaporated to an orange oil. The residue was purified by chromatography (25S silica cartridge) eluting with 0-5% methanol in DCM over 12 column volumes. The clean fractions were combined and evaporated to give the title compound as a white foam (84 mg).

LCMS (2 minute run, high pH) RT 0.96 min: MS (ES) requires 387. found [MH]+388 (100%)

The following compounds in Table 1 were prepared in a similar manner as Compound 1 using appropriate starting materials. Some were purified by MDAP rather than column chromatography.

TABLE 1

| Compound No. | Structure | Name | Characterisation (LCMS) |
|---|---|---|---|
| 2 | 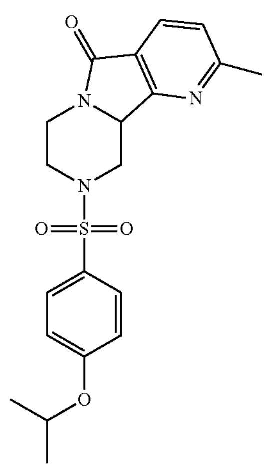 [SMILES: Cc1ccc2c(n1)C1CN(S(=O)(=O)c3ccc(OC(C)C)cc3)CCN1C2=O] | 2-Methyl-9-({4-[(1-methylethyl)oxy]phenyl}sulfonyl)-8,9,10,10a-tetrahydropyrido[2',3':3,4]pyrrolo-[1,2-a]pyrazin-5(7H)-one | (High pH) RT 1.02 min m/z 402 |
| 3 | 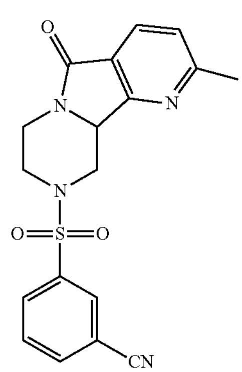 | 3-[(2-Methyl-5-oxo-7,8,10,10a-tetrahydropyrido[2',3':3,4]pyrrolo-[1,2-a]pyrazin-9(5H)-yl)sulfonyl]benzonitrile | (low pH) RT 0.79 min m/z 469 |

TABLE 1-continued

| Compound No. | Structure | Name | Characterisation (LCMS) |
|---|---|---|---|
| 4 | 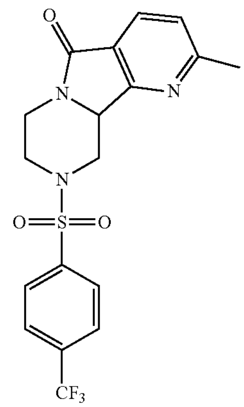 [SMILES: Cc1ccc2c(n1)C1CN(S(=O)(=O)c3ccc(C(F)(F)F)cc3)CCN1C2=O] | 2-Methyl-9-{[4-(trifluoromethyl)phenyl]sulfonyl}-8,9,10,10a-tetrahydropyrido[2',3':3,4]pyrrolo-[1,2-a]pyrazin-5(7H)-one | (High pH) RT 1.03 min m/z 412 |
| 5 | 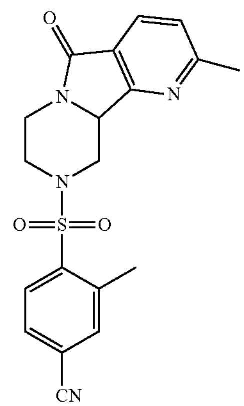 [SMILES: Cc1ccc2c(n1)C1CN(S(=O)(=O)c3ccc(C#N)cc3C)CCN1C2=O] | 3-Methyl-4-[(2-methyl-5-oxo-7,8,10,10a-tetrahydropyrido[2',3':3,4]pyrrolo-[1,2-a]pyrazin-9(5H)-yl)sulfonyl]benzonitrile | (Low pH) RT 0.86 min m/z 383 |
| 6 | 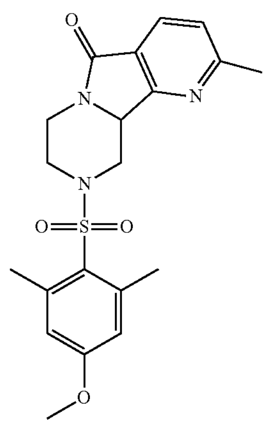 | 9-{[2,6-Dimethyl-4-(methyloxy)phenyl]sulfonyl}-2-methyl-8,9,10,10a-tetrahydropyrido[2',3':3,4]pyrrolo-[1,2-a]pyrazin-5(7H)-one | (High pH) RT 1.01 min m/z 402 |
| 7 | 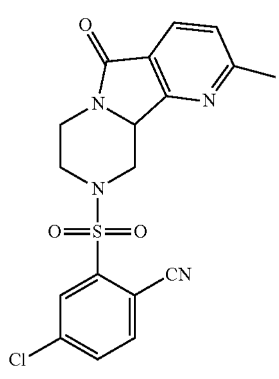 [SMILES: Cc1ccc2c(n1)C1CN(S(=O)(=O)c3cc(Cl)ccc3C#N)CCN1C2=O] | 4-Chloro-2-[(2-methyl-5-oxo-7,8,10,10a-tetrahydropyrido[2',3':3,4]pyrrolo-[1,2-a]pyrazin-9(5H)-yl)sulfonyl]benzonitrile | (High pH) RT 0.94 min m/z 403 + 405 |

TABLE 1-continued

| Compound No. | Structure | Name | Characterisation (LCMS) |
|---|---|---|---|
| 8 | 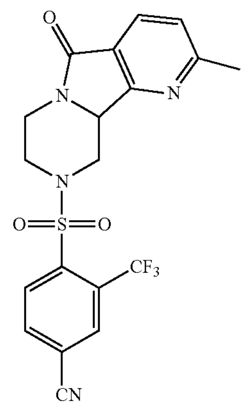 [SMILES: Cc1ccc2c(n1)C1CN(S(=O)(=O)c3ccc(C#N)cc3C(F)(F)F)CCN1C2=O] | 4-[(2-Methyl-5-oxo-7,8,10,10a-tetrahydropyrido[2',3':3,4]pyrrolo-[1,2-a]pyrazin-9(5H)-yl)sulfonyl]-3-(trifluoromethyl)benzonitrile | (High pH) RT 0.98 min m/z 437 |
| 9 | 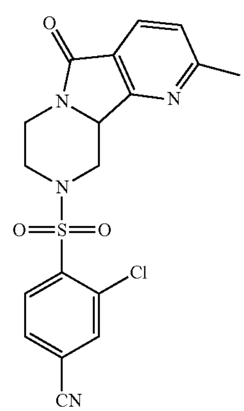 [SMILES: Cc1ccc2c(n1)C1CN(S(=O)(=O)c3ccc(C#N)cc3Cl)CCN1C2=O] | 3-Chloro-4-[(2-methyl-5-oxo-7,8,10,10a-tetrahydropyrido[2',3':3,4]pyrrolo-[1,2-a]pyrazin-9(5H)-yl)sulfonyl]benzonitrile | (High pH) RT 0.91 min m/z 403 + 405 |
| 10 | 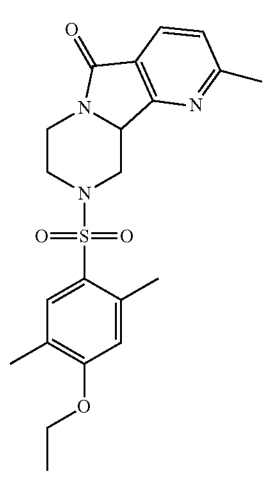 | 9-{[4-(Ethyloxy)-2,5-dimethylphenyl]sulfonyl}-2-methyl-8,9,10,10a-tetrahydropyrido[2',3':3,4]pyrrolo-[1,2-a]pyrazin-5(7H)-one | (High pH) RT 1.12 min m/z 416 |

TABLE 1-continued

| Compound No. | Structure | Name | Characterisation (LCMS) |
|---|---|---|---|
| 11 | 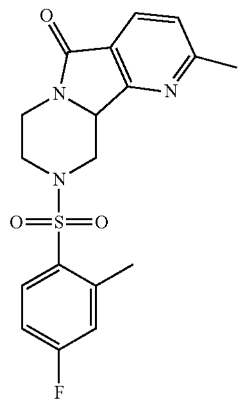 [SMILES: Cc1ccc2c(n1)C1CN(S(=O)(=O)c3ccc(F)cc3C)CCN1C2=O] | 9-[(4-Fluoro-2-methylphenyl)sulfonyl]-2-methyl-8,9,10,10a-tetrahydropyrido[2',3':3,4]pyrrolo-[1,2-a]pyrazin-5(7H)-one | (High pH) RT 0.96 min m/z 376 |
| 12 | 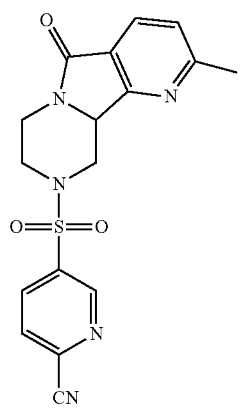 | 2-Methyl-9-{[6-(trifluoromethyl)-3-pyridinyl]sulfonyl}-8,9,10,10a-tetrahydropyrido[2',3':3,4]pyrrolo-[1,2-a]pyrazin-5(7H)-one | (High pH) RT 0.89 min m/z 413 |
| 13 | 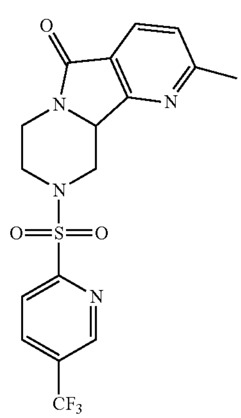 [SMILES: Cc1ccc2c(n1)C1CN(S(=O)(=O)c3ccc(C(F)(F)F)cn3)CCN1C2=O] | 2-Methyl-9-{[5-(trifluoromethyl)-2-pyridinyl]sulfonyl}-8,9,10,10a-tetrahydropyrido[2',3':3,4]pyrrolo-[1,2-a]pyrazin-5(7H)-one | (Low pH) RT 0.90 min m/z 413 |

TABLE 1-continued

| Compound No. | Structure | Name | Characterisation (LCMS) |
|---|---|---|---|
| 14 | 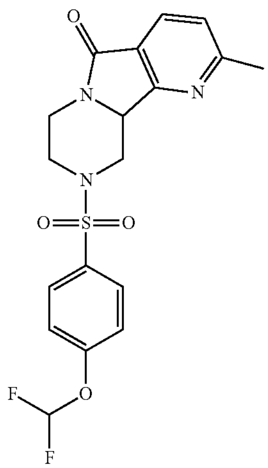 [SMILES: Cc1ccc2c(n1)C1CN(S(=O)(=O)c3ccc(OC(F)F)cc3)CCN1C2=O] | 9-({4-[(Difluoromethyl)oxy]phenyl}sulfonyl)-2-methyl-8,9,10,10a-tetrahydropyrido[2',3':3,4]pyrrolo-[1,2-a]pyrazin-5(7H)-one | (High pH) RT 0.94 min m/z 410 |
| 15 | 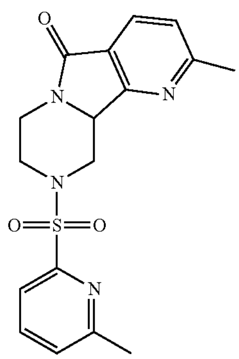 [SMILES: Cc1cccc(S(=O)(=O)N2CCN3C(=O)c4ccc(C)nc4C3C2)n1] | 2-Methyl-9-[(6-methyl-2-pyridinyl)sulfonyl]-8,9,10,10a-tetrahydropyrido[2',3':3,4]pyrrolo-[1,2-a]pyrazin-5(7H)-one | (High pH) RT 0.78 min m/z 359 |
| 16 | 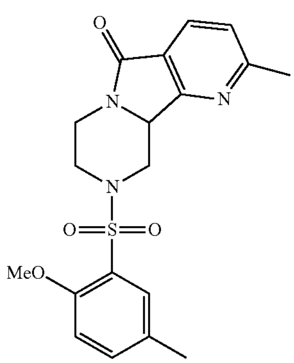 [SMILES: COc1ccc(C)cc1S(=O)(=O)N1CCN2C(=O)c3ccc(C)nc3C2C1] | 2-Methyl-9-{[5-methyl-2-(methyloxy)phenyl]sulfonyl}-8,9,10,10a-tetrahydropyrido[2',3':3,4]pyrrolo-[1,2-a]pyrazin-5(7H)-one | (High pH) RT 0.92 min m/z 388 |
| 17 | 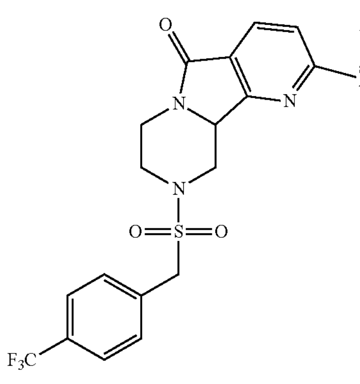 | 2-Methyl-9-({[4-(trifluoromethyl)phenyl]methyl}sulfonyl)-8,9,10,10a-tetrahydropyrido[2',3':3,4]pyrrolo-[1,2-a]pyrazin-5(7H)-one | (High pH) RT 1.01 min m/z 426 |

TABLE 1-continued

| Compound No. | Structure | Name | Characterisation (LCMS) |
|---|---|---|---|
| 18 | 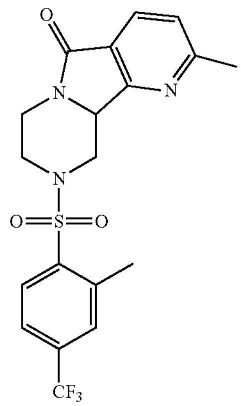 [SMILES: Cc1ccc2c(n1)C1CN(S(=O)(=O)c3ccc(C(F)(F)F)cc3C)CCN1C2=O] | 2-Methyl-9-{[2-methyl-4-(trifluoromethyl)phenyl]sulfonyl}-8,9,10,10a-tetrahydropyrido[2',3':3,4]pyrrolo-[1,2-a]pyrazin-5(7H)-one | (High pH) RT 1.08 min m/z 426 |
| 19 | 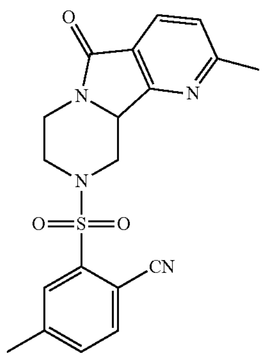 | 4-Methyl-2-[(2-methyl-5-oxo-7,8,10,10a-tetrahydropyrido[2',3':3,4]pyrrolo-[1,2-a]pyrazin-9(5H)-yl)sulfonyl]benzonitrile | (High pH) RT min m/z |

Compound 20: (10aS)-9-{[4-(Ethyloxy)phenyl]sulfonyl}-2-methyl-8,9,10,10a-tetrahydropyrido[2',3':3,4]pyrrolo[1,2-a]pyrazin-5(7H)-one and Compound 21: (10aR)-9-{[4-(Ethyloxy)phenyl]sulfonyl}-2-methyl-8,9,10,10a-tetrahydropyrido[2',3':3,4]pyrrolo[1,2-a]pyrazin-5(7H)-one Enantiomer 1: Faster Running Enantiomer (Compound 20 or Compound 21)

Chiral separation of 9-{[4-(ethyloxy)phenyl]sulfonyl}-2-methyl-8,9,10,10a-tetrahydropyrido[2',3':3,4]pyrrolo[1,2-a]pyrazin-5(7H)-one (75 mg; may be prepared as described in Compound 1) using Chiralpak AS, 50:50 Heptane:Ethanol.

Enantiomer 1=9.37 minutes (approx), afforded 37.3 mg.

Purity=99.9% w/w, e.e=99.8%.

Enantiomer 2: Slower Running Enantiomer (Compound 20 or Compound 21)

Chiral separation of 9-{[4-(ethyloxy)phenyl]sulfonyl}-2-methyl-8,9,10,10a-tetrahydropyrido[2',3':3,4]pyrrolo[1,2-a]pyrazin-5(7H)-one (75 mg; may be prepared as described in Compound 1) using Chiralpak AS, 50:50 Heptane:Ethanol.

Enantiomer 2=14.16 minutes, afforded 36 mg.

Purity=99.6% w/w, e.e=99.2%.

Compound 22: 9-{[4-(Ethyloxy)phenyl]sulfonyl}-2,10a-dimethyl-8,9,10,10a-tetrahydropyrido[2',3':3,4]pyrrolo[1,2-a]pyrazin-5(7H)-one

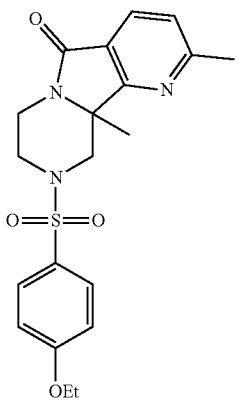 [SMILES: CCOc1ccc(S(=O)(=O)N2CCN3C(=O)c4ccc(C)nc4C3(C)C2)cc1]

To a solution of 9-{[4-(ethyloxy)phenyl]sulfonyl}-2-methyl-8,9,10,10a-tetrahydropyrido[2',3':3,4]pyrrolo[1,2-a]pyrazin-5(7H)-one (31 mg) in dry THF (0.5 mL) under argon at −78° C. was added LiHMDS (0.104 mL, 1M, in THF) dropwise. The reaction was stirred at −78° C. for 30 minutes and then the temperature of the cool bath raised to −50° C. over 15 minutes. A solution of methyl iodide (75 µL) in dry THF (1 mL) was made and then 100 μL of this solution added to the reaction dropwise. The reaction was then allowed to warm to −10° C. naturally in the cool bath and then the cool bath removed and the reaction stirred for 20 minutes. LCMS showed good conversion to product. The reaction mixture was concentrated in vacuo and then the mixture taken up in 1:1 MeOH:DMSO and this mixture filtered before purification by MDAP to give the title compound (14 mg) as white solid.

LCMS (low pH) RT 0.36 min, m/z (ES) 188 [M+H]$^+$ $^1$H NMR (400 MHz, CDCl$_3$) δ 7.96 (1H, d, J=8.4 Hz), 7.64 (2H, d, J=8.8 Hz), 7.25 (1H, d, J=8.4 Hz), 6.92 (2H, d, J=8.8 Hz), 4.42 (1H, m), 4.20 (1H, dd, J=11.6, 1.2 Hz), 4.05 (2H, q, J=7.6 Hz), 3.87 (1H, m), 3.36 (1H, m), 2.67 (3H, s), 2.19 (1H, td, J=12.0, 4.0, Hz), 1.89 (1H, d, J=11.6 Hz), 1.71 (3H, s), 1.41 (3H, t, J=7.6 Hz) ppm Compound 23: 9-{[2-Methyl-4-(trifluoromethyl) phenyl]sulfonyl}-8,9,10,10a-tetrahydropyrido[2',3':3, 4]pyrrolo[1,2-a]pyrazin-5(7H)-one (racemic)

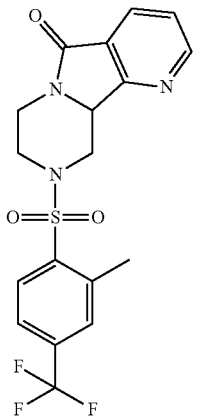

A mixture of 9-{[2-bromo-4-(trifluoromethyl)phenyl]sulfonyl}-8,9,10,10a-tetrahydropyrido[2',3':3,4]pyrrolo[1,2-a]pyrazin-5(7H)-one (265 mg; may be prepared as described in Intermediate 24), trimethylboroxin (182 mg), potassium carbonate (200 mg) and Pd(PPh$_3$)$_4$ (109 mg) was heated to 90° C. under argon for 6 hours. The reaction mixture was partitioned between EtOAc and saturated sodium bicarbonate solution, and then the aqueous was re-extracted with EtOAc. The combined organic phases were washed with brine, dried through a hydrophobic frit and evaporated to a brown oil (335 mg). The residue was purified by chromatography eluting with 0-90% ethyl acetate in iso-hexane over 12 column volumes. The desired fractions were combined and evaporated to give the title compound as a pale yellow crystalline solid (128 mg).

LCMS (high pH) RT 1.04 min:m/z (ES) 412 [MH]$^+$ $^1$H NMR (400 MHz, CDCl$_3$) δ 8.73 (1H, dd, J=4.8, 1.2 Hz), 8.15 (1H, dd, J=8.0, 1.2 Hz), 8.10 (1H, d, J=8.4 Hz), 7.63-7.58 (2H, m), 7.46 (1H, dd, J=8.0, 4.8 Hz), 4.69 (1H, dd, J=11.2, 4.4 Hz), 4.56-4.47 (2H, m), 3.99 (1H, m), 3.38 (1H, td, J=12.8, 4.4 Hz), 2.76 (1H, td, J=12.8, 3.6 Hz), 2.71 (3H, s), 2.44 (1H, dd, J=12.8, 11.2) ppm.

Compound 24: (10aS)-9-{[2-Methyl-4-(trifluoromethyl)phenyl]sulfonyl}-8,9,10,10a-tetrahydropyrido[2',3':3,4]pyrrolo[1,2-a]pyrazin-5(7H)-one and Compound 25: (10aR)-9-{[2-Methyl-4-(trifluoromethyl) phenyl]sulfonyl}-8,9,10,10a-tetrahydropyrido[2',3':3, 4]pyrrolo[1,2-a]pyrazin-5(7H)-one Enantiomer 1: faster running enantiomer (Compound 24 or Compound 25) Chiral separation of 9-{[2-methyl-4-(trifluoromethyl)phenyl]sulfonyl}-8,9,10,10a-tetrahydropyrido[2', 3':3,4]pyrrolo[1,2-a]pyrazin-5(7H)-one (110 mg; may be prepared as described in Compound 23) using Chiralpak AS, 50:50 Heptane:Ethanol. Enantiomer 1=5.66 minutes, afforded 50.1 mg.

Purity=99.9% w/w, 99.8% e.e

Enantiomer 2: slower running enantiomer (Compound 24 or Compound 25) Chiral separation of 9-{[2-methyl-4-(trifluoromethyl)phenyl]sulfonyl}-8,9,10,10a-tetrahydropyrido[2',3':3,4]pyrrolo[1,2-a]pyrazin-5(7H)-one (110 mg; may be prepared as described in Compound 23) using Chiralpak AS, 50:50 Heptane:Ethanol.

Enantiomer 2=8.51 minutes, afforded 53 mg.

Purity=99.4% w/w, 98.9% e.e

Compound 26: 2-{[4-(Trifluoromethyl)phenyl]sulfonyl}-1,3,4,10b-tetrahydropyrido[4',3':3,4]pyrrolo[1, 2-a]pyrazin-6(2H)-one

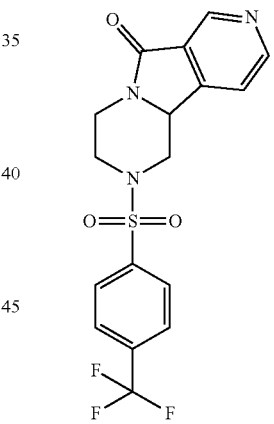

To 5 ml of the solution made of Intermediate 20 was added HCl 1M in diethyl ether until pH~5; after that was added TMS-diazomethane 2M in Et$_2$O (0.5 ml) and the reaction mixture was stirred at room temperature for 2 h. Then the solvent was evaporated in vacuo and the residue dissolved in THF and aqueous sodium bicarbonate; 4-(trifluoromethyl) benzenesulfonyl chloride (110 mg) was added and the reaction mixture was stirred at room temperature for 1 h. Then the reaction mixture was partitioned between EtOAc and water. The organic phase was isolated, dried over sodium sulphate and evaporated in vacuo. The crude product was added to a silica gel column and was eluted with CH$_2$Cl$_2$/MeOH=95/5. The evaporation of the collected fractions gave a residue which was triturated with diethyl ether to give the title compound as a solid (14 mg).

LCMS (low pH) RT 0.88 min:m/z (ES) 398 [MH]$^+$

Compound 27: 2-{[2-Methyl-4-(trifluoromethyl)phenyl]sulfonyl}-1,3,4,10b-tetrahydropyrido[4',3':3,4]pyrrolo[1,2-a]pyrazin-6(2H)-one (racemic)

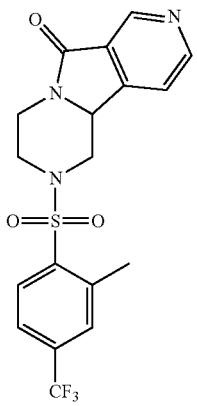

A mixture of 2-{[2-bromo-4-(trifluoromethyl)phenyl]sulfonyl}-1,3,4,10b-tetrahydropyrido[4',3':3,4]pyrrolo[1,2-a]pyrazin-6(2H)-one (250 mg), trimethylboroxin (0.190 mL), potassium carbonate (189 mg) and Pd(PPh$_3$)$_4$ (103 mg) was heated to 90° C. under argon for 18 hours. The reaction mixture was partitioned between EtOAc and aqueous saturated sodium bicarbonate solution. The aqueous phase was re-extracted with EtOAc. The combined organic phases were washed with brine, dried through a hydrophobic frit and evaporated to a brown oil. This was purified by chromatography eluting with 0-5% methanol in DCM over 12 column volumes. The clean fractions were combined and evaporated to a pale yellow gum. This was purified further to remove triphenylphosphine oxide by MDAP. The clean fraction was evaporated to give the title compound as a white solid (46 mg).

LCMS (low pH) RT 0.99 min:m/z (ES) 412 [MH]$^+$

Prophetic Compounds:

The following compounds in Table 2 to 9, or pharmaceutically acceptable salts thereof, may be prepared in a similar manner as the previous disclosed compounds.

TABLE 2

| Compound No. | Structure | Name |
|---|---|---|
| 28 | 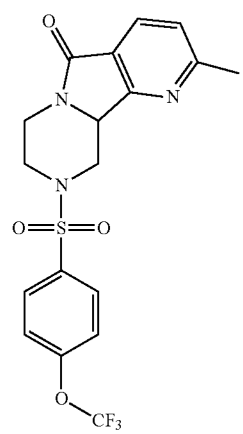 [SMILES: Cc1ccc2c(n1)C1CN(S(=O)(=O)c3ccc(OC(F)(F)F)cc3)CCN1C2=O] | 2-Methyl-9-({4-[(trifluoromethyl)oxy]phenyl}sulfonyl)-8,9,10,10a-tetrahydropyrido[2',3':3,4]pyrrolo[1,2-a]pyrazin-5(7H)-one |
| 29 | 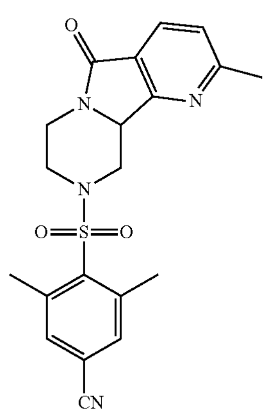 | 3,5-Dimethyl-4-[(2-methyl-5-oxo-7,8,10,10a-tetrahydropyrido[2',3':3,4]pyrrolo[1,2-a]pyrazin-9(5H)-yl)sulfonyl]benzonitrile |

TABLE 2-continued

| Compound No. | Structure | Name |
|---|---|---|
| 30 | 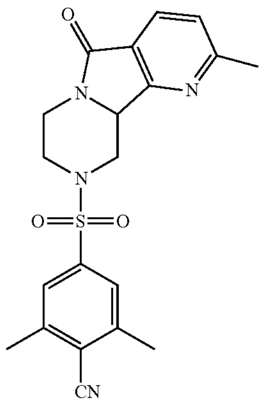 | 2,6-Dimethyl-4-[(2-methyl-5-oxo-7,8,10,10a-tetrahydropyrido[2',3':3,4]pyrrolo[1,2-a]pyrazin-9(5H)-yl)sulfonyl]benzonitrile |
| 31 | 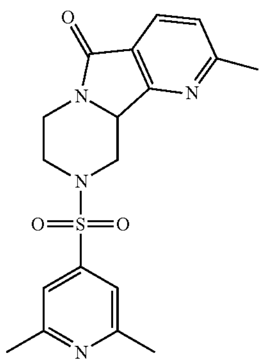 | 9-[(2,6-Dimethyl-4-pyridinyl)sulfonyl]-2-methyl-8,9,10,10a-tetrahydropyrido[2',3':3,4]pyrrolo[1,2-a]pyrazin-5(7H)-one |
| 32 | 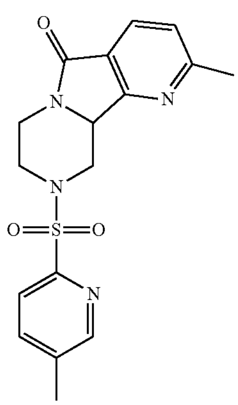 [SMILES: Cc1ccc(S(=O)(=O)N2CCN3C(=O)c4ccc(C)nc4C3C2)nc1] | 2-Methyl-9-[(5-methyl-2-pyridinyl)sulfonyl]-8,9,10,10a-tetrahydropyrido[2',3':3,4]pyrrolo[1,2-a]pyrazin-5(7H)-one |
| 33 | 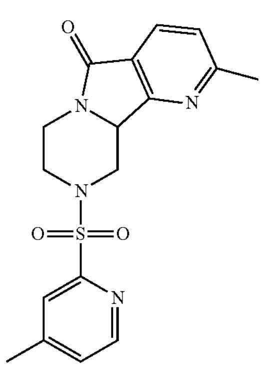 | 2-Methyl-9-[(4-methyl-2-pyridinyl)sulfonyl]-8,9,10,10a-tetrahydropyrido[2',3':3,4]pyrrolo[1,2-a]pyrazin-5(7H)-one |

TABLE 2-continued

| Compound No. | Structure | Name |
|---|---|---|
| 34 | 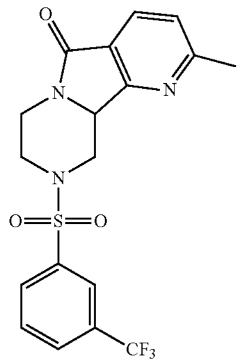 [SMILES: Cc1ccc2c(n1)C1CN(S(=O)(=O)c3cccc(C(F)(F)F)c3)CCN1C2=O] | 2-Methyl-9-{[3-(trifluoromethyl)phenyl]sulfonyl}-8,9,10,10a-tetrahydropyrido[2',3':3,4]pyrrolo[1,2-a]pyrazin-5(7H)-one |
| 35 | 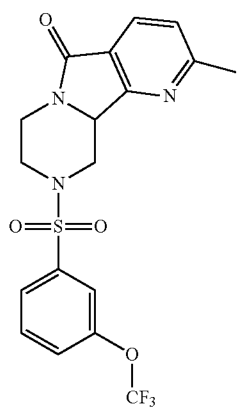 [SMILES: Cc1ccc2c(n1)C1CN(S(=O)(=O)c3cccc(OC(F)(F)F)c3)CCN1C2=O] | 2-Methyl-9-({3-[(trifluoromethyl)oxy]phenyl}sulfonyl)-8,9,10,10a-tetrahydropyrido[2',3':3,4]pyrrolo[1,2-a]pyrazin-5(7H)-one |
| 36 | 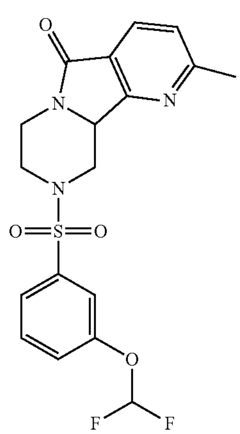 [SMILES: Cc1ccc2c(n1)C1CN(S(=O)(=O)c3cccc(OC(F)F)c3)CCN1C2=O] | 9-({3-[(Difluoromethyl)oxy]phenyl}sulfonyl)-2-methyl-8,9,10,10a-tetrahydropyrido[2',3':3,4]pyrrolo[1,2-a]pyrazin-5(7H)-one |

TABLE 2-continued
| Compound No. | Structure | Name |
|---|---|---|
| 37 | 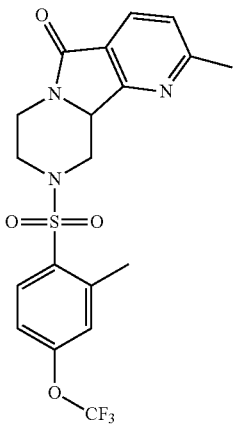 | 2-Methyl-9-({2-methyl-4-[(trifluoromethyl)oxy]phenyl}sulfonyl)-8,9,10,10a-tetrahydropyrido[2',3':3,4]pyrrolo[1,2-a]pyrazin-5(7H)-one |
| 38 | 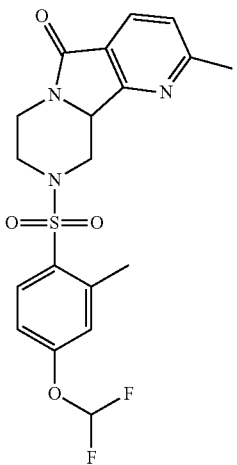 [SMILES: Cc1ccc2c(n1)C1CN(S(=O)(=O)c3ccc(OC(F)F)cc3C)CCN1C2=O] | 9-({4-[(Difluoromethyl)oxy]-2-methylphenyl}sulfonyl)-2-methyl-8,9,10,10a-tetrahydropyrido[2',3':3,4]pyrrolo[1,2-a]pyrazin-5(7H)-one |
| 39 | 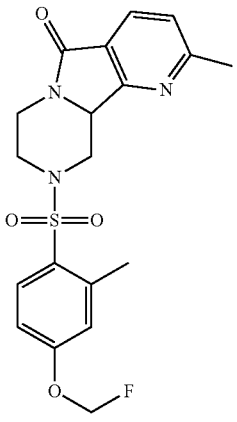 | 9-({4-[(Fluoromethyl)oxy]-2-methylphenyl}sulfonyl)-2-methyl-8,9,10,10a-tetrahydropyrido[2',3':3,4]pyrrolo[1,2-a]pyrazin-5(7H)-one |

TABLE 2-continued

| Compound No. | Structure | Name |
| --- | --- | --- |
| 40 | 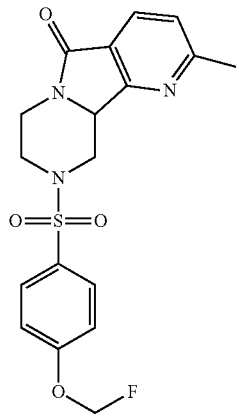 [SMILES: Cc1ccc2c(n1)C1CN(S(=O)(=O)c3ccc(OCF)cc3)CCN1C2=O] | 9-({4-[(Fluoromethyl)oxy]phenyl}sulfonyl)-2-methyl-8,9,10,10a-tetrahydropyrido[2',3':3,4]pyrrolo[1,2-a]pyrazin-5(7H)-one |
| 41 | 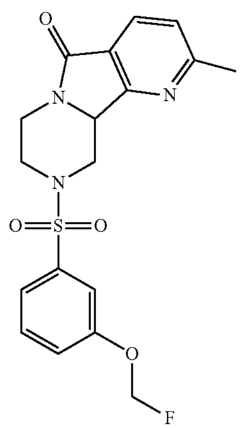 [SMILES: Cc1ccc2c(n1)C1CN(S(=O)(=O)c3cccc(OCF)c3)CCN1C2=O] | 9-({3-[(Fluoromethyl)oxy]phenyl}sulfonyl)-2-methyl-8,9,10,10a-tetrahydropyrido[2',3':3,4]pyrrolo[1,2-a]pyrazin-5(7H)-one |

TABLE 3

| Compound No. | Structure | Name |
| --- | --- | --- |
| 42 | 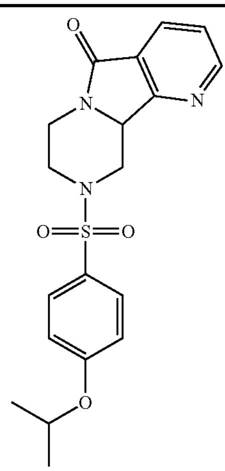 | 9-({4-[(1-Methylethyl)oxy]phenyl}-sulfonyl)-8,9,10,10a-tetrahydropyrido[2',3':3,4]-pyrrolo[1,2-a]pyrazin-5(7H)-one |
| 43 | | 3-[(5-Oxo-7,8,10,10a-tetrahydropyrido[2',3':3,4]-pyrrolo[1,2-a]pyrazin-9(5H)-yl)sulfonyl]-benzonitrile |

TABLE 3-continued

| Compound No. | Structure | Name |
|---|---|---|
| 44 | 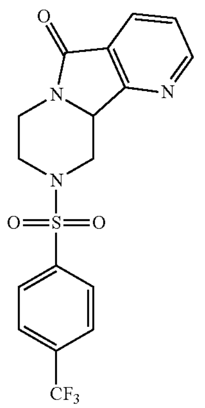 [SMILES: O=C1c2cccnc2C2CN(S(=O)(=O)c3ccc(C(F)(F)F)cc3)CCN12] | 9-{[4-(Trifluoromethyl)phenyl]sulfonyl}-8,9,10,10a-tetrahydropyrido[2',3':3,4]pyrrolo[1,2-a]pyrazin-5(7H)-one |
| 45 | 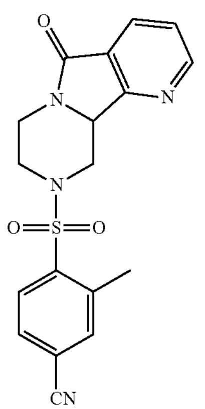 [SMILES: Cc1cc(C#N)ccc1S(=O)(=O)N1CCN2C(=O)c3cccnc3C2C1] | 3-Methyl-4-[(5-oxo-7,8,10,10a-tetrahydropyrido[2',3':3,4]pyrrolo[1,2-a]pyrazin-9(5H)-yl)sulfonyl]benzonitrile |
| 46 | 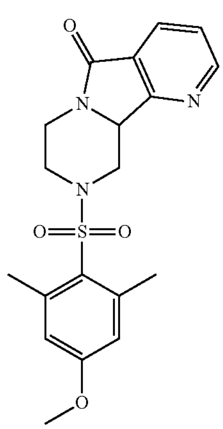 [SMILES: COc1cc(C)c(S(=O)(=O)N2CCN3C(=O)c4cccnc4C3C2)c(C)c1] | 9-{[2,6-Dimethyl-4-(methyloxy)phenyl]sulfonyl}-8,9,10,10a-tetrahydropyrido[2',3':3,4]pyrrolo[1,2-a]pyrazin-5(7H)-one |
| 47 | 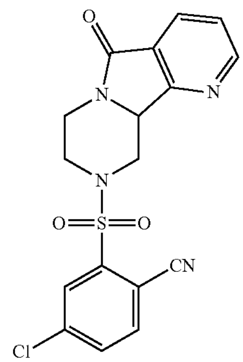 [SMILES: N#Cc1ccc(Cl)cc1S(=O)(=O)N1CCN2C(=O)c3cccnc3C2C1] | 4-Chloro-2-[(5-oxo-7,8,10,10a-tetrahydropyrido[2',3':3,4]pyrrolo[1,2-a]pyrazin-9(5H)-yl)sulfonyl]benzonitrile |
| 48 | 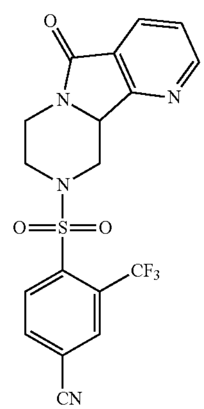 [SMILES: N#Cc1ccc(S(=O)(=O)N2CCN3C(=O)c4cccnc4C3C2)c(C(F)(F)F)c1] | 4-[(5-Oxo-7,8,10,10a-tetrahydropyrido[2',3':3,4]pyrrolo[1,2-a]pyrazin-9(5H)-yl)sulfonyl]-3-(trifluoromethyl)benzonitrile |
| 49 | 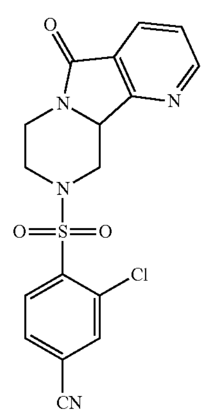 [SMILES: N#Cc1ccc(S(=O)(=O)N2CCN3C(=O)c4cccnc4C3C2)c(Cl)c1] | 3-Chloro-4-[(5-oxo-7,8,10,10a-tetrahydropyrido[2',3':3,4]pyrrolo[1,2-a]pyrazin-9(5H)-yl)sulfonyl]benzonitrile |

TABLE 3-continued

| Compound No. | Structure | Name |
|---|---|---|
| 50 | 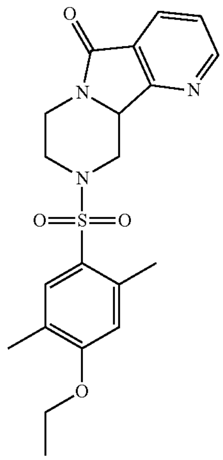 [SMILES: CCOc1cc(C)c(S(=O)(=O)N2CCN3C(=O)c4cccnc4C3C2)cc1C] | 9-{[4-(Ethyloxy)-2,5-dimethylphenyl]sulfonyl}-8,9,10,10a-tetrahydropyrido[2',3':3,4]-pyrrolo[1,2-a]pyrazin-5(7H)-one |
| 51 | 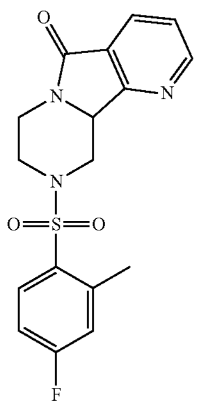 [SMILES: Cc1cc(F)ccc1S(=O)(=O)N1CCN2C(=O)c3cccnc3C2C1] | 9-[(4-Fluoro-2-methylphenyl)-sulfonyl]-8,9,10,10a-tetrahydropyrido[2',3':3,4]-pyrrolo[1,2-a]pyrazin-5(7H)-one |
| 52 | 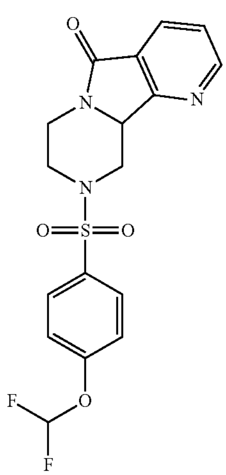 [SMILES: O=C1c2cccnc2C2CN(S(=O)(=O)c3ccc(OC(F)F)cc3)CCN12] | 9-({4-[(Difluoromethy)oxy]phenyl}-sulfonyl)-8,9,10,10a-tetrahydropyrido[2',3':3,4]-pyrrolo[1,2-a]pyrazin-5(7H)-one |
| 53 | | 9-({4-[(Trifluoromethyl)oxy]phenyl}-sulfonyl)-8,9,10,10a-tetrahydropyrido[2',3':3,4]-pyrrolo[1,2-a]pyrazin-5(7H)-one |
| 54 | | 3,5-Dimethyl-4-[(5-oxo-7,8,10,10a-tetrahydropyrido[2',3':3,4]-pyrrolo[1,2-a]pyrazin-9(5H)-yl)sulfonyl]-benzonitrile |
| 55 | | 2,6-Dimethyl-4-[(5-oxo-7,8,10,10a-tetrahydropyrido[2',3':3,4]-pyrrolo[1,2-a]pyrazin-9(5H)-yl)sulfonyl]-benzonitrile |

TABLE 3-continued

| Compound No. | Structure | Name |
|---|---|---|
| 56 | 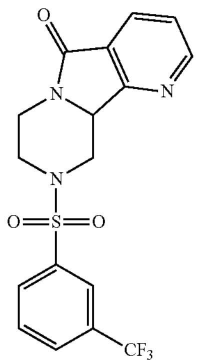 [SMILES: O=C1c2cccnc2C2CN(S(=O)(=O)c3cccc(C(F)(F)F)c3)CCN12] | 9-{[3-(Trifluoromethyl)phenyl]sulfonyl}-8,9,10,10a-tetrahydropyrido[2',3':3,4]pyrrolo[1,2-a]pyrazin-5(7H)-one |
| 57 | 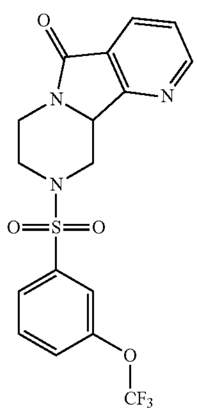 [SMILES: O=C1c2cccnc2C2CN(S(=O)(=O)c3cccc(OC(F)(F)F)c3)CCN12] | 9-({3-[(Trifluoromethyl)oxy]phenyl}sulfonyl)-8,9,10,10a-tetrahydropyrido[2',3':3,4]pyrrolo[1,2-a]pyrazin-5(7H)-one |
| 58 | 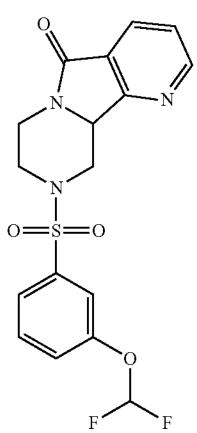 [SMILES: O=C1c2cccnc2C2CN(S(=O)(=O)c3cccc(OC(F)F)c3)CCN12] | 9-({3-[(Difluoromethyl)oxy]phenyl}sulfonyl)-8,9,10,10a-tetrahydropyrido[2',3':3,4]pyrrolo[1,2-a]pyrazin-5(7H)-one |
| 59 | | 9-({2-Methyl-4-[(trifluoromethyl)oxy]phenyl}sulfonyl)-8,9,10,10a-tetrahydropyrido[2',3':3,4]pyrrolo[1,2-a]pyrazin-5(7H)-one |
| 60 | | 9-({4-[(Difluoromethyl)oxy]-2-methylphenyl}sulfonyl)-8,9,10,10a-tetrahydropyrido[2',3':3,4]pyrrolo[1,2-a]pyrazin-5(7H)-one |
| 61 | | 9-({4-[(Fluoromethyl)oxy]-2-methylphenyl}sulfonyl)-8,9,10,10a-tetrahydropyrido[2',3':3,4]pyrrolo[1,2-a]pyrazin-5(7H)-one |

TABLE 3-continued

| Compound No. | Structure | Name |
|---|---|---|
| 62 | 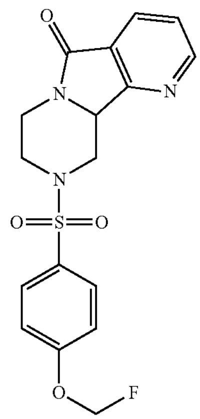 [SMILES: O=C1c2cccnc2C2CN(S(=O)(=O)c3ccc(OCF)cc3)CCN12] | 9-({4-[(Fluoromethyl)oxy]phenyl}sulfonyl)-8,9,10,10a-tetrahydropyrido[2',3':3,4]pyrrolo[1,2-a]pyrazin-5(7H)-one |
| 63 | 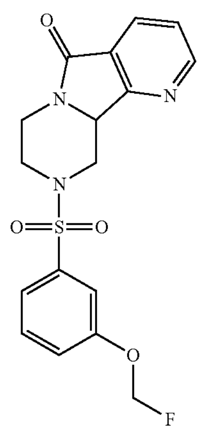 [SMILES: O=C1c2cccnc2C2CN(S(=O)(=O)c3cccc(OCF)c3)CCN12] | 9-({3-[(Fluoromethyl)oxy]phenyl}sulfonyl)-8,9,10,10a-tetrahydropyrido[2',3':3,4]pyrrolo[1,2-a]pyrazin-5(7H)-one |

TABLE 4

| Compound No. | Structure | Name |
|---|---|---|
| 64 | 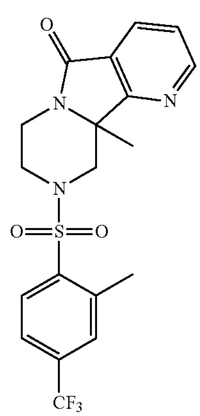 [SMILES: Cc1cc(C(F)(F)F)ccc1S(=O)(=O)N1CCN2C(=O)c3cccnc3C2(C)C1] | 10a-Methyl-9-{[2-methyl-4-(trifluoromethyl)phenyl]sulfonyl}-8,9,10,10a-tetrahydropyrido[2',3':3,4]pyrrolo[1,2-a]pyrazin-5(7H)-one |

TABLE 4-continued

| Compound No. | Structure | Name |
|---|---|---|
| 65 | 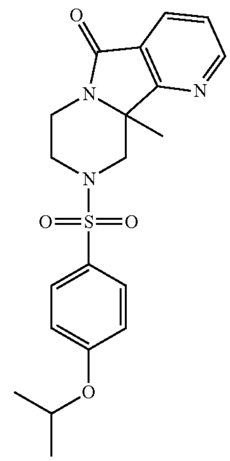 [SMILES: CC(C)Oc1ccc(S(=O)(=O)N2CCN3C(=O)c4cccnc4C3(C)C2)cc1] | 10a-Methyl-9-({4-[(1-methylethyl)oxy]phenyl}sulfonyl)-8,9,10,10a-tetrahydropyrido[2',3':3,4]pyrrolo[1,2-a]pyrazin-5(7H)-one |
| 66 | 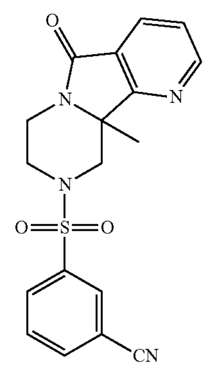 [SMILES: CC12CN(S(=O)(=O)c3cccc(C#N)c3)CCN1C(=O)c1cccnc12] | 3-[(10a-Methyl-5-oxo-7,8,10,10a-tetrahydropyrido[2',3':3,4]pyrrolo[1,2-a]pyrazin-9(5H)-yl)sulfonyl]benzonitrile |
| 67 | 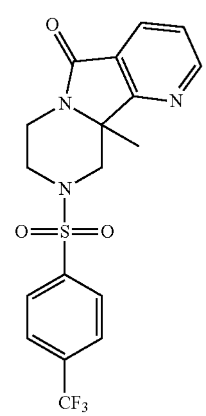 [SMILES: CC12CN(S(=O)(=O)c3ccc(C(F)(F)F)cc3)CCN1C(=O)c1cccnc12] | 10a-Methyl-9-{[4-(trifluoromethyl)phenyl]sulfonyl}-8,9,10,10a-tetrahydropyrido[2',3':3,4]pyrrolo[1,2-a]pyrazin-5(7H)-one |

TABLE 4-continued

| Compound No. | Structure | Name |
|---|---|---|
| 68 | 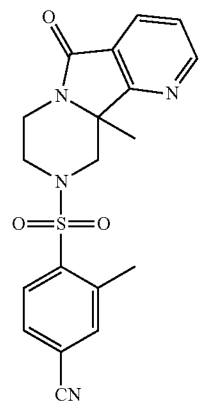 [SMILES: Cc1cc(C#N)ccc1S(=O)(=O)N1CCN2C(=O)c3cccnc3C2(C)C1] | 3-Methyl-4-[(10a-methyl-5-oxo-7,8,10,10a-tetrahydropyrido[2',3':3,4]-pyrrolo[1,2-a]pyrazin-9(5H)-yl)sulfonyl]-benzonitrile |
| 69 | 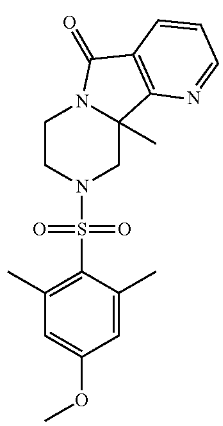 [SMILES: COc1cc(C)c(S(=O)(=O)N2CCN3C(=O)c4cccnc4C3(C)C2)c(C)c1] | 9-{[2,6-Dimethyl-4-(methyloxy)phenyl]sulfonyl}-10a-methyl-8,9,10,10a-tetrahydropyrido[2',3':3,4]-pyrrolo[1,2-a]pyrazin-5(7H)-one |
| 70 | 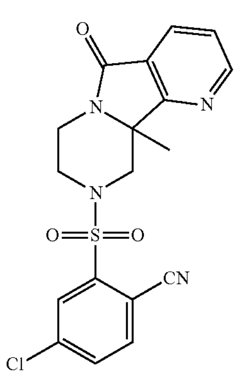 [SMILES: CC12CN(S(=O)(=O)c3cc(Cl)ccc3C#N)CCN1C(=O)c1cccnc12] | 4-Chloro-2-[(10a-methyl-5-oxo-7,8,10,10a-tetrahydropyrido[2',3':3,4]-pyrrolo[1,2-a]pyrazin-9(5H)-yl)sulfonyl]-benzonitrile |
| 71 | | 4-[(10a-Methyl-5-oxo-7,8,10,10a-tetrahydropyrido[2',3':3,4]-pyrrolo[1,2-a]pyrazin-9(5H)-yl)sulfonyl]-3-(trifluoromethyl)benzonitrile |
| 72 | | 3-Chloro-4-[(10a-methyl-5-oxo-7,8,10,10a-tetrahydropyrido[2',3':3,4]-pyrrolo[1,2-a]pyrazin-9(5H)-yl)sulfonyl]-benzonitrile |
| 73 | | 9-{[4-(Ethyloxy)-2,5-dimethylphenyl]sulfonyl}-10a-methyl-8,9,10,10a-tetrahydropyrido[2',3':3,4]-pyrrolo[1,2-a]pyrazin-5(7H)-one |

TABLE 4-continued

| Compound No. | Structure | Name |
|---|---|---|
| 74 | | 9-[(4-Fluoro-2-methylphenyl)-sulfonyl]-10a-methyl-8,9,10,10a-tetrahydropyrido[2',3':3,4]-pyrrolo[1,2-a]pyrazin-5(7H)-one |
| 75 | | 9-({4-[(Difluoromethyl)oxy]phenyl}-sulfonyl)-10a-methyl-8,9,10,10a-tetrahydropyrido[2',3':3,4]-pyrrolo[1,2-a]pyrazin-5(7H)-one |
| 76 | | 10a-Methyl-9-({4-[(trifluoromethyl)oxy]-phenyl}sulfonyl)-8,9,10,10a-tetrahydropyrido[2',3':3,4]-pyrrolo[1,2-a]pyrazin-5(7H)-one |
| 77 | 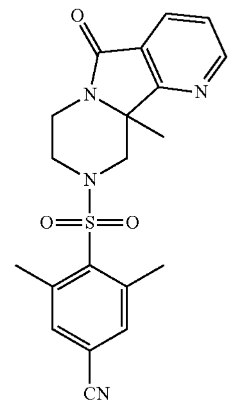 [SMILES: Cc1cc(C#N)cc(C)c1S(=O)(=O)N1CCN2C(=O)c3cccnc3C2(C)C1] | 3,5-Dimethyl-4-[(10a-methyl-5-oxo-7,8,10,10a-tetrahydropyrido[2',3':3,4]-pyrrolo[1,2-a]pyrazin-9(5H)-yl)sulfonyl]-benzonitrile |
| 78 | 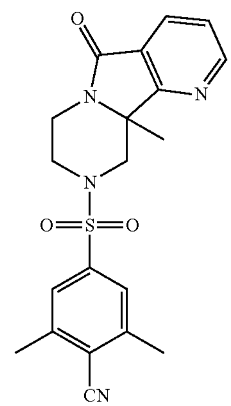 [SMILES: Cc1cc(S(=O)(=O)N2CCN3C(=O)c4cccnc4C3(C)C2)cc(C)c1C#N] | 2,6-Dimethyl-4-[(10a-methyl-5-oxo-7,8,10,10a-tetrahydropyrido[2',3':3,4]-pyrrolo[1,2-a]pyrazin-9(5H)-yl)sulfonyl]-benzonitrile |
| 79 | 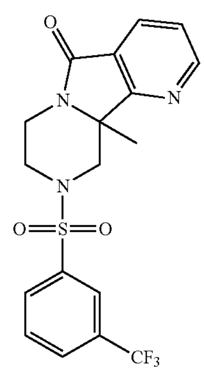 [SMILES: CC12CN(S(=O)(=O)c3cccc(C(F)(F)F)c3)CCN1C(=O)c1cccnc12] | 10a-Methyl-9-{[3-(trifluoromethyl)phenyl]-sulfonyl}-8,9,10,10a-tetrahydropyrido[2',3':3,4]-pyrrolo[1,2-a]pyrazin-5(7H)-one |
| 80 | 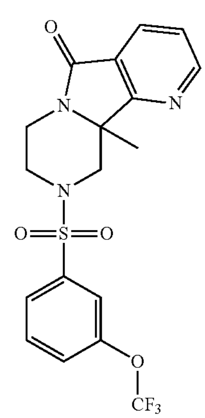 [SMILES: CC12CN(S(=O)(=O)c3cccc(OC(F)(F)F)c3)CCN1C(=O)c1cccnc12] | 10a-Methyl-9-({3-[(trifluoromethyl)oxy]phenyl}-sulfonyl)-8,9,10,10a-tetrahydropyrido[2',3':3,4]-pyrrolo[1,2-a]pyrazin-5(7H)-one |

TABLE 4-continued

| Compound No. | Structure | Name |
|---|---|---|
| 81 | 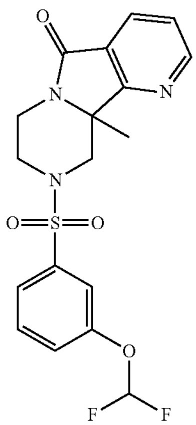 [SMILES: CC12CN(S(=O)(=O)c3cccc(OC(F)F)c3)CCN1C(=O)c1cccnc12] | 9-({3-[(Difluoromethyl)oxy]-phenyl}sulfonyl)-10a-methyl-8,9,10,10a-tetrahydropyrido[2',3':3,4]-pyrrolo[1,2-a]pyrazin-5(7H)-one |
| 82 | 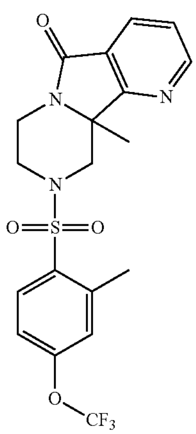 [SMILES: Cc1cc(OC(F)(F)F)ccc1S(=O)(=O)N1CCN2C(=O)c3cccnc3C2(C)C1] | 10a-Methyl-9-({2-methyl-4-[(trifluoromethyl)oxy]-phenyl}sulfonyl)-8,9,10,10a-tetrahydropyrido[2',3':3,4]-pyrrolo[1,2-a]pyrazin-5(7H)-one |
| 83 | 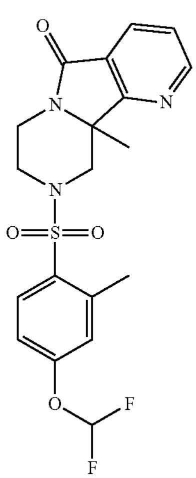 [SMILES: Cc1cc(OC(F)F)ccc1S(=O)(=O)N1CCN2C(=O)c3cccnc3C2(C)C1] | 9-({4-[(Difluoromethyl)oxy]-2-methylphenyl}sulfonyl)-10a-methyl-8,9,10,10a-tetrahydropyrido[2',3':3,4]-pyrrolo[1,2-a]pyrazin-5(7H)-one |
| 84 | 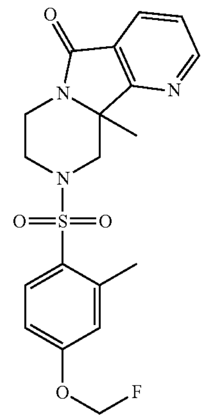 [SMILES: Cc1cc(OCF)ccc1S(=O)(=O)N1CCN2C(=O)c3cccnc3C2(C)C1] | 9-({4-[(Fluoromethyl)oxy]-2-methylphenyl}sulfonyl)-10a-methyl-8,9,10,10a-tetrahydropyrido[2',3':3,4]-pyrrolo[1,2-a]pyrazin-5(7H)-one |
| 85 | 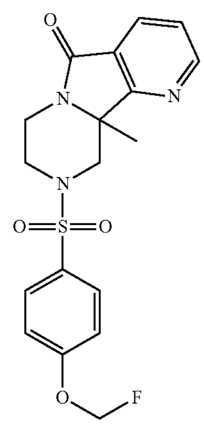 [SMILES: CC12CN(S(=O)(=O)c3ccc(OCF)cc3)CCN1C(=O)c1cccnc12] | 9-({4-[(Fluoromethyl)oxy]phenyl}-sulfonyl)-10a-methyl-8,9,10,10a-tetrahydropyrido[2',3':3,4]-pyrrolo[1,2-a]pyrazin-5(7H)-one |
| 86 | 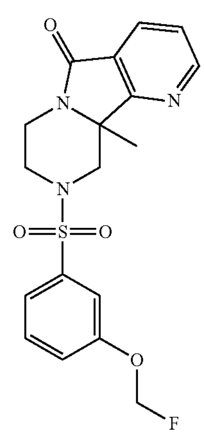 [SMILES: CC12CN(S(=O)(=O)c3cccc(OCF)c3)CCN1C(=O)c1cccnc12] | 9-({3-[(Fluoromethyl)oxy]phenyl}-sulfonyl)-10a-methyl-8,9,10,10a-tetrahydropyrido[2',3':3,4]-pyrrolo[1,2-a]pyrazin-5(7H)-one |

TABLE 5

| Compound No. | Structure | Name |
|---|---|---|
| 87 | 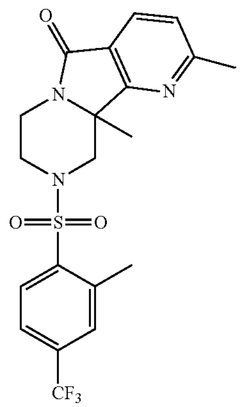 [SMILES: Cc1ccc2c(n1)C1(C)CN(S(=O)(=O)c3ccc(C(F)(F)F)cc3C)CCN1C2=O] | 2,10a-Dimethyl-9-{[2-methyl-4-(trifluoromethyl)phenyl]sulfonyl}-8,9,10,10a-tetrahydropyrido[2',3':3,4]pyrrolo[1,2-a]pyrazin-5(7H)-one |
| 88 | 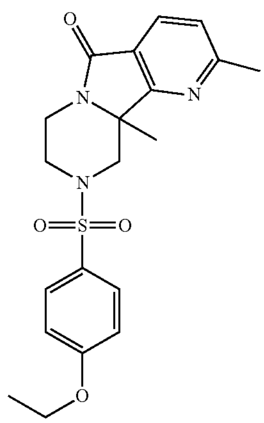 [SMILES: CCOc1ccc(S(=O)(=O)N2CCN3C(=O)c4ccc(C)nc4C3(C)C2)cc1] | 9-{[4-(Ethyloxy)phenyl]sulfonyl}-2,10a-dimethyl-8,9,10,10a-tetrahydropyrido[2',3':3,4]pyrrolo[1,2-a]pyrazin-5(7H)-one |
| 89 | 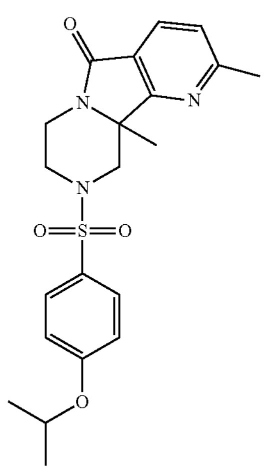 [SMILES: Cc1ccc2c(n1)C1(C)CN(S(=O)(=O)c3ccc(OC(C)C)cc3)CCN1C2=O] | 2,10a-Dimethyl-9-({4-[(1-methylethyl)oxy]phenyl}sulfonyl)-8,9,10,10a-tetrahydropyrido[2',3':3,4]pyrrolo[1,2-a]pyrazin-5(7H)-one |

TABLE 5-continued

| Compound No. | Structure | Name |
|---|---|---|
| 90 | 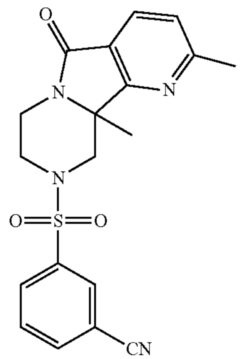 [SMILES: Cc1ccc2c(n1)C1(C)CN(S(=O)(=O)c3cccc(C#N)c3)CCN1C2=O] | 3-[(2,10a-Dimethyl-5-oxo-7,8,10,10a-tetrahydropyrido[2',3':3,4]pyrrolo[1,2-a]pyrazin-9(5H)-yl)sulfonyl]benzonitrile |
| 91 | 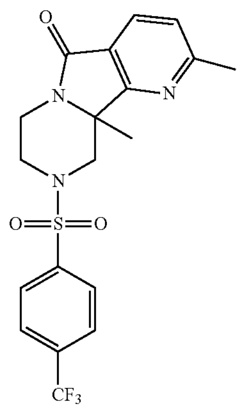 [SMILES: Cc1ccc2c(n1)C1(C)CN(S(=O)(=O)c3ccc(C(F)(F)F)cc3)CCN1C2=O] | 2,10a-Dimethyl-9-{[4-(trifluoromethyl)phenyl]sulfonyl}-8,9,10,10a-tetrahydropyrido[2',3':3,4]pyrrolo[1,2-a]pyrazin-5(7H)-one |
| 92 | 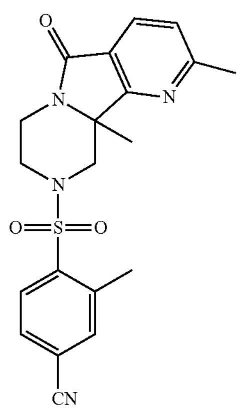 [SMILES: Cc1ccc2c(n1)C1(C)CN(S(=O)(=O)c3ccc(C#N)cc3C)CCN1C2=O] | 4-[(2,10a-Dimethyl-5-oxo-7,8,10,10a-tetrahydropyrido[2',3':3,4]pyrrolo[1,2-a]pyrazin-9(5H)-yl)sulfonyl]-3-methylbenzonitrile |
| 93 | 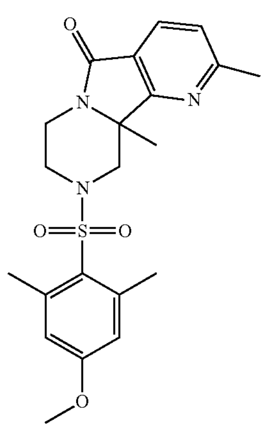 | 9-{[2,6-Dimethyl-4-(methyloxy)phenyl]sulfonyl}-2,10a-dimethyl-8,9,10,10a-tetrahydropyrido[2',3':3,4]pyrrolo[1,2-a]pyrazin-5(7H)-one |

TABLE 5-continued

| Compound No. | Structure | Name |
|---|---|---|
| 94 | 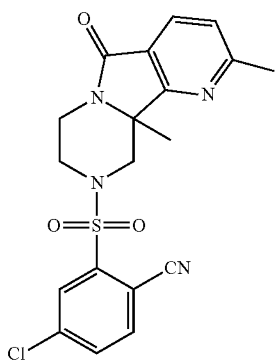 [SMILES: Cc1ccc2c(n1)C1(C)CN(S(=O)(=O)c3cc(Cl)ccc3C#N)CCN1C2=O] | 4-Chloro-2-[(2,10a-dimethyl-5-oxo-7,8,10,10a-tetrahydropyrido[2',3':3,4]pyrrolo[1,2-a]pyrazin-9(5H)-yl)sulfonyl]benzonitrile |
| 95 | 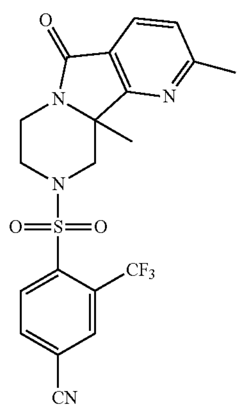 [SMILES: Cc1ccc2c(n1)C1(C)CN(S(=O)(=O)c3ccc(C#N)cc3C(F)(F)F)CCN1C2=O] | 4-[(2,10a-Dimethyl-5-oxo-7,8,10,10a-tetrahydropyrido[2',3':3,4]pyrrolo[1,2-a]pyrazin-9(5H)-yl)sulfonyl]-3-(trifluoromethyl)benzonitrile |
| 96 | 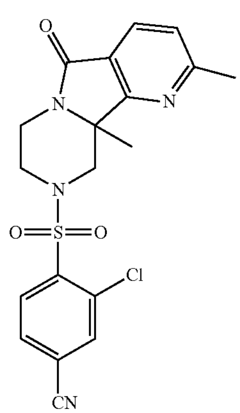 [SMILES: Cc1ccc2c(n1)C1(C)CN(S(=O)(=O)c3ccc(C#N)cc3Cl)CCN1C2=O] | 3-Chloro-4-[(2,10a-dimethyl-5-oxo-7,8,10,10a-tetrahydropyrido[2',3':3,4]pyrrolo[1,2-a]pyrazin-9(5H)-yl)sulfonyl]benzonitrile |

TABLE 5-continued

| Compound No. | Structure | Name |
|---|---|---|
| 97 | 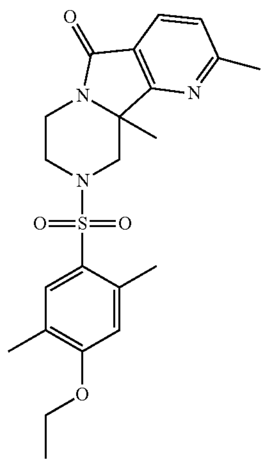 | 9-{[4-(Ethyloxy)-2,5-dimethylphenyl]sulfonyl}-2,10a-dimethyl-8,9,10,10a-tetrahydropyrido[2',3':3,4]pyrrolo[1,2-a]pyrazin-5(7H)-one |
| 98 | 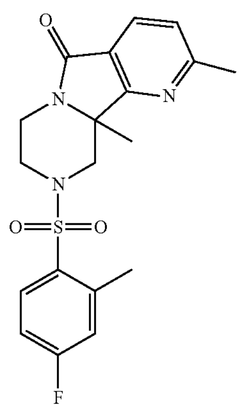 [SMILES: Cc1ccc2c(n1)C1(C)CN(S(=O)(=O)c3ccc(F)cc3C)CCN1C2=O] | 9-[(4-Fluoro-2-methylphenyl)sulfonyl]-2,10a-dimethyl-8,9,10,10a-tetrahydropyrido[2',3':3,4]pyrrolo[1,2-a]pyrazin-5(7H)-one |
| 99 | 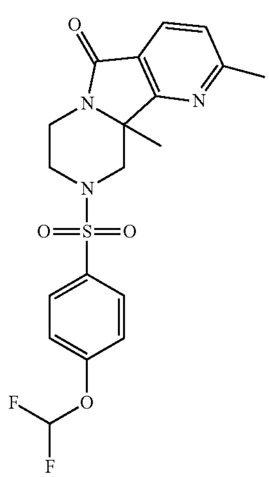 [SMILES: Cc1ccc2c(n1)C1(C)CN(S(=O)(=O)c3ccc(OC(F)F)cc3)CCN1C2=O] | 9-({4-[(Difluoromethyl)oxy]phenyl}sulfonyl)-2,10a-dimethyl-8,9,10,10a-tetrahydropyrido[2',3':3,4]pyrrolo[1,2-a]pyrazin-5(7H)-one |

TABLE 5-continued

| Compound No. | Structure | Name |
|---|---|---|
| 100 | 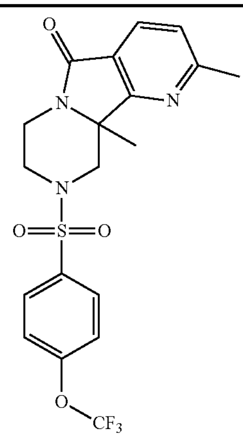 | 2,10a-Dimethyl-9-({4-[(trifluoromethyl)oxy]phenyl}sulfonyl)-8,9,10,10a-tetrahydropyrido[2',3':3,4]pyrrolo[1,2-a]pyrazin-5(7H)-one |
| 101 | 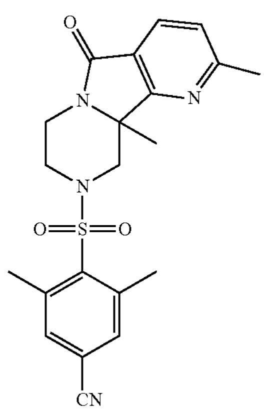 | 4-[(2,10a-Dimethyl-5-oxo-7,8,10,10a-tetrahydropyrido[2',3':3,4]pyrrolo[1,2-a]pyrazin-9(5H)-yl)sulfonyl]-3,5-dimethylbenzonitrile |
| 102 | 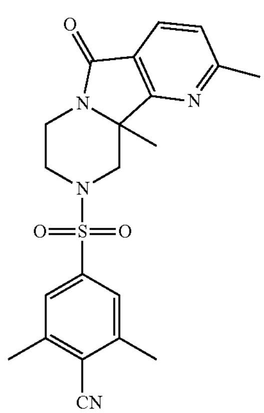 | 4-[(2,10a-Dimethyl-5-oxo-7,8,10,10a-tetrahydropyrido[2',3':3,4]pyrrolo[1,2-a]pyrazin-9(5H)-yl)sulfonyl]-2,6-dimethylbenzonitrile |
| 103 | 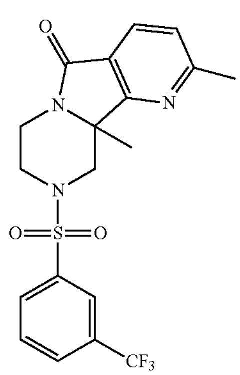 [SMILES: Cc1ccc2c(n1)C1(C)CN(S(=O)(=O)c3cccc(C(F)(F)F)c3)CCN1C2=O] | 2,10a-Dimethyl-9-{[3-(trifluoromethyl)phenyl]sulfonyl}-8,9,10,10a-tetrahydropyrido[2',3':3,4]pyrrolo[1,2-a]pyrazin-5(7H)-one |

TABLE 5-continued

| Compound No. | Structure | Name |
|---|---|---|
| 104 | 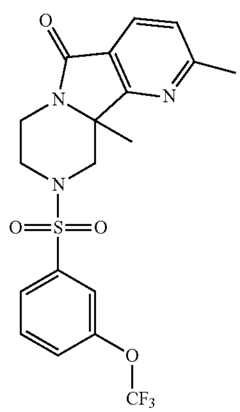 [SMILES: Cc1ccc2c(n1)C1(C)CN(S(=O)(=O)c3cccc(OC(F)(F)F)c3)CCN1C2=O] | 2,10a-Dimethyl-9-({3-[(trifluoromethyl)oxy]phenyl}sulfonyl)-8,9,10,10a-tetrahydropyrido[2',3':3,4]pyrrolo[1,2-a]pyrazin-5(7H)-one |
| 105 | 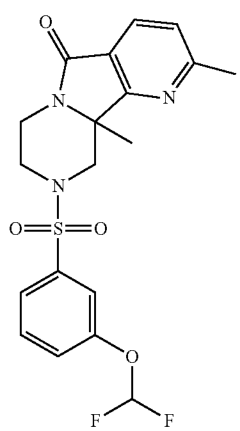 [SMILES: Cc1ccc2c(n1)C1(C)CN(S(=O)(=O)c3cccc(OC(F)F)c3)CCN1C2=O] | 9-({3-[(Difluoromethyl)oxy]phenyl}sulfonyl)-2,10a-dimethyl-8,9,10,10a-tetrahydropyrido[2',3':3,4]pyrrolo[1,2-a]pyrazin-5(7H)-one |
| 106 | 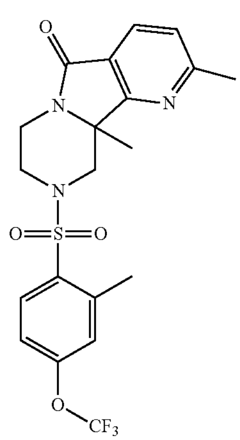 [SMILES: Cc1ccc2c(n1)C1(C)CN(S(=O)(=O)c3ccc(OC(F)(F)F)cc3C)CCN1C2=O] | 2,10a-Dimethyl-9-({2-methyl-4-[(trifluoromethyl)oxy]phenyl}sulfonyl)-8,9,10,10a-tetrahydropyrido[2',3':3,4]pyrrolo[1,2-a]pyrazin-5(7H)-one |

TABLE 5-continued

| Compound No. | Structure | Name |
|---|---|---|
| 107 | 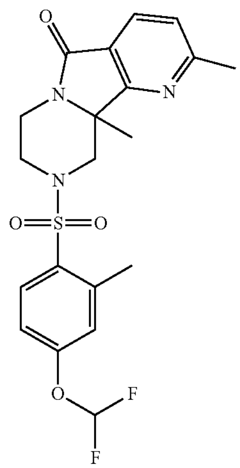 [SMILES: Cc1ccc2c(n1)C1(C)CN(S(=O)(=O)c3ccc(OC(F)F)cc3C)CCN1C2=O] | 9-({4-[(Difluoromethyl)oxy]-2-methylphenyl}sulfonyl)-2,10a-dimethyl-8,9,10,10a-tetrahydropyrido[2',3':3,4]pyrrolo[1,2-a]pyrazin-5(7H)-one |
| 108 | 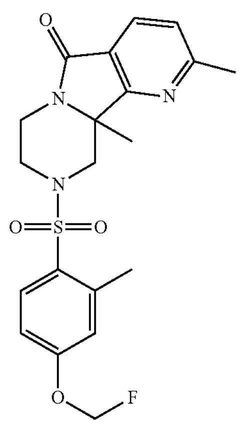 [SMILES: Cc1ccc2c(n1)C1(C)CN(S(=O)(=O)c3ccc(OCF)cc3C)CCN1C2=O] | 9-({4-[(Fluoromethyl)oxy]-2-methylphenyl}sulfonyl)-2,10a-dimethyl-8,9,10,10a-tetrahydropyrido[2',3':3,4]pyrrolo[1,2-a]pyrazin-5(7H)-one |
| 109 | 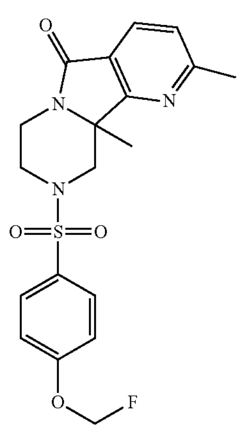 [SMILES: Cc1ccc2c(n1)C1(C)CN(S(=O)(=O)c3ccc(OCF)cc3)CCN1C2=O] | 9-({4-[(Fluoromethyl)oxy]phenyl}sulfonyl)-2,10a-dimethyl-8,9,10,10a-tetrahydropyrido[2',3':3,4]pyrrolo[1,2-a]pyrazin-5(7H)-one |

TABLE 5-continued

| Compound No. | Structure | Name |
|---|---|---|
| 110 | 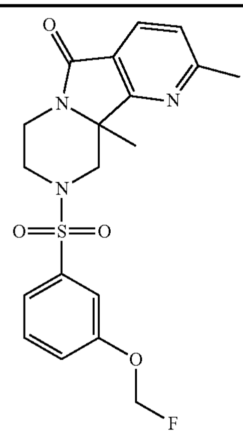 | 9-({3-[(Fluoromethyl)oxy]phenyl}sulfonyl)-2,10a-dimethyl-8,9,10,10a-tetrahydropyrido[2',3':3,4]pyrrolo[1,2-a]pyrazin-5(7H)-one |

TABLE 6

| Compound No. | Structure | Name |
|---|---|---|
| 111 | 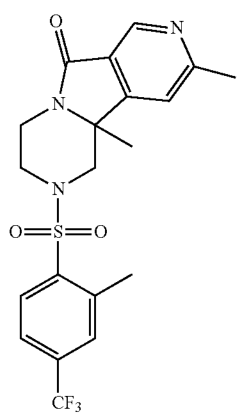 | 9,10b-Dimethyl-2-{[2-methyl-4-(trifluoromethyl)phenyl]sulfonyl}-1,3,4,10b-tetrahydropyrido[4',3':3,4]pyrrolo[1,2-a]pyrazin-6(2H)-one |
| 112 | 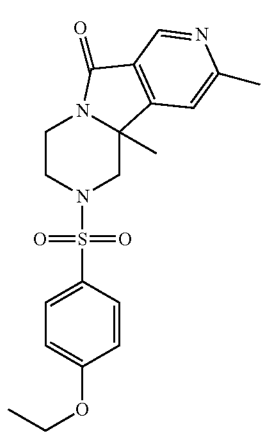 [SMILES: CCOc1ccc(S(=O)(=O)N2CCN3C(=O)c4cnc(C)cc4C3(C)C2)cc1] | 2-{[4-(Ethyloxy)phenyl]sulfonyl}-9,10b-dimethyl-1,3,4,10b-tetrahydropyrido[4',3':3,4]pyrrolo[1,2-a]pyrazin-6(2H)-one |

TABLE 6-continued

| Compound No. | Structure | Name |
|---|---|---|
| 113 | 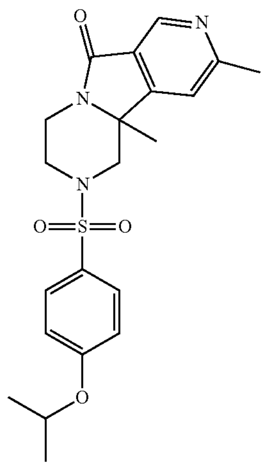 [SMILES: Cc1cc2c(cn1)C(=O)N1CCN(S(=O)(=O)c3ccc(OC(C)C)cc3)CC21C] | 9,10b-Dimethyl-2-({4-[(1-methylethyl)oxy]phenyl}sulfonyl)-1,3,4,10b-tetrahydropyrido[4',3':3,4]pyrrolo[1,2-a]pyrazin-6(2H)-one |
| 114 | 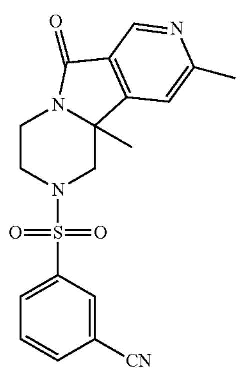 [SMILES: Cc1cc2c(cn1)C(=O)N1CCN(S(=O)(=O)c3cccc(C#N)c3)CC21C] | 3-[(9,10b-Dimethyl-6-oxo-3,4,6,10b-tetrahydropyrido[4',3':3,4]pyrrolo[1,2-a]pyrazin-2(1H)-yl)sulfonyl]benzonitrile |
| 115 | 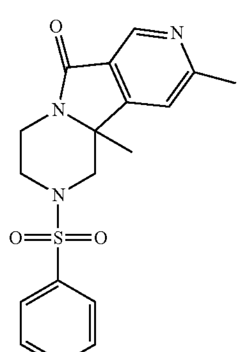 | 9,10b-Dimethyl-2-{[4-(trifluoromethyl)phenyl]sulfonyl}-1,3,4,10b-tetrahydropyrido[4',3':3,4]pyrrolo[1,2-a]pyrazin-6(2H)-one |

TABLE 6-continued

| Compound No. | Structure | Name |
|---|---|---|
| 116 | 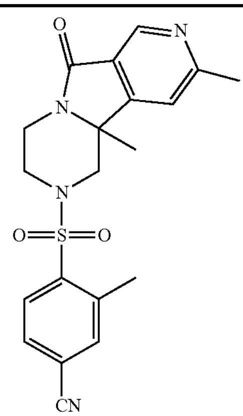 | 4-[(9,10b-Dimethyl-6-oxo-3,4,6,10b-tetrahydropyrido[4',3':3,4]pyrrolo[1,2-a]pyrazin-2(1H)-yl)sulfonyl]-3-methylbenzonitrile |
| 117 | 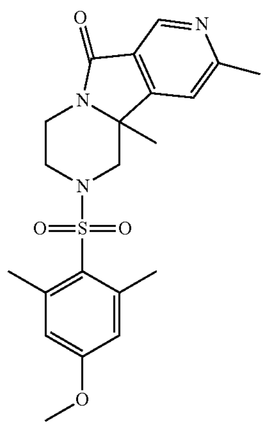 | 2-{[2,6-Dimethyl-4-(methyloxy)phenyl]sulfonyl}-9,10b-dimethyl-1,3,4,10b-tetrahydropyrido[4',3':3,4]pyrrolo[1,2-a]pyrazin-6(2H)-one |
| 118 | 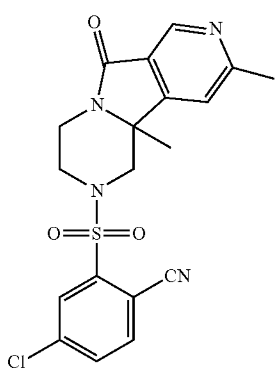 [SMILES: Cc1cc2c(cn1)C(=O)N1CCN(S(=O)(=O)c3cc(Cl)ccc3C#N)CC21C] | 4-Chloro-2-[(9,10b-dimethyl-6-oxo-3,4,6,10b-tetrahydropyrido[4',3':3,4]pyrrolo[1,2-a]pyrazin-2(1H)-yl)sulfonyl]benzonitrile |
| 119 | 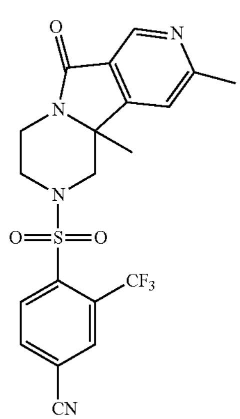 [SMILES: Cc1cc2c(cn1)C(=O)N1CCN(S(=O)(=O)c3ccc(C#N)cc3C(F)(F)F)CC21C] | 4-[(9,10b-Dimethyl-6-oxo-3,4,6,10b-tetrahydropyrido[4',3':3,4]pyrrolo[1,2-a]pyrazin-2(1H)-yl)sulfonyl]-3-(trifluoromethyl)benzonitrile |

TABLE 6-continued

| Compound No. | Structure | Name |
|---|---|---|
| 120 | 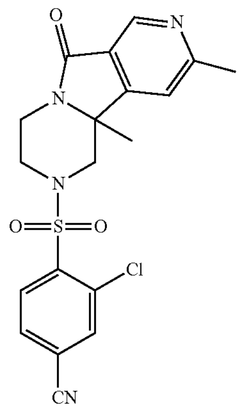 | 3-Chloro-4-[(9,10b-dimethyl-6-oxo-3,4,6,10b-tetrahydropyrido[4',3':3,4]pyrrolo[1,2-a]pyrazin-2(1H)-yl)sulfonyl]benzonitrile |
| 121 | 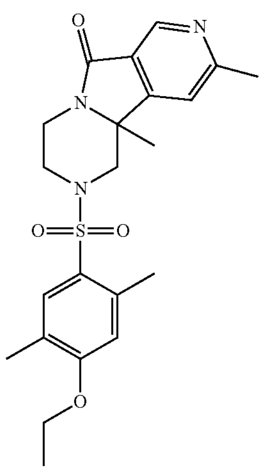 | 2-{[4-(Ethyloxy)-2,5-dimethylphenyl]sulfonyl}-9,10b-dimethyl-1,3,4,10b-tetrahydropyrido[4',3':3,4]pyrrolo[1,2-a]pyrazin-6(2H)-one |
| 122 | 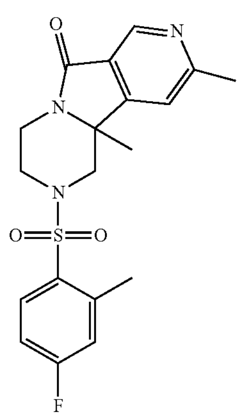 | 2-[(4-Fluoro-2-methylphenyl)sulfonyl]-9,10b-dimethyl-1,3,4,10b-tetrahydropyrido[4',3':3,4]pyrrolo[1,2-a]pyrazin-6(2H)-one |

TABLE 6-continued
| Compound No. | Structure | Name |
|---|---|---|
| 123 | 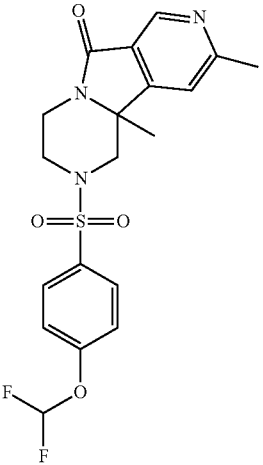 | 2-({4-[(Difluoromethyl)oxy]phenyl}sulfonyl)-9,10b-dimethyl-1,3,4,10b-tetrahydropyrido[4',3':3,4]pyrrolo[1,2-a]pyrazin-6(2H)-one |
| 124 | 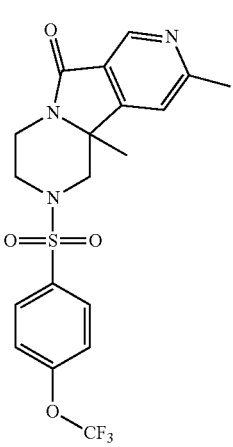 [SMILES: Cc1cc2c(cn1)C(=O)N1CCN(S(=O)(=O)c3ccc(OC(F)(F)F)cc3)CC21C] | 9,10b-Dimethyl-2-({4-[(trifluoromethyl)oxy]phenyl}sulfonyl)-1,3,4,10b-tetrahydropyrido[4',3':3,4]pyrrolo[1,2-a]pyrazin-6(2H)-one |
| 125 | 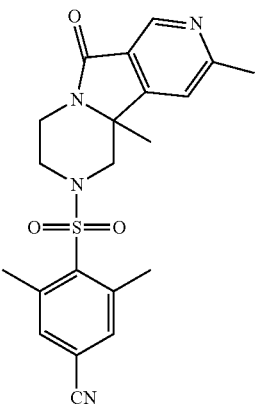 | 4-[(9,10b-Dimethyl-6-oxo-3,4,6,10b-tetrahydropyrido[4',3':3,4]pyrrolo[1,2-a]pyrazin-2(1H)-yl)sulfonyl]-3,5-dimethylbenzonitrile |

TABLE 6-continued

| Compound No. | Structure | Name |
|---|---|---|
| 126 | 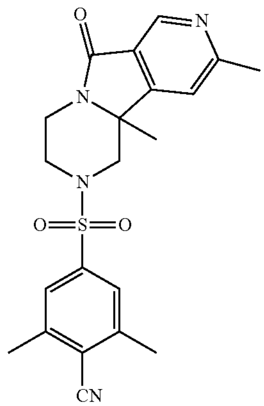 | 4-[(9,10b-Dimethyl-6-oxo-3,4,6,10b-tetrahydropyrido[4',3':3,4]pyrrolo[1,2-a]pyrazin-2(1H)-yl)sulfonyl]-2,6-dimethylbenzonitrile |
| 127 | 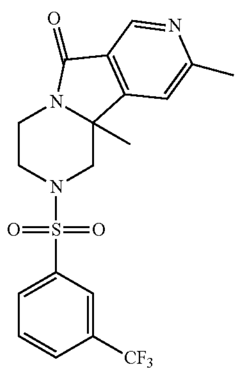 | 9,10b-Dimethyl-2-{[3-(trifluoromethyl)phenyl]sulfonyl}-1,3,4,10b-tetrahydropyrido[4',3':3,4]pyrrolo[1,2-a]pyrazin-6(2H)-one |
| 128 | 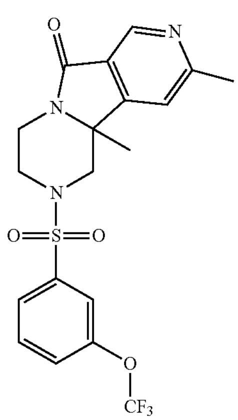 [SMILES: Cc1cc2c(cn1)C(=O)N1CCN(S(=O)(=O)c3cccc(OC(F)(F)F)c3)CC21C] | 9,10b-Dimethyl-2-({3-[(trifluoromethyl)oxy]phenyl}sulfonyl)-1,3,4,10b-tetrahydropyrido[4',3':3,4]pyrrolo[1,2-a]pyrazin-6(2H)-one |

TABLE 6-continued

| Compound No. | Structure | Name |
|---|---|---|
| 129 | 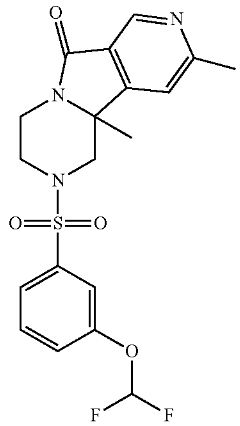 [SMILES: Cc1cc2c(cn1)C(=O)N1CCN(S(=O)(=O)c3cccc(OC(F)F)c3)CC21C] | 2-({3-[(Difluoromethyl)oxy]phenyl}sulfonyl)-9,10b-dimethyl-1,3,4,10b-tetrahydropyrido[4',3':3,4]pyrrolo[1,2-a]pyrazin-6(2H)-one |
| 130 | 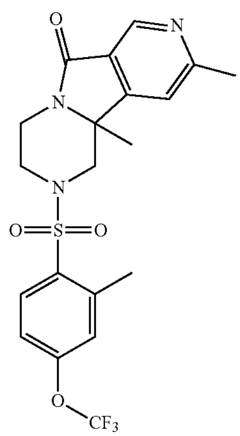 [SMILES: Cc1cc2c(cn1)C(=O)N1CCN(S(=O)(=O)c3ccc(OC(F)(F)F)cc3C)CC21C] | 9,10b-Dimethyl-2-({2-methyl-4-[(trifluoromethyl)oxy]phenyl}sulfonyl)-1,3,4,10b-tetrahydropyrido[4',3':3,4]pyrrolo[1,2-a]pyrazin-6(2H)-one |
| 131 | 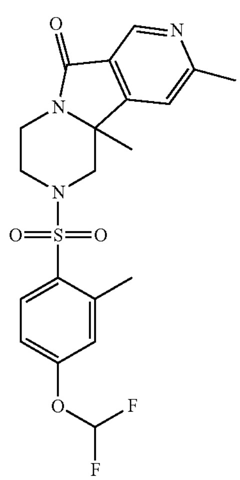 [SMILES: Cc1cc2c(cn1)C(=O)N1CCN(S(=O)(=O)c3ccc(OC(F)F)cc3C)CC21C] | 2-({4-[(Difluoromethyl)oxy]-2-methylphenyl}sulfonyl)-9,10b-dimethyl-1,3,4,10b-tetrahydropyrido[4',3':3,4]pyrrolo[1,2-a]pyrazin-6(2H)-one |

TABLE 6-continued

| Compound No. | Structure | Name |
|---|---|---|
| 132 | 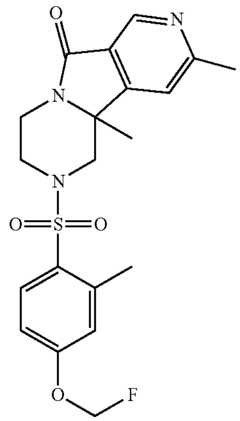 [SMILES: Cc1cc2c(cn1)C(=O)N1CCN(S(=O)(=O)c3ccc(OCF)cc3C)CC21C] | 2-({4-[(Fluoromethyl)oxy]-2-methylphenyl}sulfonyl)-9,10b-dimethyl-1,3,4,10b-tetrahydropyrido[4',3':3,4]pyrrolo[1,2-a]pyrazin-6(2H)-one |
| 133 | 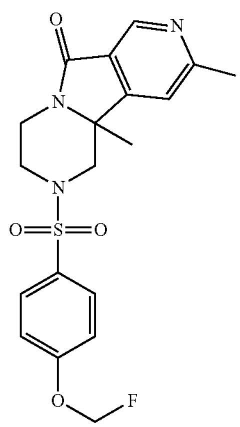 [SMILES: Cc1cc2c(cn1)C(=O)N1CCN(S(=O)(=O)c3ccc(OCF)cc3)CC21C] | 2-({4-[(Fluoromethyl)oxy]phenyl}sulfonyl)-9,10b-dimethyl-1,3,4,10b-tetrahydropyrido[4',3':3,4]pyrrolo[1,2-a]pyrazin-6(2H)-one |
| 134 | 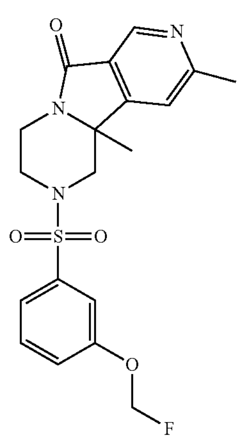 [SMILES: Cc1cc2c(cn1)C(=O)N1CCN(S(=O)(=O)c3cccc(OCF)c3)CC21C] | 2-({3-[(Fluoromethyl)oxy]phenyl}sulfonyl)-9,10b-dimethyl-1,3,4,10b-tetrahydropyrido[4',3':3,4]pyrrolo[1,2-a]pyrazin-6(2H)-one |

TABLE 7

| Compound No. | Structure | Name |
|---|---|---|
| 135 | 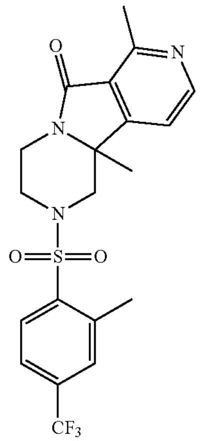 | 7,10b-Dimethyl-2-{[2-methyl-4-(trifluoromethyl)phenyl]sulfonyl}-1,3,4,10b-tetrahydropyrido[4',3':3,4]pyrrolo[1,2-a]pyrazin-6(2H)-one |
| 136 | 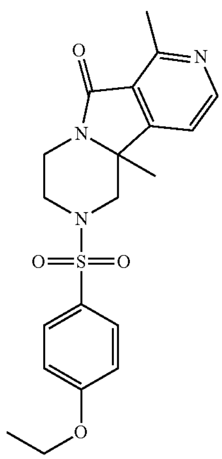 [SMILES: CCOc1ccc(S(=O)(=O)N2CCN3C(=O)c4c(ccnc4C)C3(C)C2)cc1] | 2-{[4-(Ethyloxy)phenyl]sulfonyl}-7,10b-dimethyl-1,3,4,10b-tetrahydropyrido[4',3':3,4]pyrrolo[1,2-a]pyrazin-6(2H)-one |
| 137 | 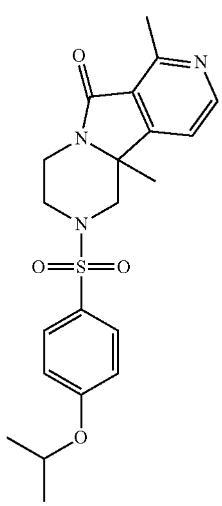 [SMILES: Cc1nccc2c1C(=O)N1CCN(S(=O)(=O)c3ccc(OC(C)C)cc3)CC21C] | 7,10b-Dimethyl-2-({4-[(1-methylethyl)oxy]phenyl}sulfonyl)-1,3,4,10b-tetrahydropyrido[4',3':3,4]pyrrolo[1,2-a]pyrazin-6(2H)-one |

TABLE 7-continued

| Compound No. | Structure | Name |
|---|---|---|
| 138 | 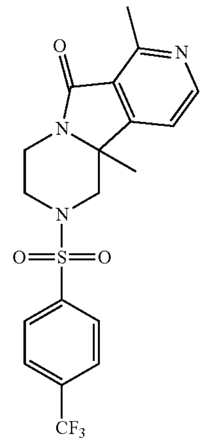 [SMILES: Cc1nccc2c1C(=O)N1CCN(S(=O)(=O)c3ccc(C(F)(F)F)cc3)CC21C] | 7,10b-Dimethyl-2-{[4-(trifluoromethyl)phenyl]sulfonyl}-1,3,4,10b-tetrahydropyrido[4',3':3,4]pyrrolo[1,2-a]pyrazin-6(2H)-one |
| 139 | 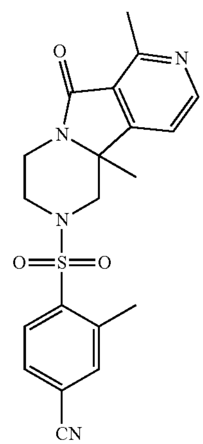 | 4-[(7,10b-Dimethyl-6-oxo-3,4,6,10b-tetrahydropyrido[4',3':3,4]pyrrolo[1,2-a]pyrazin-2(1H)-yl)sulfonyl]-3-methylbenzonitrile |
| 140 | 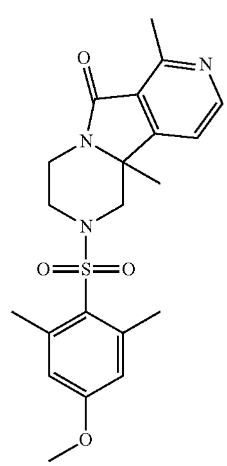 | 4-[(7,10b-Dimethyl-6-oxo-3,4,6,10b-tetrahydropyrido[4',3':3,4]pyrrolo[1,2-a]pyrazin-2(1H)-yl)sulfonyl]-3-methylbenzonitrile |

TABLE 7-continued

| Compound No. | Structure | Name |
|---|---|---|
| 141 | 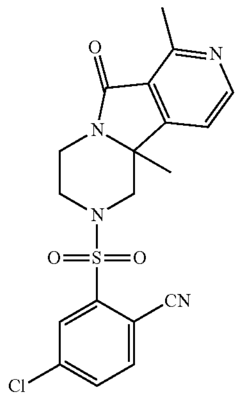 [SMILES: Cc1nccc2c1C(=O)N1CCN(S(=O)(=O)c3cc(Cl)ccc3C#N)CC21C] | 4-Chloro-2-[(7,10b-dimethyl-6-oxo-3,4,6,10b-tetrahydropyrido[4',3':3,4]pyrrolo[1,2-a]pyrazin-2(1H)-yl)sulfonyl]benzonitrile |
| 142 | 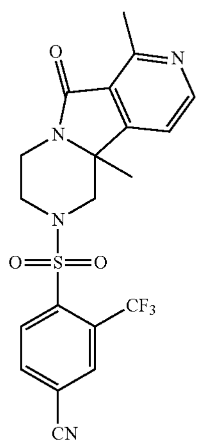 | 4-[(7,10b-Dimethyl-6-oxo-3,4,6,10b-tetrahydropyrido[4',3':3,4]pyrrolo[1,2-a]pyrazin-2(1H)-yl)sulfonyl]-3-(trifluoromethyl)benzonitrile |
| 143 | 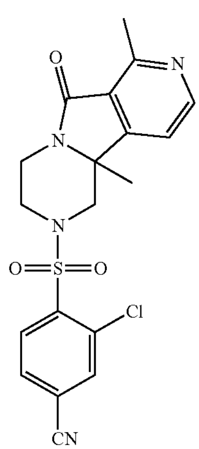 [SMILES: Cc1nccc2c1C(=O)N1CCN(S(=O)(=O)c3ccc(C#N)cc3Cl)CC21C] | 3-Chloro-4-[(7,10b-dimethyl-6-oxo-3,4,6,10b-tetrahydropyrido[4',3':3,4]pyrrolo[1,2-a]pyrazin-2(1H)-yl)sulfonyl]benzonitrile |
| 144 | 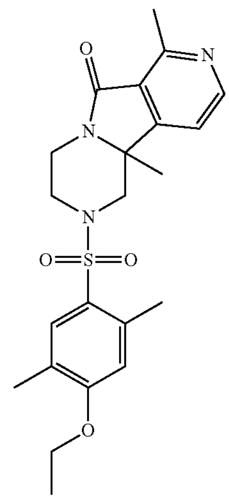 [SMILES: CCOc1cc(C)c(S(=O)(=O)N2CCN3C(=O)c4c(ccnc4C)C3(C)C2)cc1C] | 2-{[4-(Ethyloxy)-2,5-dimethylphenyl]sulfonyl}-7,10b-dimethyl-1,3,4,10b-tetrahydropyrido[4',3':3,4]pyrrolo[1,2-a]pyrazin-6(2H)-one |
| 145 | 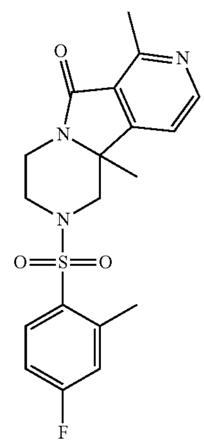 [SMILES: Cc1cc(F)ccc1S(=O)(=O)N1CCN2C(=O)c3c(ccnc3C)C2(C)C1] | 2-[(4-Fluoro-2-methylphenyl)sulfonyl]-7,10b-dimethyl-1,3,4,10b-tetrahydropyrido[4',3':3,4]pyrrolo[1,2-a]pyrazin-6(2H)-one |
| 146 | 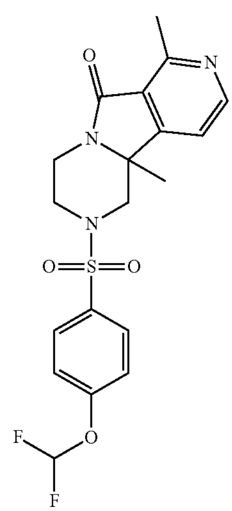 [SMILES: Cc1nccc2c1C(=O)N1CCN(S(=O)(=O)c3ccc(OC(F)F)cc3)CC21C] | 2-({4-[(Difluoromethyl)oxy]phenyl}sulfonyl)-7,10b-dimethyl-1,3,4,10b-tetrahydropyrido[4',3':3,4]pyrrolo[1,2-a]pyrazin-6(2H)-one |

TABLE 7-continued

| Compound No. | Structure | Name |
|---|---|---|
| 147 | 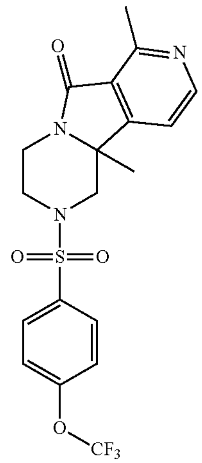 [SMILES: Cc1nccc2c1C(=O)N1CCN(S(=O)(=O)c3ccc(OC(F)(F)F)cc3)CC21C] | 7,10b-Dimethyl-2-({4-[(trifluoromethyl)oxy]phenyl}sulfonyl)-1,3,4,10b-tetrahydropyrido[4',3':3,4]pyrrolo[1,2-a]pyrazin-6(2H)-one |
| 148 | 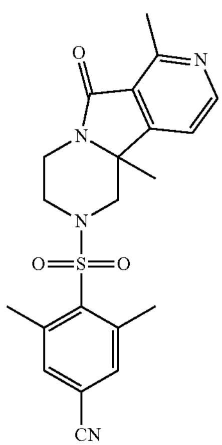 | 4-[(7,10b-Dimethyl-6-oxo-3,4,6,10b-tetrahydropyrido[4',3':3,4]pyrrolo[1,2-a]pyrazin-2(1H)-yl)sulfonyl]-3,5-dimethylbenzonitrile |
| 149 | 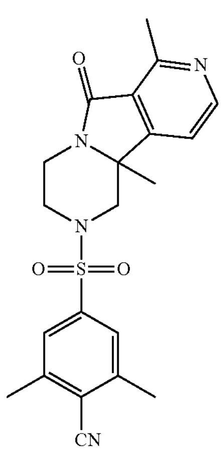 [SMILES: Cc1cc(S(=O)(=O)N2CCN3C(=O)c4c(ccnc4C)C3(C)C2)cc(C)c1C#N] | 4-[(7,10b-Dimethyl-6-oxo-3,4,6,10b-tetrahydropyrido[4',3':3,4]pyrrolo[1,2-a]pyrazin-2(1H)-yl)sulfonyl]-2,6-dimethylbenzonitrile |
| 150 | | 7,10b-Dimethyl-2-{[3-(trifluoromethyl)phenyl]sulfonyl}-1,3,4,10b-tetrahydropyrido[4',3':3,4]pyrrolo[1,2-a]pyrazin-6(2H)-one |
| 151 | | 7,10b-Dimethyl-2-({3-[(trifluoromethyl)oxy]phenyl}sulfonyl)-1,3,4,10b-tetrahydropyrido[4',3':3,4]pyrrolo[1,2-a]pyrazin-6(2H)-one |
| 152 | | 2-({3-[(Difluoromethyl)oxy]phenyl}sulfonyl)-7,10b-dimethyl-1,3,4,10b-tetrahydropyrido[4',3':3,4]pyrrolo[1,2-a]pyrazin-6(2H)-one |

TABLE 7-continued

| Compound No. | Structure | Name |
|---|---|---|
| 153 | 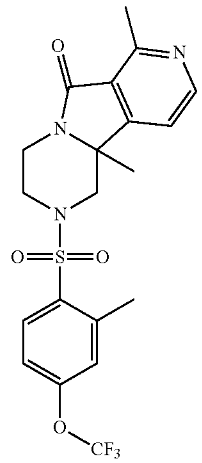 [SMILES: Cc1cc(OC(F)(F)F)ccc1S(=O)(=O)N1CCN2C(=O)c3c(ccnc3C)C2(C)C1] | 7,10b-Dimethyl-2-({2-methyl-4-[(trifluoromethyl)oxy]phenyl}sulfonyl)-1,3,4,10b-tetrahydropyrido[4',3':3,4]pyrrolo[1,2-a]pyrazin-6(2H)-one |
| 154 | 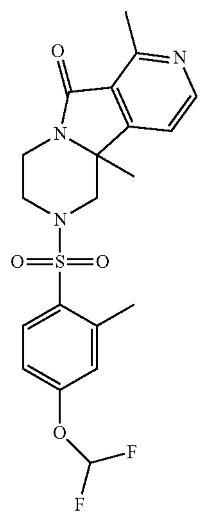 [SMILES: Cc1cc(OC(F)F)ccc1S(=O)(=O)N1CCN2C(=O)c3c(ccnc3C)C2(C)C1] | 2-({4-[(Difluoromethyl)oxy]-2-methylphenyl}sulfonyl)-7,10b-dimethyl-1,3,4,10b-tetrahydropyrido[4',3':3,4]pyrrolo[1,2-a]pyrazin-6(2H)-one |
| 155 | 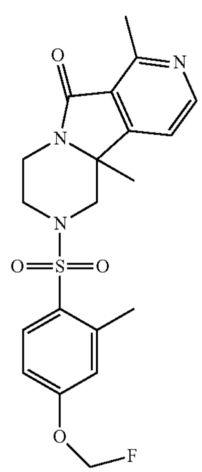 [SMILES: Cc1cc(OCF)ccc1S(=O)(=O)N1CCN2C(=O)c3c(ccnc3C)C2(C)C1] | 2-({4-[(Fluoromethyl)oxy]-2-methylphenyl}sulfonyl)-7,10b-dimethyl-1,3,4,10b-tetrahydropyrido[4',3':3,4]pyrrolo[1,2-a]pyrazin-6(2H)-one |
| 156 | | 2-({4-[(Fluoromethyl)oxy]phenyl}sulfonyl)-7,10b-dimethyl-1,3,4,10b-tetrahydropyrido[4',3':3,4]pyrrolo[1,2-a]pyrazin-6(2H)-one |
| 157 | | 2-({3-[(Fluoromethyl)oxy]phenyl}sulfonyl)-7,10b-dimethyl-1,3,4,10b-tetrahydropyrido[4',3':3,4]pyrrolo[1,2-a]pyrazin-6(2H)-one |

TABLE 8

| Compound No. | Structure | Name |
|---|---|---|
| 158 | 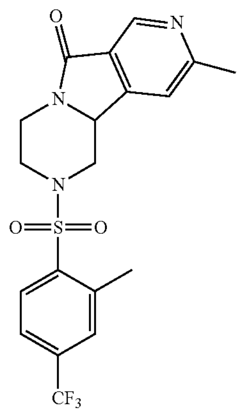 [SMILES: Cc1cc2c(cn1)C(=O)N1CCN(S(=O)(=O)c3ccc(C(F)(F)F)cc3C)CC21] | 9-Methyl-2-{[2-methyl-4-(trifluoromethyl)phenyl]sulfonyl}-1,3,4,10b-tetrahydropyrido[4',3':3,4]pyrrolo[1,2-a]pyrazin-6(2H)-one |
| 159 | 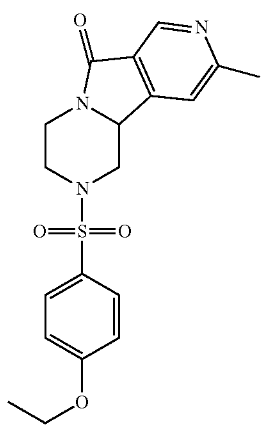 [SMILES: CCOc1ccc(S(=O)(=O)N2CCN3C(=O)c4cnc(C)cc4C3C2)cc1] | 2-{[4-(Ethyloxy)phenyl]sulfonyl}-9-methyl-1,3,4,10b-tetrahydropyrido[4',3':3,4]pyrrolo[1,2-a]pyrazin-6(2H)-one |
| 160 | 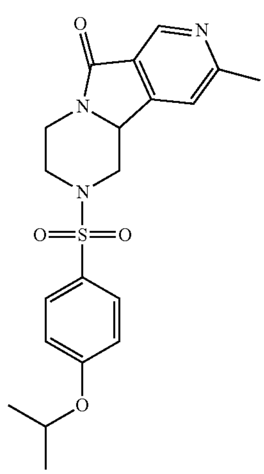 | 9-Methyl-2-({4-[(1-methylethyl)oxy]phenyl}sulfonyl)-1,3,4,10b-tetrahydropyrido[4',3':3,4]pyrrolo[1,2-a]pyrazin-6(2H)-one |

TABLE 8-continued

| Compound No. | Structure | Name |
| --- | --- | --- |
| 161 | 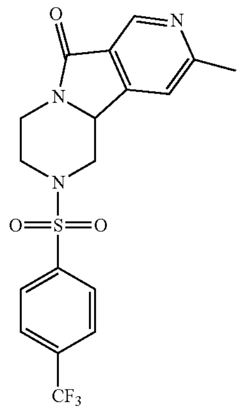 | 9-Methyl-2-{[4-(trifluoromethyl)phenyl]sulfonyl}-1,3,4,10b-tetrahydropyrido[4',3':3,4]pyrrolo[1,2-a]pyrazin-6(2H)-one |
| 162 | 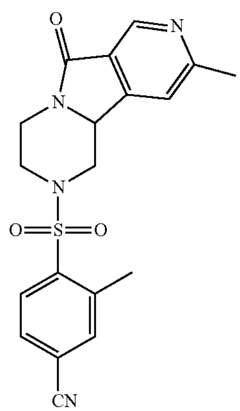 | 3-Methyl-4-[(9-methyl-6-oxo-3,4,6,10b-tetrahydropyrido[4',3':3,4]pyrrolo[1,2-a]pyrazin-2(1H)-yl)sulfonyl]benzonitrile |
| 163 | 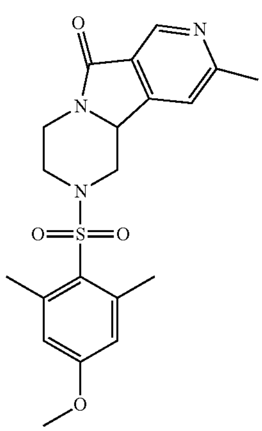 | 2-{[2,6-Dimethyl-4-(methyloxy)phenyl]sulfonyl}-9-methyl-1,3,4,10b-tetrahydropyrido[4',3':3,4]pyrrolo[1,2-a]pyrazin-6(2H)-one |

TABLE 8-continued

| Compound No. | Structure | Name |
|---|---|---|
| 164 | 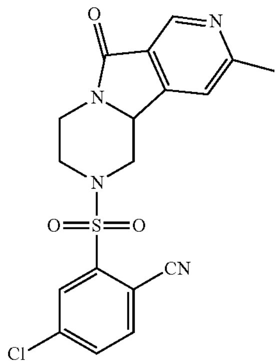 [SMILES: Cc1cc2c(cn1)C(=O)N1CCN(S(=O)(=O)c3cc(Cl)ccc3C#N)CC21] | 4-Chloro-2-[(9-methyl-6-oxo-3,4,6,10b-tetrahydropyrido[4',3':3,4]pyrrolo[1,2-a]pyrazin-2(1H)-yl)sulfonyl]benzonitrile |
| 165 | 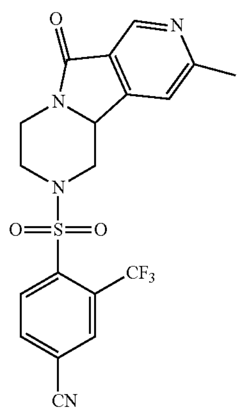 | 4-[(9-Methyl-6-oxo-3,4,6,10b-tetrahydropyrido[4',3':3,4]pyrrolo[1,2-a]pyrazin-2(1H)-yl)sulfonyl]-3-(trifluoromethyl)benzonitrile |
| 166 | 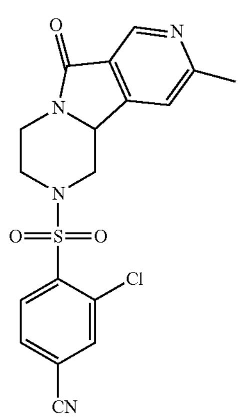 [SMILES: Cc1cc2c(cn1)C(=O)N1CCN(S(=O)(=O)c3ccc(C#N)cc3Cl)CC21] | 3-Chloro-4-[(9-methyl-6-oxo-3,4,6,10b-tetrahydropyrido[4',3':3,4]pyrrolo[1,2-a]pyrazin-2(1H)-yl)sulfonyl]benzonitrile |

TABLE 8-continued

| Compound No. | Structure | Name |
|---|---|---|
| 167 | 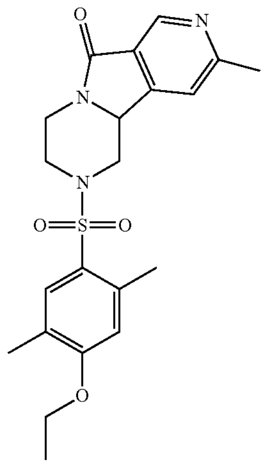 | 2-{[4-(Ethyloxy)-2,5-dimethylphenyl]sulfonyl}-9-methyl-1,3,4,10b-tetrahydropyrido[4',3':3,4]pyrrolo[1,2-a]pyrazin-6(2H)-one |
| 168 | 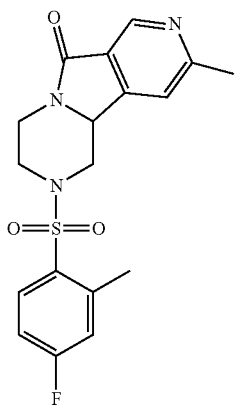 [SMILES: Cc1cc2c(cn1)C(=O)N1CCN(S(=O)(=O)c3ccc(F)cc3C)CC21] | 2-[(4-Fluoro-2-methylphenyl)sulfonyl]-9-methyl-1,3,4,10b-tetrahydropyrido[4',3':3,4]pyrrolo[1,2-a]pyrazin-6(2H)-one |
| 169 | 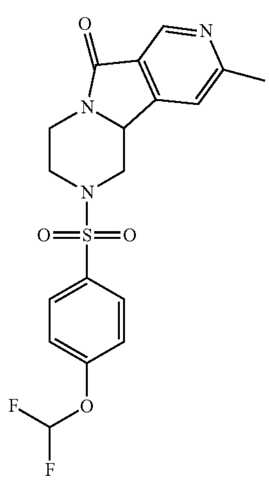 [SMILES: Cc1cc2c(cn1)C(=O)N1CCN(S(=O)(=O)c3ccc(OC(F)F)cc3)CC21] | 2-({4-[(Difluoromethyl)oxy]phenyl}sulfonyl)-9-methyl-1,3,4,10b-tetrahydropyrido[4',3':3,4]pyrrolo[1,2-a]pyrazin-6(2H)-one |

TABLE 8-continued

| Compound No. | Structure | Name |
|---|---|---|
| 170 | 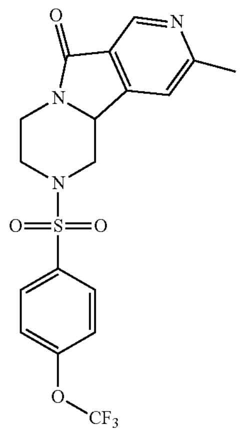 [SMILES: Cc1cc2c(cn1)C(=O)N1CCN(S(=O)(=O)c3ccc(OC(F)(F)F)cc3)CC21] | 9-Methyl-2-({4-[(trifluoromethyl)oxy]phenyl}sulfonyl)-1,3,4,10b-tetrahydropyrido[4',3':3,4]pyrrolo[1,2-a]pyrazin-6(2H)-one |
| 171 | 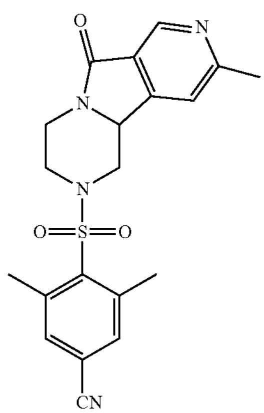 | 3,5-Dimethyl-4-[(9-methyl-6-oxo-3,4,6,10b-tetrahydropyrido[4',3':3,4]pyrrolo[1,2-a]pyrazin-2(1H)-yl)sulfonyl]benzonitrile |
| 172 | 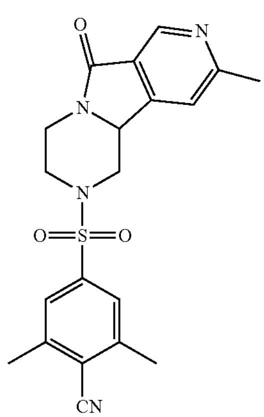 | 2,6-Dimethyl-4-[(9-methyl-6-oxo-3,4,6,10b-tetrahydropyrido[4',3':3,4]pyrrolo[1,2-a]pyrazin-2(1H)-yl)sulfonyl]benzonitrile |

TABLE 8-continued
| Compound No. | Structure | Name |
|---|---|---|
| 173 | 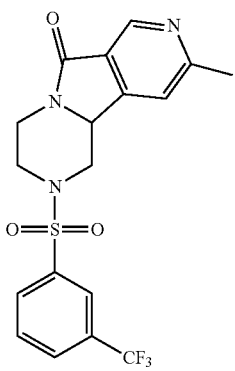 [SMILES: Cc1cc2c(cn1)C(=O)N1CCN(S(=O)(=O)c3cccc(C(F)(F)F)c3)CC21] | 9-Methyl-2-{[3-(trifluoromethyl)phenyl]sulfonyl}-1,3,4,10b-tetrahydropyrido[4',3':3,4]pyrrolo[1,2-a]pyrazin-6(2H)-one |
| 174 | 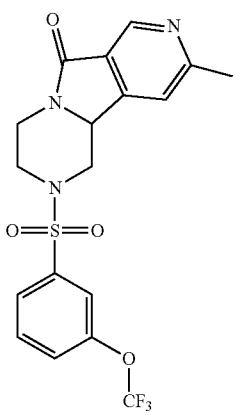 [SMILES: Cc1cc2c(cn1)C(=O)N1CCN(S(=O)(=O)c3cccc(OC(F)(F)F)c3)CC21] | 9-Methyl-2-({3-[(trifluoromethyl)oxy]phenyl}sulfonyl)-1,3,4,10b-tetrahydropyrido[4',3':3,4]pyrrolo[1,2-a]pyrazin-6(2H)-one |
| 175 | 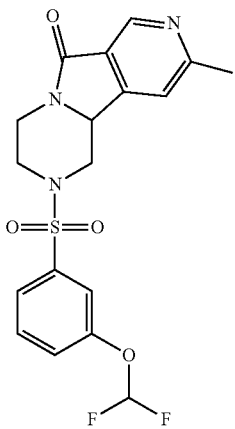 [SMILES: Cc1cc2c(cn1)C(=O)N1CCN(S(=O)(=O)c3cccc(OC(F)F)c3)CC21] | 2-({3-[(Difluoromethyl)oxy]phenyl}sulfonyl)-9-methyl-1,3,4,10b-tetrahydropyrido[4',3':3,4]pyrrolo[1,2-a]pyrazin-6(2H)-one |

TABLE 8-continued

| Compound No. | Structure | Name |
|---|---|---|
| 176 | 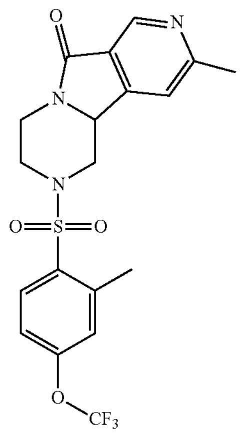 [SMILES: Cc1cc2c(cn1)C(=O)N1CCN(S(=O)(=O)c3ccc(OC(F)(F)F)cc3C)CC21] | 9-Methyl-2-({2-methyl-4-[(trifluoromethyl)oxy]phenyl}sulfonyl)-1,3,4,10b-tetrahydropyrido[4',3':3,4]pyrrolo[1,2-a]pyrazin-6(2H)-one |
| 177 | 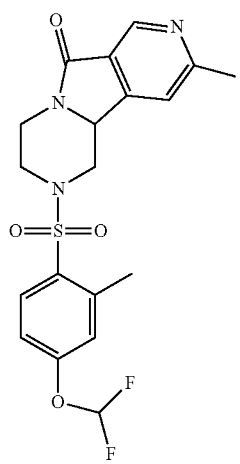 [SMILES: Cc1cc2c(cn1)C(=O)N1CCN(S(=O)(=O)c3ccc(OC(F)F)cc3C)CC21] | 2-({4-[(Difluoromethyl)oxy]-2-methylphenyl}sulfonyl)-9-methyl-1,3,4,10b-tetrahydropyrido[4',3':3,4]pyrrolo[1,2-a]pyrazin-6(2H)-one |
| 178 | 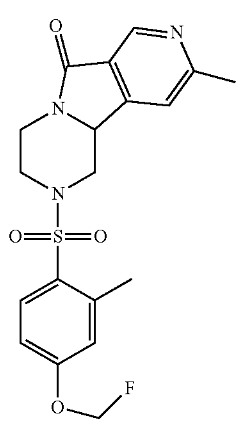 [SMILES: Cc1cc2c(cn1)C(=O)N1CCN(S(=O)(=O)c3ccc(OCF)cc3C)CC21] | 2-({4-[(Fluoromethyl)oxy]-2-methylphenyl}sulfonyl)-9-methyl-1,3,4,10b-tetrahydropyrido[4',3':3,4]pyrrolo[1,2-a]pyrazin-6(2H)-one |

TABLE 8-continued

| Compound No. | Structure | Name |
|---|---|---|
| 179 | 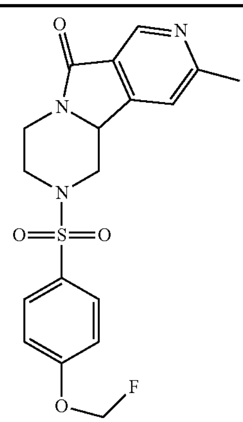 | 2-({4-[(Fluoromethyl)oxy]phenyl}sulfonyl)-9-methyl-1,3,4,10b-tetrahydropyrido[4',3':3,4]pyrrolo[1,2-a]pyrazin-6(2H)-one |
| 180 | 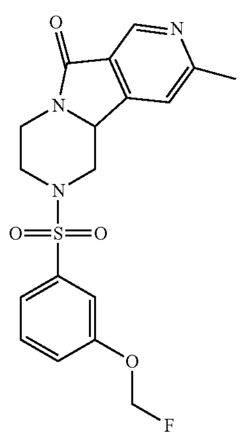 [SMILES: Cc1cc2c(cn1)C(=O)N1CCN(S(=O)(=O)c3cccc(OCF)c3)CC21] | 2-({3-[(Fluoromethyl)oxy]phenyl}sulfonyl)-9-methyl-1,3,4,10b-tetrahydropyrido[4',3':3,4]pyrrolo[1,2-a]pyrazin-6(2H)-one |

TABLE 9

| Compound No. | Structure | Name |
|---|---|---|
| 181 | 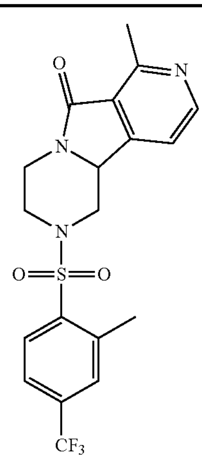 | 7-Methyl-2-{[2-methyl-4-(trifluoromethyl)phenyl]sulfonyl}-1,3,4,10b-tetrahydropyrido[4',3':3,4]pyrrolo[1,2-a]pyrazin-6(2H)-one |
| 182 | | 2-{[4-(Ethyloxy)phenyl]sulfonyl}-7-methyl-1,3,4,10b-tetrahydropyrido[4',3':3,4]pyrrolo[1,2-a]pyrazin-6(2H)-one |

TABLE 9-continued

| Compound No. | Structure | Name |
|---|---|---|
| 183 | 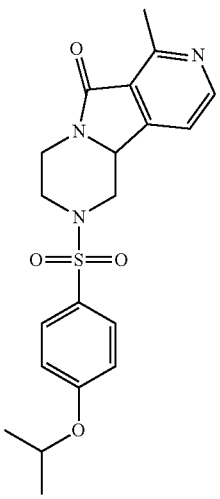 [SMILES: Cc1nccc2c1C(=O)N1CCN(S(=O)(=O)c3ccc(OC(C)C)cc3)CC21] | 7-Methyl-2-({4-[(1-methylethyl)oxy]phenyl}sulfonyl)-1,3,4,10b-tetrahydropyrido[4',3':3,4]pyrrolo[1,2-a]pyrazin-6(2H)-one |
| 184 | 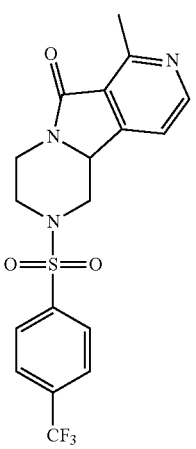 [SMILES: Cc1nccc2c1C(=O)N1CCN(S(=O)(=O)c3ccc(C(F)(F)F)cc3)CC21] | 7-Methyl-2-{[4-(trifluoromethyl)phenyl]sulfonyl}-1,3,4,10b-tetrahydropyrido[4',3':3,4]pyrrolo[1,2-a]pyrazin-6(2H)-one |
| 185 | 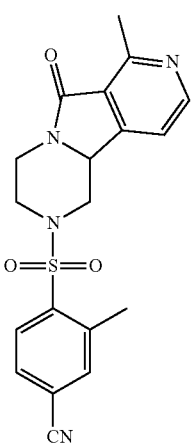 [SMILES: Cc1cc(C#N)ccc1S(=O)(=O)N1CCN2C(=O)c3c(ccnc3C)C2C1] | 3-Methyl-4-[(7-methyl-6-oxo-3,4,6,10b-tetrahydropyrido[4',3':3,4]pyrrolo[1,2-a]pyrazin-2(1H)-yl)sulfonyl]benzonitrile |
| 186 | 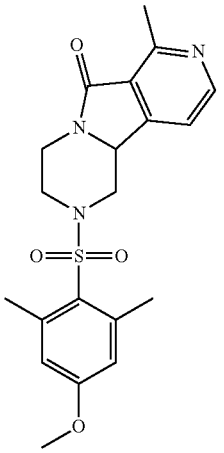 [SMILES: COc1cc(C)c(S(=O)(=O)N2CCN3C(=O)c4c(ccnc4C)C3C2)c(C)c1] | 2-{[2,6-Dimethyl-4-(methyloxy)phenyl]sulfonyl}-7-methyl-1,3,4,10b-tetrahydropyrido[4',3':3,4]pyrrolo[1,2-a]pyrazin-6(2H)-one |
| 187 | 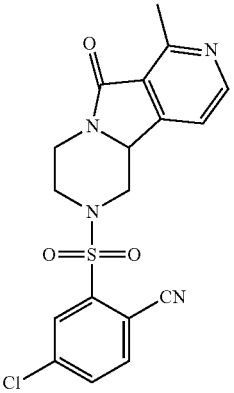 [SMILES: Cc1nccc2c1C(=O)N1CCN(S(=O)(=O)c3cc(Cl)ccc3C#N)CC21] | 4-Chloro-2-[(7-methyl-6-oxo-3,4,6,10b-tetrahydropyrido[4',3':3,4]pyrrolo[1,2-a]pyrazin-2(1H)-yl)sulfonyl]benzonitrile |
| 188 | 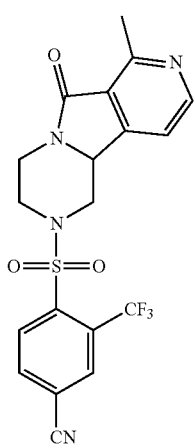 | 4-[(7-Methyl-6-oxo-3,4,6,10b-tetrahydropyrido[4',3':3,4]pyrrolo[1,2-a]pyrazin-2(1H)-yl)sulfonyl]-3-(trifluoromethyl)benzonitrile |

TABLE 9-continued

| Compound No. | Structure | Name |
|---|---|---|
| 189 | 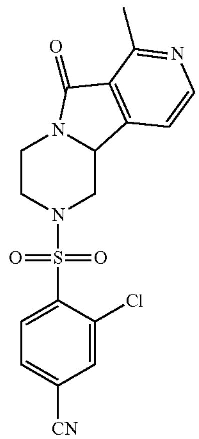 | 3-Chloro-4-[(7-methyl-6-oxo-3,4,6,10b-tetrahydropyrido[4',3':3,4]pyrrolo[1,2-a]pyrazin-2(1H)-yl)sulfonyl]benzonitrile |
| 190 | 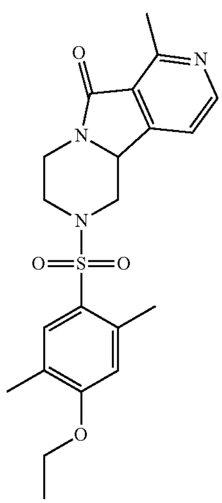 [SMILES: CCOc1cc(C)c(S(=O)(=O)N2CCN3C(=O)c4c(ccnc4C)C3C2)cc1C] | 2-{[4-(Ethyloxy)-2,5-dimethylphenyl]sulfonyl}-7-methyl-1,3,4,10b-tetrahydropyrido[4',3':3,4]pyrrolo[1,2-a]pyrazin-6(2H)-one |
| 191 | 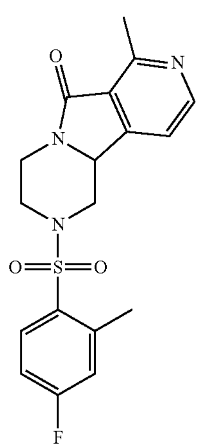 [SMILES: Cc1cc(F)ccc1S(=O)(=O)N1CCN2C(=O)c3c(ccnc3C)C2C1] | 2-[(4-Fluoro-2-methylphenyl)sulfonyl]-7-methyl-1,3,4,10b-tetrahydropyrido[4',3':3,4]pyrrolo[1,2-a]pyrazin-6(2H)-one |
| 192 | | 2-({4-[(Difluoromethyl)oxy]phenyl}sulfonyl)-7-methyl-1,3,4,10b-tetrahydropyrido[4',3':3,4]pyrrolo[1,2-a]pyrazin-6(2H)-one |
| 193 | | 7-Methyl-2-({4-[(trifluoromethyl)oxy]phenyl}sulfonyl)-1,3,4,10b-tetrahydropyrido[4',3':3,4]pyrrolo[1,2-a]pyrazin-6(2H)-one |
| 194 | | 3,5-Dimethyl-4-[(7-methyl-6-oxo-3,4,6,10b-tetrahydropyrido[4',3':3,4]pyrrolo[1,2-a]pyrazin-2(1H)-yl)sulfonyl]benzonitrile |

TABLE 9-continued

| Compound No. | Structure | Name |
|---|---|---|
| 195 | 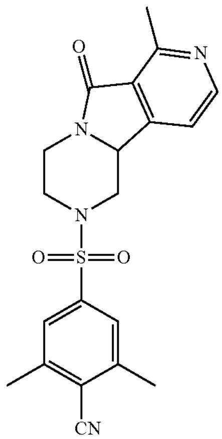 [SMILES: Cc1cc(S(=O)(=O)N2CCN3C(=O)c4c(ccnc4C)C3C2)cc(C)c1C#N] | 2,6-Dimethyl-4-[(7-methyl-6-oxo-3,4,6,10b-tetrahydropyrido[4',3':3,4]pyrrolo[1,2-a]pyrazin-2(1H)-yl)sulfonyl]benzonitrile |
| 196 | 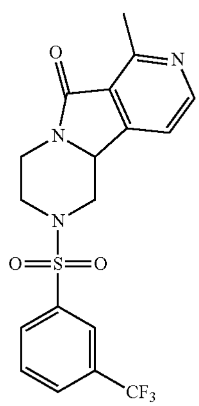 [SMILES: Cc1nccc2c1C(=O)N1CCN(S(=O)(=O)c3cccc(C(F)(F)F)c3)CC21] | 7-Methyl-2-{[3-(trifluoromethyl)phenyl]sulfonyl}-1,3,4,10b-tetrahydropyrido[4',3':3,4]pyrrolo[1,2-a]pyrazin-6(2H)-one |
| 197 | 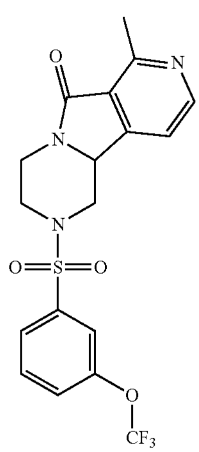 [SMILES: Cc1nccc2c1C(=O)N1CCN(S(=O)(=O)c3cccc(OC(F)(F)F)c3)CC21] | 7-Methyl-2-({3-[(trifluoromethyl)oxy]phenyl}sulfonyl)-1,3,4,10b-tetrahydropyrido[4',3':3,4]pyrrolo[1,2-a]pyrazin-6(2H)-one |
| 198 | 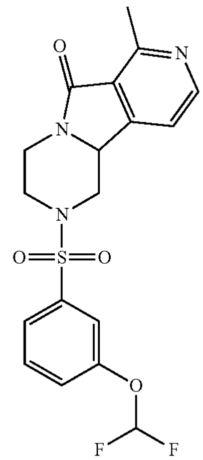 | 2-({3-[(Difluoromethyl)oxy]phenyl}sulfonyl)-7-methyl-1,3,4,10b-tetrahydropyrido[4',3':3,4]pyrrolo[1,2-a]pyrazin-6(2H)-one |
| 199 | 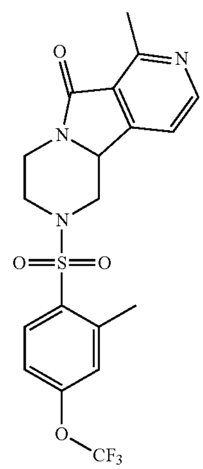 [SMILES: Cc1cc(OC(F)(F)F)ccc1S(=O)(=O)N1CCN2C(=O)c3c(ccnc3C)C2C1] | 7-Methyl-2-({2-methyl-4-[(trifluoromethyl)oxy]phenyl}sulfonyl)-1,3,4,10b-tetrahydropyrido[4',3':3,4]pyrrolo[1,2-a]pyrazin-6(2H)-one |
| 200 | 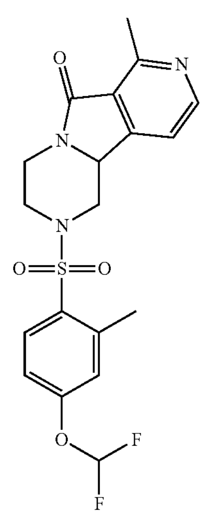 [SMILES: Cc1cc(OC(F)F)ccc1S(=O)(=O)N1CCN2C(=O)c3c(ccnc3C)C2C1] | 2-({4-[(Difluoromethyl)oxy]-2-methylphenyl}sulfonyl)-7-methyl-1,3,4,10b-tetrahydropyrido[4',3':3,4]pyrrolo[1,2-a]pyrazin-6(2H)-one |

TABLE 9-continued

| Compound No. | Structure | Name |
|---|---|---|
| 201 | 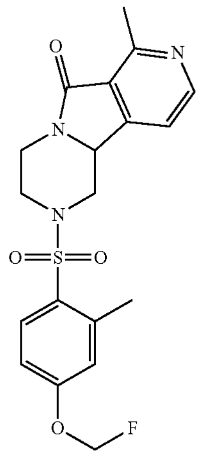 [SMILES: Cc1cc(OCF)ccc1S(=O)(=O)N1CCN2C(=O)c3c(ccnc3C)C2C1] | 2-({4-[(Fluoromethyl)oxy]-2-methylphenyl}sulfonyl)-7-methyl-1,3,4,10b-tetrahydropyrido[4',3':3,4]pyrrolo[1,2-a]pyrazin-6(2H)-one |
| 202 | 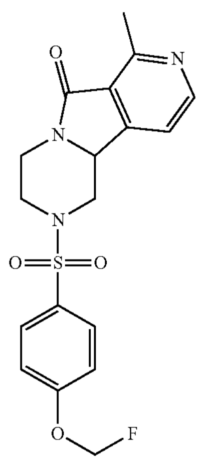 [SMILES: Cc1nccc2c1C(=O)N1CCN(S(=O)(=O)c3ccc(OCF)cc3)CC21] | 2-({4-[(Fluoromethyl)oxy]phenyl}sulfonyl)-7-methyl-1,3,4,10b-tetrahydropyrido[4',3':3,4]pyrrolo[1,2-a]pyrazin-6(2H)-one |
| 203 | 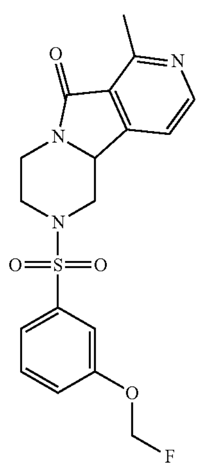 [SMILES: Cc1nccc2c1C(=O)N1CCN(S(=O)(=O)c3cccc(OCF)c3)CC21] | 2-({3-[(Fluoromethyl)oxy]phenyl}sulfonyl)-7-methyl-1,3,4,10b-tetrahydropyrido[4',3':3,4]pyrrolo[1,2-a]pyrazin-6(2H)-one |

Equipment:

$^1$H NMR Spectra

Chemical shifts are expressed in parts per million (ppm, units). Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Mass-Directed Automated HPLC/Mass-Directed Automated Preparation (MDAP)

Where indicated in the above compounds, purification by mass-directed automated HPLC was carried out using the following apparatus and conditions:

Hardware
  Waters 2525 Binary Gradient Module
  Waters 515 Makeup Pump
  Waters Pump Control Module
  Waters 2767 Inject Collect
  Waters Column Fluidics Manager
  Waters 2996 Photodiode Array Detector
  Waters ZQ Mass Spectrometer
  Gilson 202 fraction collector
  Gilson Aspec waste collector Software
  Waters MassLynx version 4 SP2

Column
  The columns used are Waters Atlantis, the dimensions of which are 19 mm×100 mm (small scale) and 30 mm×100 mm (large scale). The stationary phase particle size is 5 μm.

Solvents
  A: Aqueous solvent=Water+0.1% Formic Acid
  B: Organic solvent=Acetonitrile+0.1% Formic Acid
  Make up solvent=Methanol:Water 80:20
  Needle rinse solvent=Methanol Methods
  There are five methods used depending on the analytical retention time of the compound of interest. They have a 13.5-minute runtime, which comprises of a 10-minute gradient followed by a 3.5 minute column flush and re-equilibration step.
  Large/Small Scale 1.0-1.5=5-30% B
  Large/Small Scale 1.5-2.2=15-55% B
  Large/Small Scale 2.2-2.9=30-85% B
  Large/Small Scale 2.9-3.6=50-99% B
  Large/Small Scale 3.6-5.0=80-99% B (in 6 minutes followed by 7.5 minutes flush and re-equilibration)

Flow Rate
  All of the above methods have a flow rate of either 20 mls/min (Small Scale) or 40 mls/min (Large Scale).

High pH Focused Preparative Open Access LC/MS (High pH MDAP)

Column
  The columns used are Xbridge C18 column, the dimensions of which are 19 mm×100 mm (small scale) and 30 mm×150 mm (large scale). The stationary phase particle size is 5 μm.

Solvents
  A: Aqueous solvent=10 mM ammonium bicarbonate in water adjusted to pH10 with ammonia solution
  B: Organic solvent=Acetonitrile Methods
  There are five methods used depending on the analytical retention time of the compound of interest. The user can select a 15 minute or 25 minute runtime.
  Large/Small Scale Method A: 99% A to 1% A in B
  Large/Small Scale Method B=85% A to 1% A in B
  Large/Small Scale Method C=70% A to 1% A in B
  Large/Small Scale Method D=50% A to 1% A in B
  Large/Small Scale Method E=20% A to 1% A in B Flow Rate
  All of the above methods have a flow rate of either 20 mls/min (Small Scale) or 40 mls/min (Large Scale).

UV Detection

The UV detection was an averaged signal from wavelength of 210 nm to 350 nm and mass spectra were recorded on a mass spectrometer using alternate-scan positive and negative mode electrospray ionization.

Liquid Chromatography/Mass Spectrometry

Analysis of the above compounds by Liquid Chromatography/Mass Spectrometry (LC/MS) was carried out using the following apparatus and conditions:

Hardware
  Waters Acquity Binary Solvent Manager
  Waters Acquity Sample Manager
  Waters Acquity PDA
  Waters ZQ Mass Spectrometer
  Sedere Sedex 75
Software
  Waters MassLynx version 4.1
Column The column used is a Waters Acquity BEH UPLC C18, the dimensions of which are 2.1 mm×50 mm. The stationary phase particle size is 1.7 μm.

Solvents
  A: Aqueous solvent=Water+0.05% Formic Acid
  B: Organic solvent=Acetonitrile+0.05% Formic Acid
  Weak Wash=1:1 Methanol:Water
  Strong Wash=Water
Method The generic method used has a 2 minute runtime.

| Time/min | % B |
|---|---|
| 0 | 3 |
| 0.1 | 3 |
| 1.5 | 97 |
| 1.9 | 97 |
| 2.0 | 3 |

The above method has a flow rate of 1 ml/min.
The injection volume for the generic method is 0.5 μl
The column temperature is 40° C.
The UV detection range is from 220 to 330 nm High pH Liquid Chromatography/Mass Spectroscopy The analysis was conducted on an Acquity UPLC BEH C18 column (2.1 mm×50 mm i.d. 1.7 um packing diameter) at 40 degrees centigrade.

The solvents employed were:
A=10 mM Ammonium Bicarbonate in water adjusted to pH 10 with ammonia solution
B=Acetonitrile The gradient employed was from 1-100% B in A over a period of 2 minutes The UV detection was an averaged signal from wavelength of 220 nm to 350 nm and mass spectra were recorded on a mass spectrometer using alternate-scan positive and negative mode electrospray ionization Alternatively, the analysis was conducted on an XBridge C18 column (4.6 mm×50 mm i.d. 3.5 um packing diameter) at 30 degrees centigrade.

The solvents employed were:
A=10 mM Ammonium Bicarbonate in water adjusted to pH 10 with ammonia solution
B=Acetonitrile The gradient employed was from 1-97% B in A over a period of 5 minutes The UV detection was an averaged signal from wavelength of 220 nm to 350 nm and mass spectra were recorded on a mass spectrometer using alternate-scan positive and negative mode electrospray ionization Biotage SP4®

Biotage-SP4® is an automated purification system. It uses preloaded silica gel columns. The user applies their material to the top of the column and chooses solvents, gradients, flow rates, column size, collection method and eluting volumes.

The Biotage SP4® may also be used in reverse phase mode using a C18 column. The user applies their material to the top of the column and runs a standard gradient from 0-100% (0.1% formic acid in acetonitrile) in (0.1% formic acid in water). The user chooses the flow rate, column size, collection method and eluting volumes.

Phase Separators (Hydrophobic Frit)

Phase separators are a range of ISOLUTE® columns fitted with an optimized frit material that easily separates aqueous phase from chlorinated solvents under gravity.

SCX—Strong Cation Exchange Cartridge

Where indicated in the compounds, an SCX cartridge was used as part of the compound purification process. Typically an ISOLUTE SCX-2 cartridge was used. ISOLUTE SCX-2 is a silica-based sorbent with a chemically bonded propylsulfonic acid functional group.

ISOLUTE SCX-2 Chemical Data
Base Material: Silica, 50 μm
Functional Group: Propylsulfonic acid
Capacity: 0.6 meq/g
Counter Ion: Proton SAX—Strong Anion Exchange Cartridge Where indicated in the compounds, an SAX cartridge was used as part of the compound purification process. Typically an ISOLUTE SAX cartridge was used. ISOLUTE SAX is a silica-based sorbent with a chemically bonded quaternary trimethylaminopropyl chloride functional group.

$NH_2$—Aminopropyl Ion Exchange Cartridge

Where indicated in the compounds, an $NH_2$ cartridge was used as part of the compound purification process. Typically an ISOLUTE $NH_2$ cartridge was used. ISOLUTE $NH_2$ is a silica-based sorbent with a chemically bonded aminopropyl functional group.

Description: Aminopropyl functionalized silica. Manufactured using trifunctional silane. pK 9.8. Non end-capped.
Average Particle Size: 50 μm
Nominal Porosity: 60 Å
Exchange Capacity: 0.6 meq/g
Comments: Weak anion exchange sorbent for extraction of strongly ionized acidic drugs, particularly for ease of elution.

Pharmacological Data

Compounds as defined in the first to third aspects may be tested for in vitro biological activity in the $hCa_v2.2$ assay in accordance with the following studies:

Methods
Cell Biology

Stable cell lines expressing the human $Ca_v2.2$ α ($α1_B$) subunit, along with the human β3 and α2δ1 auxiliary subunits were created following sequential transfection and selection of human embryonic kidney (HEK293) cells. HEK293 cells were cultured in Dulbecco's modified Eagles media/F12 media (Invitrogen, Cat #041-95750V) containing 10% fetal bovine serum, with added L-glutamine (2 mM; Invitrogen, Cat #25030-024) and non-essential amino acids (5%; Invitrogen, Cat #11140-035). Initially HEK293 cells were transfected with two plasmid vectors for expression of the $hCa_v2.2$ α subunit (pCIN5-$hCa_v2.2$ which carries a neomycin resistance marker) and the $hCa_v$ β3 subunit (pCIH-$hCa_v$ β3 which carries a hygromycin resistance marker). Clonal cell lines were isolated following selection in media supplemented with 0.4 mg ml$^{-1}$ Geneticin G418 (Invitrogen, Cat #10131-027) and 0.1 mg ml$^{-1}$ hygromycin (Invitrogen, Cat #10687-

010). These clonal cell lines were assessed for $Ca_v2.2$ α/β3-mediated current expression using the IonWorks planar array electrophysiology technology (described below). A clonal line was identified that gave a reasonable level of functional $Ca_v2.2$ α/β3 current expression. This cell line was transfected with a plasmid vector for expression of the human α2δ1 subunit (pCIP-α2δ1 which carries a puromycin resistance marker) and clonal cell lines isolated following selection in media containing 0.62 μg ml$^{-1}$ puromycin (Sigma, Cat # P-7255), in addition to 0.4 mg ml$^{-1}$ Geneticin G418 and 0.1 mg ml$^{-1}$ hygromycin. Several cell lines were identified that gave robust levels of $Ca_v2.2$ at β3/α2δ1-mediated current expression and one of these was selected for compound profiling. Expression of all three subunits within this cell line was continuously maintained by the inclusion of G418 (0.4 mg ml$^{-1}$), hygromycin (0.1 mg ml$^{-1}$) and puromycin (0.62 μg ml$^{-1}$). Cells were maintained at 37° C. in a humidified environment containing 5% $CO_2$ in air. Cells were liberated from the T175 culture flasks for passage and harvesting using TrpLE (Invitrogen, Cat #12604-013).

Cell Preparation

Cells were grown to 30-60% confluence in T175 flasks and maintained at 30° C. for 24 hrs prior to recording. Cells were lifted by removing the growth media, washing with $Ca^{2+}$ free PBS (Invitrogen, Cat #14190-094) and incubating with 3 ml of warmed (37° C.) TrpLE (Invitrogen, Cat #12604-013) for 6 minutes. Lifted cells were suspended in 10 ml of extracellular buffer. Cell suspension was then placed into a 15 ml tube and centrifuged for 2 minutes at 700 rpm. After centrifugation, the supernatant was removed and the cell pellet was resuspended in 4.5 ml of extracellular solution.

Electrophysiology

Currents were recorded at room temperature (21-23° C.) using the IonWorks planar array electrophysiology technology (Molecular Devices Corp.). Stimulation protocols and data acquisition were carried out using a microcomputer (Dell Pentium 4). In order to determine planar electrode hole resistances (Rp), a 10 mV, 160 ms potential difference was applied across each hole. These measurements were performed before cell addition. After cell addition a seal test was performed prior to antibiotic (amphotericin) circulation to achieve intracellular access. Leak subtraction was conducted in all experiments by applying a 160 ms hyperpolarizing (10 mV) prepulse 200 ms before the test pulses to measure leak conductance. Test pulses stepping from the holding potential ($V_H$) of −90 mV to +10 mV were applied for 20 ms and repeated 10 times at a frequency of 10 Hz. In all experiments, the test pulse protocol was performed in the absence (pre-read) and presence (post-read) of a compound. Pre- and post-reads were separated by a compound addition followed by a 3-3.5 min incubation.

Solutions and Drugs

The intracellular solution contained the following (in mM): K-gluconate 120, KCl 20 mM, $MgCl_2$ 5, EGTA 5, HEPES 10, adjusted to pH 7.3. Amphotericin was prepared as 30 mg/ml stock solution and diluted to a final working concentration of 0.2 mg ml$^{-1}$ in intracellular buffer solution. The extracellular solution contained the following (in mM): Na-gluconate 120, NaCl 20, $MgCl_2$ 1, HEPES 10, $BaCl_2$ 5, adjusted to pH 7.4.

Compounds were prepared in DMSO as 10 mM stock solutions and subsequent 1:3 serial dilutions performed. Finally the compounds were diluted 1:100 in external solution resulting in a final DMSO concentration of 1%.

Data Analysis

The recordings were analysed and filtered using seal resistance (>40 MΩ), resistance reduction (>35%) and peak current amplitude (>200 pA) in the absence of compound to eliminate unsuitable cells from further analysis. Paired comparisons between pre-compound and post-compound additions were used to determine the inhibitory effect of each compound. The concentrations of compounds required to inhibit current elicited by the 1$^{st}$ depolarising pulse by 50% (tonic pIC50) were determined by fitting of the Hill equation to the concentration response data. In addition the use-dependent inhibitory properties of the compounds were determined by assessing the effect of compounds on the 10$^{th}$ versus 1$^{st}$ depolarising pulse. The ratio of the 10$^{th}$ over 1$^{st}$ pulse was determined in the absence and presence of drug and the % use-dependent inhibition calculated. The data was fitted using the same equation as for the tonic $pIC_{50}$ and the concentration producing 30% inhibition (use-dependent $pUD_{30}$) determined.

Compounds 1 to 7, 12 to 15, 18, 20, 21, 23, 24, 25 26 and 27 were tested in the $hCa_v2.2$ assay. Compounds were tested in the form as described herein. All compounds tested have been tested one or more times (up to 8 times). Variations in $pUD_{30}$ and $pIC_{50}$ values may arise between tests.

Compounds 1 to 7, 13 to 15, 18, 20, 21, 23, 24, 25, 26 and 27 exhibited a $pUD_{30}$ value of 4.5 or more than 4.5. Compounds 1, 2, 4, 6, 7, 14, 18, 20/21 (slower running enantiomer), 23, 24, 25, 26 and 27 exhibited a $pUD_{30}$ value of 5.0 or more than 5.0.

The compounds 2, 4, 18, 23, 24, 25 and 27 exhibited a $pUD_{30}$ value of 5.5 or more than 5.5. Compound 2 exhibited a $pUD_{30}$ of 5.7.

The compounds 18 and 24/25 (slower running enantiomer) exhibited a $pIC_{50}$ value of 4.5 or more than 4.5. No compound exhibited a $pIC_{50}$ value of 5.0 or more than 5.0. Compound 2 exhibited a $pIC_{50}$ of 4.0.

The invention claimed is:

1. A compound of formula (I):

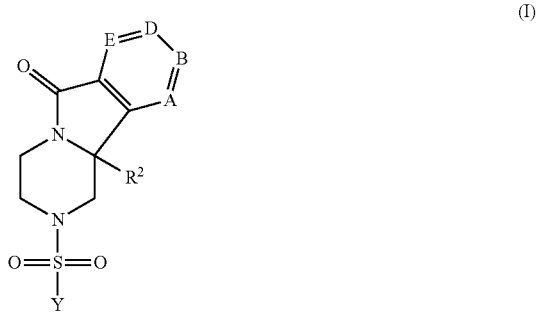

wherein (a) A is N, B is $CR^{1b}$, D is $CR^{1d}$ and E is $CR^{1e}$; or (b) B is N, A is $CR^{1a}$, D is $CR^{1d}$ and E is $CR^{1e}$; or (c) D is N, A is $CR^{1a}$, B is $CR^{1b}$ and E is $CR^{1e}$; or (d) E is N, A is $CR^{1a}$, B is $CR^{1b}$ and D is $CR^{1d}$;

$R^{1a}$, $R^{1b}$, $R^{1d}$ and $R^{1e}$ are independently selected from H and $C_{1-4}$ alkyl;

$R^2$ is H or methyl;

Y is

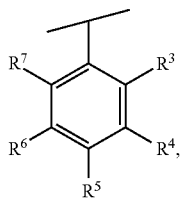

(i)

R³, R⁴, R⁵, R⁶ and R⁷ are independently selected from H, halogen, $C_{1-4}$ alkyl, $C_{1-4}$ alkoxy, cyano, $C_{1-4}$ haloalkyl or $C_{1-4}$ haloalkoxy, such that at least 1 of R³, R⁴, R⁵, R⁶ and R⁷ is a group other than H;

or a pharmaceutically acceptable salt thereof.

2. The compound as defined in claim 1, wherein R³ and R⁷ are selected from H or methyl; R⁴ and R⁶ are H; and R⁵ is selected from methoxy, isopropyloxy, trifluoromethyl, cyano and difluoromethoxy.

3. The compound as defined in claim 2, wherein R³ is methyl, R⁴ is H, R⁵ is trifluoromethyl or cyano, R⁶ is H and R⁷ is H.

4. The compound as defined in claim 2, wherein R³ is methyl, R⁴ is H, R⁵ is cyano or methoxy, R⁶ is H and R⁷ is methyl.

5. The compound as defined in claim 2, wherein R³ is H, R⁴ is H, R⁵ is isopropyloxy or difluoromethoxy, R⁶ is H and R⁷ is H.

6. The compound as defined in claim 1, which is a compound of formula (Ia):

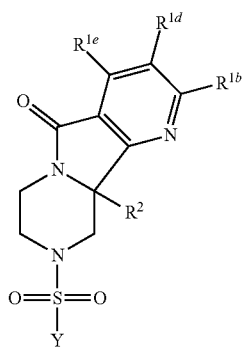

(Ia)

wherein $R^{1b}$, $R^{1d}$ and $R^{1e}$ are independently selected from H and $C_{1-4}$ alkyl.

7. The compound as defined in claim 1, which is a compound of formula (Ib):

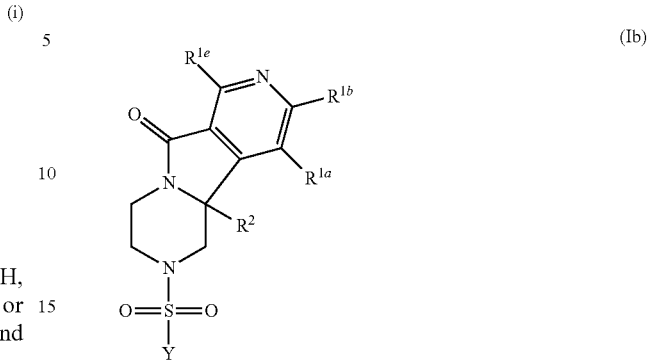

(Ib)

wherein $R^{1a}$, $R^{1b}$ and $R^{1e}$ are independently selected from H and $C_{1-4}$ alkyl.

8. The compound as defined in claim 1, wherein $R^{1b}$, $R^{1a}$, $R^{1e}$ and $R^2$ are H.

9. The compound as defined in claim 1, wherein $R^{1b}$, $R^{1d}$, $R^{1e}$ are H and $R^2$ is methyl.

10. The compound as defined in claim 1, wherein $R^{1d}$ and $R^{1e}$ are H, $R^{1b}$ is methyl, and $R^2$ is methyl.

11. The compound as defined in claim 1, which is selected from:
- 9-{[4-(Ethyloxy)phenyl]sulfonyl}-2-methyl-8,9,10,10a-tetrahydropyrido[2',3':3,4]pyrrolo[1,2-a]pyrazin-5(7H)-one;
- 2-Methyl-9-({4-[(1-methylethyl)oxy]phenyl}sulfonyl)-8,9,10,10a-tetrahydropyrido[2',':3,4]pyrrolo[1,2-a]pyrazin-5(7H)-one;
- 3-[(2-Methyl-5-oxo-7,8,10,10a-tetrahydropyrido[2',3':3,4]pyrrolo[1,2-a]pyrazin-9(5H)-yl)sulfonyl]benzonitrile;
- 2-Methyl-9-{[4-(trifluoromethyl)phenyl]sulfonyl}-8,9,10,10a-tetrahydropyrido[2',':3,4]pyrrolo[1,2-a]pyrazin-5(7H)-one;
- 3-Methyl-4-[(2-methyl-5-oxo-7,8,10,10a-tetrahydropyrido[2',3':3,4]pyrrolo[1,2-a]pyrazin-9(5H)-yl)sulfonyl]benzonitrile;
- 9-{[2,6-Dimethyl-4-(methyloxy)phenyl]sulfonyl}-2-methyl-8,9,10,10a-tetrahydropyrido[2',3':3,4]pyrrolo[1,2-a]pyrazin-5(7H)-one;
- 4-Chloro-2-[(2-methyl-5-oxo-7,8,10,10a-tetrahydropyrido[2',3':3,4]pyrrolo[1,2-a]pyrazin-9(5H)-yl)sulfonyl]benzonitrile;
- 4-[(2-Methyl-5-oxo-7,8,10,10a-tetrahydropyrido[2',3':3,4]pyrrolo[1,2-a]pyrazin-9(5H)-yl)sulfonyl]-3-(trifluoromethyl)benzonitrile;
- 3-Chloro-4-[(2-methyl-5-oxo-7,8,10,10a-tetrahydropyrido[2',3':3,4]pyrrolo[1,2-a]pyrazin-9(5H)-yl)sulfonyl]benzonitrile;
- 9-{[4-(Ethyloxy)-2,5-dimethylphenyl]sulfonyl}-2-methyl-8,9,10,10a-tetrahydropyrido[2',3':3,4]pyrrolo[1,2-a]pyrazin-5(7H)-one;
- 9-[(4-Fluoro-2-methylphenyl)sulfonyl]-2-methyl-8,9,10,10a-tetrahydropyrido[2',3':3,4]pyrrolo[1,2-a]pyrazin-5(7H)-one;
- 9-({4-[(Difluoromethyl)oxy]phenyl}sulfonyl)-2-methyl-8,9,10,10a-tetrahydropyrido[2',3':3,4]pyrrolo[1,2-a]pyrazin-5(7H)-one;
- 2-Methyl-9-{[5-methyl-2-(methyloxy)phenyl]sulfonyl}-8,9,10,10a-tetrahydropyrido[2',3':3,4]pyrrolo[1,2-a]pyrazin-5(7H)-one;

2-Methyl-9-({[4-(trifluoromethyl)phenyl]methyl}sulfonyl)-8,9,10,10a-tetrahydropyrido[2',3':3,4]pyrrolo[1,2-a]pyrazin-5(7H)-one;

2-Methyl-9-{[2-methyl-4-(trifluoromethyl)phenyl]sulfonyl}-8,9,10,10a-tetrahydropyrido[2',3':3,4]pyrrolo[1,2-a]pyrazin-5(7H)-one;

4-Methyl-2-[(2-methyl-5-oxo-7,8,10,10a-tetrahydropyrido[2',3':3,4]pyrrolo[1,2-a]pyrazin-9(5H)-yl)sulfonyl]benzonitrile;

(10aS)-9-{[4-(Ethyloxy)phenyl]sulfonyl}-2-methyl-8,9,10,10a-tetrahydropyrido[2',3':3,4]pyrrolo[1,2-a]pyrazin-5(7H)-one;

(10aR)-9-{[4-(Ethyloxy)phenyl]sulfonyl}-2-methyl-8,9,10,10a-tetrahydropyrido[2',3':3,4]pyrrolo[1,2-a]pyrazin-5(7H)-one;

9-{[4-(Ethyloxy)phenyl]sulfonyl}-2,10a-dimethyl-8,9,10,10a-tetrahydropyrido[2',3':3,4]pyrrolo[1,2-a]pyrazin-5(7H)-one;

9-{[2-Methyl-4-(trifluoromethyl)phenyl]sulfonyl}-8,9,10,10a-tetrahydropyrido[2',3':3,4]pyrrolo[1,2-a]pyrazin-5(7H)-one;

(10aS)-9-{[2-Methyl-4-(trifluoromethyl)phenyl]sulfonyl}-8,9,10,10a-tetrahydropyrido[2',3':3,4]pyrrolo[1,2-a]pyrazin-5(7H)-one;

(10aR)-9-{[2-Methyl-4-(trifluoromethyl)phenyl]sulfonyl}-8,9,10,10a-tetrahydropyrido[2',3':3,4]pyrrolo[1,2-a]pyrazin-5(7H)-one;

2-{[4-(Trifluoromethyl)phenyl]sulfonyl}-1,3,4,10b-tetrahydropyrido[4',3':3,4]pyrrolo[1,2-a]pyrazin-6(2H)-one;

2-{[2-Methyl-4-(trifluoromethyl)phenyl]sulfonyl}-1,3,4,10b-tetrahydropyrido[4',3':3,4]pyrrolo[1,2-a]pyrazin-6(2H)-one;

2-Methyl-9-({4-[(trifluoromethyl)oxy]phenyl}sulfonyl)-8,9,10,10a-tetrahydropyrido[2',3':3,4]pyrrolo[1,2-a]pyrazin-5(7H)-one;

3,5-Dimethyl-4-[(2-methyl-5-oxo-7,8,10,10a-tetrahydropyrido[2',3':3,4]pyrrolo[1,2-a]pyrazin-9(5H)-yl)sulfonyl]benzonitrile;

2,6-Dimethyl-4-[(2-methyl-5-oxo-7,8,10,10a-tetrahydropyrido[2',3':3,4]pyrrolo[1,2-a]pyrazin-9(5H)-yl)sulfonyl]benzonitrile;

2-Methyl-9-{[3-(trifluoromethyl)phenyl]sulfonyl}-8,9,10,10a-tetrahydropyrido[2',3':3,4]pyrrolo[1,2-a]pyrazin-5(7H)-one;

2-Methyl-9-({3-[(trifluoromethyl)oxy]phenyl}sulfonyl)-8,9,10,10a-tetrahydropyrido[2',3':3,4]pyrrolo[1,2-a]pyrazin-5(7H)-one;

9-({3-[(Difluoromethyl)oxy]phenyl}sulfonyl)-2-methyl-8,9,10,10a-tetrahydropyrido[2',3':3,4]pyrrolo[1,2-a]pyrazin-5(7H)-one;

2-Methyl-9-({2-methyl-4-[(trifluoromethyl)oxy]phenyl}sulfonyl)-8,9,10,10a-tetrahydropyrido[2',3':3,4]pyrrolo[1,2-a]pyrazin-5(7H)-one;

9-({4-[(Difluoromethyl)oxy]-2-methylphenyl}sulfonyl)-2-methyl-8,9,10,10a-tetrahydropyrido[2',3':3,4]pyrrolo[1,2-a]pyrazin-5(7H)-one;

9-({4-[(Fluoromethyl)oxy]-2-methylphenyl}sulfonyl)-2-methyl-8,9,10,10a-tetrahydropyrido[2',3':3,4]pyrrolo[1,2-a]pyrazin-5(7H)-one;

9-({4-[(Fluoromethyl)oxy]phenyl}sulfonyl)-2-methyl-8,9,10,10a-tetrahydropyrido[2',3':3,4]pyrrolo[1,2-a]pyrazin-5(7H)-one;

9-({3-[(Fluoromethyl)oxy]phenyl}sulfonyl)-2-methyl-8,9,10,10a-tetrahydropyrido[2',3':3,4]pyrrolo[1,2-a]pyrazin-5(7H)-one;

9-({4-[(1-Methylethyl)oxy]phenyl}sulfonyl)-8,9,10,10a-tetrahydropyrido[2',3':3,4]pyrrolo[1,2-a]pyrazin-5(7H)-one;

3-[(5-Oxo-7,8,10,10a-tetrahydropyrido[2',3':3,4]pyrrolo[1,2-a]pyrazin-9(5H)-yl)sulfonyl]benzonitrile;

9-{[4-(Trifluoromethyl)phenyl]sulfonyl}-8,9,10,10a-tetrahydropyrido[2',3':3,4]pyrrolo[1,2-a]pyrazin-5(7H)-one;

3-Methyl-4-[(5-oxo-7,8,10,10a-tetrahydropyrido[2',3':3,4]pyrrolo[1,2-a]pyrazin-9(5H)-yl)sulfonyl]benzonitrile;

9-{[2,6-Dimethyl-4-(methyloxy)phenyl]sulfonyl}-8,9,10,10a-tetrahydropyrido[2',3':3,4]pyrrolo[1,2-a]pyrazin-5(7H)-one;

4-Chloro-2-[(5-oxo-7,8,10,10a-tetrahydropyrido[2',3':3,4]pyrrolo[1,2-a]pyrazin-9(5H)-yl)sulfonyl]benzonitrile;

4-[(5-Oxo-7,8,10,10a-tetrahydropyrido[2',3':3,4]pyrrolo[1,2-a]pyrazin-9(5H)-yl)sulfonyl]-3-(trifluoromethyl)benzonitrile;

3-Chloro-4-[(5-oxo-7,8,10,10a-tetrahydropyrido[2',3':3,4]pyrrolo[1,2-a]pyrazin-9(5H)-yl)sulfonyl]benzonitrile;

9-{[4-(Ethyloxy)-2,5-dimethylphenyl]sulfonyl}-8,9,10,10a-tetrahydropyrido[2',3':3,4]pyrrolo[1,2-a]pyrazin-5(7H)-one;

9-[(4-Fluoro-2-methylphenyl)sulfonyl]-8,9,10,10a-tetrahydropyrido[2',3':3,4]pyrrolo[1,2-a]pyrazin-5(7H)-one;

9-({4-[(Difluoromethyl)oxy]phenyl}sulfonyl)-8,9,10,10a-tetrahydropyrido[2',3':3,4]pyrrolo[1,2-a]pyrazin-5(7H)-one;

9-({4-[(Trifluoromethyl)oxy]phenyl}sulfonyl)-8,9,10,10a-tetrahydropyrido[2',3':3,4]pyrrolo[1,2-a]pyrazin-5(7H)-one;

3,5-Dimethyl-4-[(5-oxo-7,8,10,10a-tetrahydropyrido[2',3':3,4]pyrrolo[1,2-a]pyrazin-9(5H)-yl)sulfonyl]benzonitrile;

2,6-Dimethyl-4-[(5-oxo-7,8,10,10a-tetrahydropyrido[2',3':3,4]pyrrolo[1,2-a]pyrazin-9(5H)-yl)sulfonyl]benzonitrile;

9-{[3-(Trifluoromethyl)phenyl]sulfonyl}-8,9,10,10a-tetrahydropyrido[2',3':3,4]pyrrolo[1,2-a]pyrazin-5(7H)-one;

9-({3-[(Trifluoromethyl)oxy]phenyl}sulfonyl)-8,9,10,10a-tetrahydropyrido[2',3':3,4]pyrrolo[1,2-a]pyrazin-5(7H)-one;

9-({3-[(Difluoromethyl)oxy]phenyl}sulfonyl)-8,9,10,10a-tetrahydropyrido[2',3':3,4]pyrrolo[1,2-a]pyrazin-5(7H)-one;

9-({2-Methyl-4-[(trifluoromethyl)oxy]phenyl}sulfonyl)-8,9,10,10a-tetrahydropyrido[2',3':3,4]pyrrolo[1,2-a]pyrazin-5(7H)-one;

9-({4-[(Difluoromethyl)oxy]-2-methylphenyl}sulfonyl)-8,9,10,10a-tetrahydropyrido[2',3':3,4]pyrrolo[1,2-a]pyrazin-5(7H)-one;

9-({4-[(Fluoromethyl)oxy]-2-methylphenyl}sulfonyl)-8,9,10,10a-tetrahydropyrido[2',3':3,4]pyrrolo[1,2-a]pyrazin-5(7H)-one;

9-({4-[(Fluoromethyl)oxy]phenyl}sulfonyl)-8,9,10,10a-tetrahydropyrido[2',3':3,4]pyrrolo[1,2-a]pyrazin-5(7H)-one;

9-({3-[(Fluoromethyl)oxy]phenyl}sulfonyl)-8,9,10,10a-tetrahydropyrido[2',3':3,4]pyrrolo[1,2-a]pyrazin-5(7H)-one;

10a-Methyl-9-{[2-methyl-4-(trifluoromethyl)phenyl]sulfonyl}-8,9,10,10a-tetrahydropyrido[2',3':3,4]pyrrolo[1,2-a]pyrazin-5(7H)-one;

10a-Methyl-9-({4-[(1-methylethyl)oxy]phenyl}sulfonyl)-8,9,10,10a-tetrahydropyrido[2',3':3,4]pyrrolo[1,2-a]pyrazin-5(7H)-one;

3-[(10a-Methyl-5-oxo-7,8,10,10a-tetrahydropyrido[2',3':3,4]pyrrolo[1,2-a]pyrazin-9(5H)-yl)sulfonyl]benzonitrile;

10a-Methyl-9-{[4-(trifluoromethyl)phenyl]sulfonyl}-8,9,10,10a-tetrahydropyrido[2',3':3,4]pyrrolo[1,2-a]pyrazin-5(7H)-one;

3-Methyl-4-[(10a-methyl-5-oxo-7,8,10,10a-tetrahydropyrido[2',3':3,4]pyrrolo[1,2-a]pyrazin-9(5H)-yl)sulfonyl]benzonitrile;

9-{[2,6-Dimethyl-4-(methyloxy)phenyl]sulfonyl}-10a-methyl-8,9,10,10a-tetrahydropyrido[2',3':3,4]pyrrolo[1,2-a]pyrazin-5(7H)-one;

4-Chloro-2-[(10a-methyl-5-oxo-7,8,10,10a-tetrahydropyrido[2',3':3,4]pyrrolo[1,2-a]pyrazin-9(5H)-yl)sulfonyl]benzonitrile;

4-[(10a-Methyl-5-oxo-7,8,10,10a-tetrahydropyrido[2',3':3,4]pyrrolo[1,2-a]pyrazin-9(5H)-yl)sulfonyl]-3-(trifluoromethyl)benzonitrile;

3-Chloro-4-[(10a-methyl-5-oxo-7,8,10,10a-tetrahydropyrido[2',3':3,4]pyrrolo[1,2-a]pyrazin-9(5H)-yl)sulfonyl]benzonitrile;

9-{[4-(Ethyloxy)-2,5-dimethylphenyl]sulfonyl}-10a-methyl-8,9,10,10a-tetrahydropyrido[2',3':3,4]pyrrolo[1,2-a]pyrazin-5(7H)-one;

9-[(4-Fluoro-2-methylphenyl)sulfonyl]-10a-methyl-8,9,10,10a-tetrahydropyrido[2',3':3,4]pyrrolo[1,2-a]pyrazin-5(7H)-one;

9-({4-[(Difluoromethyl)oxy]phenyl}sulfonyl)-10a-methyl-8,9,10,10a-tetrahydropyrido[2',3':3,4]pyrrolo[1,2-a]pyrazin-5(7H)-one;

10a-Methyl-9-({4-[(trifluoromethyl)oxy]phenyl}sulfonyl)-8,9,10,10a-tetrahydropyrido[2',3':3,4]pyrrolo[1,2-a]pyrazin-5(7H)-one;

3,5-Dimethyl-4-[(10a-methyl-5-oxo-7,8,10,10a-tetrahydropyrido[2',3':3,4]pyrrolo[1,2-a]pyrazin-9(5H)-yl)sulfonyl]benzonitrile;

2,6-Dimethyl-4-[(10a-methyl-5-oxo-7,8,10,10a-tetrahydropyrido[2',3':3,4]pyrrolo[1,2-a]pyrazin-9(5H)-yl)sulfonyl]benzonitrile;

10a-Methyl-9-{[3-(trifluoromethyl)phenyl]sulfonyl}-8,9,10,10a-tetrahydropyrido[2',3':3,4]pyrrolo[1,2-a]pyrazin-5(7H)-one;

10a-Methyl-9-({3-[(trifluoromethyl)oxy]phenyl}sulfonyl)-8,9,10,10a-tetrahydropyrido[2',3':3,4]pyrrolo[1,2-a]pyrazin-5(7H)-one;

9-({3-[(Difluoromethyl)oxy]phenyl}sulfonyl)-10a-methyl-8,9,10,10a-tetrahydropyrido[2',3':3,4]pyrrolo[1,2-a]pyrazin-5(7H)-one;

10a-Methyl-9-({2-methyl-4-[(trifluoromethyl)oxy]phenyl}sulfonyl)-8,9,10,10a-tetrahydropyrido[2',3':3,4]pyrrolo[1,2-a]pyrazin-5(7H)-one;

9-({4-[(Difluoromethyl)oxy]-2-methylphenyl}sulfonyl)-10a-methyl-8,9,10,10a-tetrahydropyrido[2',3':3,4]pyrrolo[1,2-a]pyrazin-5(7H)-one;

9-({4-[(Fluoromethyl)oxy]-2-methylphenyl}sulfonyl)-10a-methyl-8,9,10,10a-tetrahydropyrido[2',3':3,4]pyrrolo[1,2-a]pyrazin-5(7H)-one;

9-({4-[(Fluoromethyl)oxy]phenyl}sulfonyl)-10a-methyl-8,9,10,10a-tetrahydropyrido[2',3':3,4]pyrrolo[1,2-a]pyrazin-5(7H)-one;

9-({3-[(Fluoromethyl)oxy]phenyl}sulfonyl)-10a-methyl-8,9,10,10a-tetrahydropyrido[2',3':3,4]pyrrolo[1,2-a]pyrazin-5(7H)-one;

2,10a-Dimethyl-9-{[2-methyl-4-(trifluoromethyl)phenyl]sulfonyl}-8,9,10,10a-tetrahydropyrido[2',3':3,4]pyrrolo[1,2-a]pyrazin-5(7H)-one;

9-{[4-(Ethyloxy)phenyl]sulfonyl}-2,10a-dimethyl-8,9,10,10a-tetrahydropyrido[2',3':3,4]pyrrolo[1,2-a]pyrazin-5(7H)-one;

2,10a-Dimethyl-9-({4-[(1-methylethyl)oxy]phenyl}sulfonyl)-8,9,10,10a-tetrahydropyrido[2',3':3,4]pyrrolo[1,2-a]pyrazin-5(7H)-one;

3-[(2, 10a-Dimethyl-5-oxo-7,8,10,10a-tetrahydropyrido[2',3':3,4]pyrrolo[1,2-a]pyrazin-9(5H)-yl)sulfonyl]benzonitrile;

2,10a-Dimethyl-9-{[4-(trifluoromethyl)phenyl]sulfonyl}-8,9,10,10a-tetrahydropyrido[2',3':3,4]pyrrolo[1,2-a]pyrazin-5(7H)-one;

4-[(2, 10a-Dimethyl-5-oxo-7,8,10,10a-tetrahydropyrido[2',3':3,4]pyrrolo[1,2-a]pyrazin-9(5H)-yl)sulfonyl]-3-methylbenzonitrile;

9-{[2,6-Dimethyl-4-(methyloxy)phenyl]sulfonyl}-2,10a-dimethyl-8,9,10,10a-tetrahydropyrido[2',3':3,4]pyrrolo[1,2-a]pyrazin-5(7H)-one;

4-Chloro-2-[(2,10a-dimethyl-5-oxo-7,8,10,10a-tetrahydropyrido[2',3':3,4]pyrrolo[1,2-a]pyrazin-9(5H)-yl)sulfonyl]benzonitrile;

4-[(2, 10a-Dimethyl-5-oxo-7,8,10,10a-tetrahydropyrido[2',3':3,4]pyrrolo[1,2-a]pyrazin-9(5H)-yl)sulfonyl]-3-(trifluoromethyl)benzonitrile;

3-Chloro-4-[(2,10a-dimethyl-5-oxo-7,8,10,10a-tetrahydropyrido[2',3':3,4]pyrrolo[1,2-a]pyrazin-9(5H)-yl)sulfonyl]benzonitrile;

9-{[4-(Ethyloxy)-2,5-dimethylphenyl]sulfonyl}-2,10a-dimethyl-8,9,10,10a-tetrahydropyrido[2',3':3,4]pyrrolo[1,2-a]pyrazin-5(7H)-one;

9-[(4-Fluoro-2-methylphenyl)sulfonyl]-2,10a-dimethyl-8,9,10,10a-tetrahydropyrido[2',3':3,4]pyrrolo[1,2-a]pyrazin-5(7H)-one;

9-({4-[(Difluoromethyl)oxy]phenyl}sulfonyl)-2,10a-dimethyl-8,9,10,10a-tetrahydropyrido[2',3':3,4]pyrrolo[1,2-a]pyrazin-5(7H)-one;

2,10a-Dimethyl-9-({4-[(trifluoromethyl)oxy]phenyl}sulfonyl)-8,9,10,10a-tetrahydropyrido[2',3':3,4]pyrrolo[1,2-a]pyrazin-5(7H)-one;

4-[(2, 10a-Dimethyl-5-oxo-7,8,10,10a-tetrahydropyrido[2',3':3,4]pyrrolo[1,2-a]pyrazin-9(5H)-yl)sulfonyl]-3,5-dimethylbenzonitrile;

4-[(2, 10a-Dimethyl-5-oxo-7,8,10,10a-tetrahydropyrido[2',3':3,4]pyrrolo[1,2-a]pyrazin-9(5H)-yl)sulfonyl]-2,6-dimethylbenzonitrile;

2,10a-Dimethyl-9-{[3-(trifluoromethyl)phenyl]sulfonyl}-8,9,10,10a-tetrahydropyrido[2',3':3,4]pyrrolo[1,2-a]pyrazin-5(7H)-one;

2,10a-Dimethyl-9-({3-[(trifluoromethyl)oxy]phenyl}sulfonyl)-8,9,10,10a-tetrahydropyrido[2',3':3,4]pyrrolo[1,2-a]pyrazin-5(7H)-one;

9-({3-[(Difluoromethyl)oxy]phenyl}sulfonyl)-2,10a-dimethyl-8,9,10,10a-tetrahydropyrido[2',3':3,4]pyrrolo[1,2-a]pyrazin-5(7H)-one;

2,10a-Dimethyl-9-({2-methyl-4-[(trifluoromethyl)oxy]phenyl}sulfonyl)-8,9,10,10a-tetrahydropyrido[2',3':3,4]pyrrolo[1,2-a]pyrazin-5(7H)-one;

9-({4-[(Difluoromethyl)oxy]-2-methylphenyl}sulfonyl)-2,10a-dimethyl-8,9,10,10a-tetrahydropyrido[2',3':3,4]pyrrolo[1,2-a]pyrazin-5(7H)-one;

9-({4-[(Fluoromethyl)oxy]-2-methylphenyl}sulfonyl)-2,10a-dimethyl-8,9,10,10a-tetrahydropyrido[2',3':3,4]pyrrolo[1,2-a]pyrazin-5(7H)-one;

9-({4-[(Fluoromethyl)oxy]phenyl}sulfonyl)-2,10a-dimethyl-8,9,10,10a-tetrahydropyrido[2',3':3,4]pyrrolo[1,2-a]pyrazin-5(7H)-one;

9-({3-[(Fluoromethyl)oxy]phenyl}sulfonyl)-2,10a-dimethyl-8,9,10,10a-tetrahydropyrido[2',3':3,4]pyrrolo[1,2-a]pyrazin-5(7H)-one;

9,10b-Dimethyl-2-{[2-methyl-4-(trifluoromethyl)phenyl]sulfonyl}-1,3,4,10b-tetrahydropyrido[4',3':3,4]pyrrolo[1,2-a]pyrazin-6(2H)-one;

2-{[4-(Ethyloxy)phenyl]sulfonyl}-9,10b-dimethyl-1,3,4,10b-tetrahydropyrido[4',3':3,4]pyrrolo[1,2-a]pyrazin-6(2H)-one;

9,10b-Dimethyl-2-({4-[(1-methylethyl)oxy]phenyl}sulfonyl)-1,3,4,10b-tetrahydropyrido[4',3':3,4]pyrrolo[1,2-a]pyrazin-6(2H)-one;

3-[(9,10b-Dimethyl-6-oxo-3,4,6,10b-tetrahydropyrido[4',3':3,4]pyrrolo[1,2-a]pyrazin-2(1H)-yl)sulfonyl]benzonitrile;

9,10b-Dimethyl-2-{[4-(trifluoromethyl)phenyl]sulfonyl}-1,3,4,10b-tetrahydropyrido[4',3':3,4]pyrrolo[1,2-a]pyrazin-6(2H)-one;

4-[(9,10b-Dimethyl-6-oxo-3,4,6,10b-tetrahydropyrido[4',3':3,4]pyrrolo[1,2-a]pyrazin-2(1H)-yl)sulfonyl]-3-methylbenzonitrile;

2-{[2,6-Dimethyl-4-(methyloxy)phenyl]sulfonyl}-9,10b-dimethyl-1,3,4,10b-tetrahydropyrido[4',3':3,4]pyrrolo[1,2-a]pyrazin-6(2H)-one;

4-Chloro-2-[(9,10b-dimethyl-6-oxo-3,4,6,10b-tetrahydropyrido[4',3':3,4]pyrrolo[1,2-a]pyrazin-2(1H)-yl)sulfonyl]benzonitrile;

4-[(9,10b-Dimethyl-6-oxo-3,4,6,10b-tetrahydropyrido[4',3':3,4]pyrrolo[1,2-a]pyrazin-2(1H)-yl)sulfonyl]-3-(trifluoromethyl)benzonitrile;

3-Chloro-4-[(9,10b-dimethyl-6-oxo-3,4,6,10b-tetrahydropyrido[4',3':3,4]pyrrolo[1,2-a]pyrazin-2(1H)-yl)sulfonyl]benzonitrile;

2-{[4-(Ethyloxy)-2,5-dimethylphenyl]sulfonyl}-9,10b-dimethyl-1,3,4,10b-tetrahydropyrido[4',3':3,4]pyrrolo[1,2-a]pyrazin-6(2H)-one;

2-[(4-Fluoro-2-methylphenyl)sulfonyl]-9,10b-dimethyl-1,3,4,10b-tetrahydropyrido[4',3':3,4]pyrrolo[1,2-a]pyrazin-6(2H)-one;

2-({4-[(Difluoromethyl)oxy]phenyl}sulfonyl)-9,10b-dimethyl-1,3,4,10b-tetrahydropyrido[4',3':3,4]pyrrolo[1,2-a]pyrazin-6(2H)-one;

9,10b-Dimethyl-2-({4-[(trifluoromethyl)oxy]phenyl}sulfonyl)-1,3,4,10b-tetrahydropyrido[4',3':3,4]pyrrolo[1,2-a]pyrazin-6(2H)-one;

4-[(9,10b-Dimethyl-6-oxo-3,4,6,10b-tetrahydropyrido[4',3':3,4]pyrrolo[1,2-a]pyrazin-2(1H)-yl)sulfonyl]-3,5-dimethylbenzonitrile;

4-[(9,10b-Dimethyl-6-oxo-3,4,6,10b-tetrahydropyrido[4',3':3,4]pyrrolo[1,2-a]pyrazin-2(1H)-yl)sulfonyl]-2,6-dimethylbenzonitrile;

9,10b-Dimethyl-2-{[3-(trifluoromethyl)phenyl]sulfonyl}-1,3,4,10b-tetrahydropyrido[4',3':3,4]pyrrolo[1,2-a]pyrazin-6(2H)-one;

9,10b-Dimethyl-2-({3-[(trifluoromethyl)oxy]phenyl}sulfonyl)-1,3,4,10b-tetrahydropyrido[4',3':3,4]pyrrolo[1,2-a]pyrazin-6(2H)-one;

2-({3-[(Difluoromethyl)oxy]phenyl}sulfonyl)-9,10b-dimethyl-1,3,4,10b-tetrahydropyrido[4',3':3,4]pyrrolo[1,2-a]pyrazin-6(2H)-one;

9,10b-Dimethyl-2-({2-methyl-4-[(trifluoromethyl)oxy]phenyl}sulfonyl)-1,3,4,10b-tetrahydropyrido[4',3':3,4]pyrrolo[1,2-a]pyrazin-6(2H)-one;

2-({4-[(Difluoromethyl)oxy]-2-methylphenyl}sulfonyl)-9,10b-dimethyl-1,3,4,10b-tetrahydropyrido[4',3':3,4]pyrrolo[1,2-a]pyrazin-6(2H)-one;

2-({4-[(Fluoromethyl)oxy]-2-methylphenyl}sulfonyl)-9,10b-dimethyl-1,3,4,10b-tetrahydropyrido[4',3':3,4]pyrrolo[1,2-a]pyrazin-6(2H)-one;

2-({4-[(Fluoromethyl)oxy]phenyl}sulfonyl)-9,10b-dimethyl-1,3,4,10b-tetrahydropyrido[4',3':3,4]pyrrolo[1,2-a]pyrazin-6(2H)-one;

2-({3-[(Fluoromethyl)oxy]phenyl}sulfonyl)-9,10b-dimethyl-1,3,4,10b-tetrahydropyrido[4',3':3,4]pyrrolo[1,2-a]pyrazin-6(2H)-one;

7,10b-Dimethyl-2-{[2-methyl-4-(trifluoromethyl)phenyl]sulfonyl}-1,3,4,10b-tetrahydropyrido[4',3':3,4]pyrrolo[1,2-a]pyrazin-6(2H)-one;

2-{[4-(Ethyloxy)phenyl]sulfonyl}-7,10b-dimethyl-1,3,4,10b-tetrahydropyrido[4',3':3,4]pyrrolo[1,2-a]pyrazin-6(2H)-one;

7,10b-Dimethyl-2-({4-[(1-methylethyl)oxy]phenyl}sulfonyl)-1,3,4,10b-tetrahydropyrido[4',3':3,4]pyrrolo[1,2-a]pyrazin-6(2H)-one;

7,10b-Dimethyl-2-{[4-(trifluoromethyl)phenyl]sulfonyl}-1,3,4,10b-tetrahydropyrido[4',3':3,4]pyrrolo[1,2-a]pyrazin-6(2H)-one;

4-[(7,10b-Dimethyl-6-oxo-3,4,6,10b-tetrahydropyrido[4',3':3,4]pyrrolo[1,2-a]pyrazin-2(1H)-yl)sulfonyl]-3-methylbenzonitrile;

4-[(7,10b-Dimethyl-6-oxo-3,4,6,10b-tetrahydropyrido[4',3':3,4]pyrrolo[1,2-a]pyrazin-2(1H)-yl)sulfonyl]-3-methylbenzonitrile;

4-Chloro-2-[(7,10b-dimethyl-6-oxo-3,4,6,10b-tetrahydropyrido[4',3':3,4]pyrrolo[1,2-a]pyrazin-2(1H)-yl)sulfonyl]benzonitrile;

4-[(7,10b-Dimethyl-6-oxo-3,4,6,10b-tetrahydropyrido[4',3':3,4]pyrrolo[1,2-a]pyrazin-2(1H)-yl)sulfonyl]-3-(trifluoromethyl)benzonitrile;

3-Chloro-4-[(7,10b-dimethyl-6-oxo-3,4,6,10b-tetrahydropyrido[4',3':3,4]pyrrolo[1,2-a]pyrazin-2(1H)-yl)sulfonyl]benzonitrile;

2-{[4-(Ethyloxy)-2,5-dimethylphenyl]sulfonyl}-7,10b-dimethyl-1,3,4,10b-tetrahydropyrido[4',3':3,4]pyrrolo[1,2-a]pyrazin-6(2H)-one;

2-[(4-Fluoro-2-methylphenyl)sulfonyl]-7,10b-dimethyl-1,3,4,10b-tetrahydropyrido[4',3':3,4]pyrrolo[1,2-a]pyrazin-6(2H)-one;

2-({4-[(Difluoromethyl)oxy]phenyl}sulfonyl)-7,10b-dimethyl-1,3,4,10b-tetrahydropyrido[4',3':3,4]pyrrolo[1,2-a]pyrazin-6(2H)-one;

7,10b-Dimethyl-2-({4-[(trifluoromethyl)oxy]phenyl}sulfonyl)-1,3,4,10b-tetrahydropyrido[4',3':3,4]pyrrolo[1,2-a]pyrazin-6(2H)-one;

4-[(7,10b-Dimethyl-6-oxo-3,4,6,10b-tetrahydropyrido[4',3':3,4]pyrrolo[1,2-a]pyrazin-2(1H)-yl)sulfonyl]-3,5-dimethylbenzonitrile;

4-[(7,10b-Dimethyl-6-oxo-3,4,6,10b-tetrahydropyrido[4',3':3,4]pyrrolo[1,2-a]pyrazin-2(1H)-yl)sulfonyl]-2,6-dimethylbenzonitrile;

7,10b-Dimethyl-2-{[3-(trifluoromethyl)phenyl]sulfonyl}-1,3,4,10b-tetrahydropyrido[4',3':3,4]pyrrolo[1,2-a]pyrazin-6(2H)-one;

7,10b-Dimethyl-2-({3-[(trifluoromethyl)oxy]phenyl}sulfonyl)-1,3,4,10b-tetrahydropyrido[4',3':3,4]pyrrolo[1,2-a]pyrazin-6(2H)-one;

2-({3-[(Difluoromethyl)oxy]phenyl}sulfonyl)-7,10b-dimethyl-1,3,4,10b-tetrahydropyrido[4',3':3,4]pyrrolo[1,2-a]pyrazin-6(2H)-one;

7,10b-Dimethyl-2-({2-methyl-4-[(trifluoromethyl)oxy]phenyl}sulfonyl)-1,3,4,10b-tetrahydropyrido[4',3':3,4]pyrrolo[1,2-a]pyrazin-6(2H)-one;

2-({4-[(Difluoromethyl)oxy]-2-methylphenyl}sulfonyl)-7,10b-dimethyl-1,3,4,10b-tetrahydropyrido[4',3':3,4]pyrrolo[1,2-a]pyrazin-6(2H)-one;

2-({4-[(Fluoromethyl)oxy]-2-methylphenyl}sulfonyl)-7,10b-dimethyl-1,3,4,10b-tetrahydropyrido[4',3':3,4]pyrrolo[1,2-a]pyrazin-6(2H)-one;

2-({4-[(Fluoromethyl)oxy]phenyl}sulfonyl)-7,10b-dimethyl-1,3,4,10b-tetrahydropyrido[4',3':3,4]pyrrolo[1,2-a]pyrazin-6(2H)-one;

2-({3-[(Fluoromethyl)oxy]phenyl}sulfonyl)-7,10b-dimethyl-1,3,4,10b-tetrahydropyrido[4',3':3,4]pyrrolo[1,2-a]pyrazin-6(2H)-one;

9-Methyl-2-{[2-methyl-4-(trifluoromethyl)phenyl]sulfonyl}-1,3,4,10b-tetrahydropyrido[4',3':3,4]pyrrolo[1,2-a]pyrazin-6(2H)-one;

2-{[4-(Ethyloxy)phenyl]sulfonyl}-9-methyl-1,3,4,10b-tetrahydropyrido[4',3':3,4]pyrrolo[1,2-a]pyrazin-6(2H)-one;

9-Methyl-2-({4-[(1-methylethyl)oxy]phenyl}sulfonyl)-1,3,4,10b-tetrahydropyrido[4',3':3,4]pyrrolo[1,2-a]pyrazin-6(2H)-one;

9-Methyl-2-{[4-(trifluoromethyl)phenyl]sulfonyl}-1,3,4,10b-tetrahydropyrido[4',3':3,4]pyrrolo[1,2-a]pyrazin-6(2H)-one;

3-Methyl-4-[(9-methyl-6-oxo-3,4,6,10b-tetrahydropyrido[4',3':3,4]pyrrolo[1,2-a]pyrazin-2(1H)-yl)sulfonyl]benzonitrile;

2-{[2,6-Dimethyl-4-(methyloxy)phenyl]sulfonyl}-9-methyl-1,3,4,10b-tetrahydropyrido[4',3':3,4]pyrrolo[1,2-a]pyrazin-6(2H)-one;

4-Chloro-2-[(9-methyl-6-oxo-3,4,6,10b-tetrahydropyrido[4',3':3,4]pyrrolo[1,2-a]pyrazin-2(1H)-yl)sulfonyl]benzonitrile;

4-[(9-Methyl-6-oxo-3,4,6,10b-tetrahydropyrido[4',3':3,4]pyrrolo[1,2-a]pyrazin-2(1H)-yl)sulfonyl]-3-(trifluoromethyl)benzonitrile;

3-Chloro-4-[(9-methyl-6-oxo-3,4,6,10b-tetrahydropyrido[4',3':3,4]pyrrolo[1,2-a]pyrazin-2(1H)-yl)sulfonyl]benzonitrile;

2-{[4-(Ethyloxy)-2,5-dimethylphenyl]sulfonyl}-9-methyl-1,3,4,10b-tetrahydropyrido[4',3':3,4]pyrrolo[1,2-a]pyrazin-6(2H)-one;

2-[(4-Fluoro-2-methylphenyl)sulfonyl]-9-methyl-1,3,4,10b-tetrahydropyrido[4',3':3,4]pyrrolo[1,2-a]pyrazin-6(2H)-one;

2-({4-[(Difluoromethyl)oxy]phenyl}sulfonyl)-9-methyl-1,3,4,10b-tetrahydropyrido[4',3':3,4]pyrrolo[1,2-a]pyrazin-6(2H)-one;

9-Methyl-2-({4-[(trifluoromethyl)oxy]phenyl}sulfonyl)-1,3,4,10b-tetrahydropyrido[4',3':3,4]pyrrolo[1,2-a]pyrazin-6(2H)-one;

3,5-Dimethyl-4-[(9-methyl-6-oxo-3,4,6,10b-tetrahydropyrido[4',3':3,4]pyrrolo[1,2-a]pyrazin-2(1H)-yl)sulfonyl]benzonitrile;

2,6-Dimethyl-4-[(9-methyl-6-oxo-3,4,6,10b-tetrahydropyrido[4',3':3,4]pyrrolo[1,2-a]pyrazin-2(1H)-yl)sulfonyl]benzonitrile;

9-Methyl-2-{[3-(trifluoromethyl)phenyl]sulfonyl}-1,3,4,10b-tetrahydropyrido[4',3':3,4]pyrrolo[1,2-a]pyrazin-6(2H)-one;

9-Methyl-2-({3-[(trifluoromethyl)oxy]phenyl}sulfonyl)-1,3,4,10b-tetrahydropyrido[4',3':3,4]pyrrolo[1,2-a]pyrazin-6(2H)-one;

2-({3-[(Difluoromethyl)oxy]phenyl}sulfonyl)-9-methyl-1,3,4,10b-tetrahydropyrido[4',3':3,4]pyrrolo[1,2-a]pyrazin-6(2H)-one;

9-Methyl-2-({2-methyl-4-[(trifluoromethyl)oxy]phenyl}sulfonyl)-1,3,4,10b-tetrahydropyrido[4',3':3,4]pyrrolo[1,2-a]pyrazin-6(2H)-one;

2-({4-[(Difluoromethyl)oxy]-2-methylphenyl}sulfonyl)-9-methyl-1,3,4,10b-tetrahydropyrido[4',3':3,4]pyrrolo[1,2-a]pyrazin-6(2H)-one;

2-({4-[(Fluoromethyl)oxy]-2-methylphenyl}sulfonyl)-9-methyl-1,3,4,10b-tetrahydropyrido[4',3':3,4]pyrrolo[1,2-a]pyrazin-6(2H)-one;

2-({4-[(Fluoromethyl)oxy]phenyl}sulfonyl)-9-methyl-1,3,4,10b-tetrahydropyrido[4',3':3,4]pyrrolo[1,2-a]pyrazin-6(2H)-one;

2-({3-[(Fluoromethyl)oxy]phenyl}sulfonyl)-9-methyl-1,3,4,10b-tetrahydropyrido[4',3':3,4]pyrrolo[1,2-a]pyrazin-6(2H)-one;

7-Methyl-2-{[2-methyl-4-(trifluoromethyl)phenyl]sulfonyl}-1,3,4,10b-tetrahydropyrido[4',3':3,4]pyrrolo[1,2-a]pyrazin-6(2H)-one;

2-{[4-(Ethyloxy)phenyl]sulfonyl}-7-methyl-1,3,4,10b-tetrahydropyrido[4',3':3,4]pyrrolo[1,2-a]pyrazin-6(2H)-one;

7-Methyl-2-({4-[(1-methylethyl)oxy]phenyl}sulfonyl)-1,3,4,10b-tetrahydropyrido[4',3':3,4]pyrrolo[1,2-a]pyrazin-6(2H)-one;

7-Methyl-2-{[4-(trifluoromethyl)phenyl]sulfonyl}-1,3,4,10b-tetrahydropyrido[4',3':3,4]pyrrolo[1,2-a]pyrazin-6(2H)-one;

3-Methyl-4-[(7-methyl-6-oxo-3,4,6,10b-tetrahydropyrido[4',3':3,4]pyrrolo[1,2-a]pyrazin-2(1H)-yl)sulfonyl]benzonitrile;

2-{[2,6-Dimethyl-4-(methyloxy)phenyl]sulfonyl}-7-methyl-1,3,4,10b-tetrahydropyrido[4',3':3,4]pyrrolo[1,2-a]pyrazin-6(2H)-one;

4-Chloro-2-[(7-methyl-6-oxo-3,4,6,10b-tetrahydropyrido[4',3':3,4]pyrrolo[1,2-a]pyrazin-2(1H)-yl)sulfonyl]benzonitrile;

4-[(7-Methyl-6-oxo-3,4,6,10b-tetrahydropyrido[4',3':3,4]pyrrolo[1,2-a]pyrazin-2(1H)-yl)sulfonyl]-3-(trifluoromethyl)benzonitrile;

3-Chloro-4-[(7-methyl-6-oxo-3,4,6,10b-tetrahydropyrido[4',3':3,4]pyrrolo[1,2-a]pyrazin-2(1H)-yl)sulfonyl]benzonitrile;

2-{[4-(Ethyloxy)-2,5-dimethylphenyl]sulfonyl}-7-methyl-1,3,4,10b-tetrahydropyrido[4',3':3,4]pyrrolo[1,2-a]pyrazin-6(2H)-one;

2-[(4-Fluoro-2-methylphenyl)sulfonyl]-7-methyl-1,3,4,10b-tetrahydropyrido[4',3':3,4]pyrrolo[1,2-a]pyrazin-6(2H)-one;

2-({4-[(Difluoromethyl)oxy]phenyl}sulfonyl)-7-methyl-1,3,4,10b-tetrahydropyrido[4',3':3,4]pyrrolo[1,2-a]pyrazin-6(2H)-one;

7-Methyl-2-({4-[(trifluoromethyl)oxy]phenyl}sulfonyl)-1,3,4,10b-tetrahydropyrido[4',3':3,4]pyrrolo[1,2-a]pyrazin-6(2H)-one;

3,5-Dimethyl-4-[(7-methyl-6-oxo-3,4,6,10b-tetrahydropyrido[4',3':3,4]pyrrolo[1,2-a]pyrazin-2(1H)-yl)sulfonyl]benzonitrile;

2,6-Dimethyl-4-[(7-methyl-6-oxo-3,4,6,10b-tetrahydropyrido[4',3':3,4]pyrrolo[1,2-a]pyrazin-2(1H)-yl)sulfonyl]benzonitrile;

7-Methyl-2-{[3-(trifluoromethyl)phenyl]sulfonyl}-1,3,4,10b-tetrahydropyrido[4',3':3,4]pyrrolo[1,2-a]pyrazin-6(2H)-one;

7-Methyl-2-({3-[(trifluoromethyl)oxy]phenyl}sulfonyl)-1,3,4,10b-tetrahydropyrido[4',3':3,4]pyrrolo[1,2-a]pyrazin-6(2H)-one;

2-({3-[(Difluoromethyl)oxy]phenyl}sulfonyl)-7-methyl-1,3,4,10b-tetrahydropyrido[4',3':3,4]pyrrolo[1,2-a]pyrazin-6(2H)-one;

7-Methyl-2-({2-methyl-4-[(trifluoromethyl)oxy]phenyl}sulfonyl)-1,3,4,10b-tetrahydropyrido[4',3':3,4]pyrrolo[1,2-a]pyrazin-6(2H)-one;

2-({4-[(Difluoromethyl)oxy]-2-methylphenyl}sulfonyl)-7-methyl-1,3,4,10b-tetrahydropyrido[4',3':3,4]pyrrolo[1,2-a]pyrazin-6(2H)-one;

2-({4-[(Fluoromethyl)oxy]-2-methylphenyl}sulfonyl)-7-methyl-1,3,4,10b-tetrahydropyrido[4',3':3,4]pyrrolo[1,2-a]pyrazin-6(2H)-one;

2-({4-[(Fluoromethyl)oxy]phenyl}sulfonyl)-7-methyl-1,3,4,10b-tetrahydropyrido[4',3':3,4]pyrrolo[1,2-a]pyrazin-6(2H)-one; and 2-({3-[(Fluoromethyl)oxy]phenyl}sulfonyl)-7-methyl-1,3,4,10b-tetrahydropyrido[4',3':3,4]pyrrolo[1,2-a]pyrazin-6(2H)-one, or a pharmaceutically acceptable salt thereof.

12. A pharmaceutical composition comprising (a) a compound, or a pharmaceutically acceptable salt thereof, according to claim 1 and (b) a pharmaceutically acceptable excipient.

13. A method for the treatment or prophylaxis of pain in a human in need thereof comprising administering to said human a therapeutically effective amount of a compound, or a pharmaceutically acceptable salt thereof, as defined in claim 1.

* * * * *